United States Patent
Wagers et al.

(10) Patent No.: US 10,092,627 B2
(45) Date of Patent: Oct. 9, 2018

(54) METHODS AND COMPOSITIONS FOR REJUVENATING SKELETAL MUSCLE STEM CELLS

(71) Applicants: President and Fellows of Harvard College, Cambridge, MA (US); THE BRIGHAM AND WOMEN'S HOSPITAL, INC., Boston, MA (US)

(72) Inventors: Amy J. Wagers, Cambridge, MA (US); Richard T. Lee, Weston, MA (US)

(73) Assignees: President and Fellows of Harvard College, Cambridge, MA (US); The Brigham and Womens's Hospital, Inc., Boston, MA (US)

( * ) Notice: Subject to any disclaimer, the term of this patent is extended or adjusted under 35 U.S.C. 154(b) by 0 days.

(21) Appl. No.: 14/783,426

(22) PCT Filed: Apr. 8, 2014

(86) PCT No.: PCT/US2014/033376
§ 371 (c)(1),
(2) Date: Oct. 8, 2015

(87) PCT Pub. No.: WO2014/168973
PCT Pub. Date: Oct. 16, 2014

(65) Prior Publication Data
US 2016/0074477 A1 Mar. 17, 2016

Related U.S. Application Data
(60) Provisional application No. 61/809,784, filed on Apr. 8, 2013.

(51) Int. Cl.
*A61K 38/18* (2006.01)
(52) U.S. Cl.
CPC .............................. *A61K 38/1875* (2013.01)
(58) Field of Classification Search
CPC ......... A61K 38/1875; B01L 2200/0689; B01L 2300/041; B01L 2300/0848; B01L 3/508; B01L 9/52; B04B 2007/025; B04B 5/0407; B04B 5/10; B04B 7/02; B04B 7/06; B04B 7/08; G01N 1/2813; G01N 2001/2846
See application file for complete search history.

(56) References Cited

U.S. PATENT DOCUMENTS

| | | | |
|---|---|---|---|
| 5,639,638 A | 6/1997 | Wozney et al. | |
| 5,700,911 A | 12/1997 | Wozney et al. | |
| 6,340,668 B1 | 1/2002 | Celeste et al. | |
| 6,517,835 B2 * | 2/2003 | Lee .................... | A01K 67/0276 424/130.1 |
| 6,555,672 B1 | 4/2003 | Liang | |
| 6,656,475 B1 | 12/2003 | Lee et al. | |
| 6,696,260 B1 | 2/2004 | Lee et al. | |
| 7,175,997 B2 | 2/2007 | Wozney et al. | |
| 7,202,210 B2 | 4/2007 | Wolfman et al. | |
| 7,384,753 B2 | 6/2008 | Lee et al. | |
| 7,560,441 B2 | 7/2009 | Wolfman et al. | |
| 7,572,440 B2 | 8/2009 | Vukicevic et al. | |
| 7,709,605 B2 | 5/2010 | Knopf et al. | |
| 7,976,839 B2 | 7/2011 | Lee et al. | |
| 8,067,562 B2 | 11/2011 | Han et al. | |
| 8,168,169 B2 | 5/2012 | Cataldo et al. | |
| 8,222,384 B2 | 7/2012 | Wolfman et al. | |
| 8,323,964 B2 | 12/2012 | Lee et al. | |
| 8,952,130 B2 | 2/2015 | Choe et al. | |
| 9,434,779 B2 * | 9/2016 | Lee ........................ | C07K 14/71 |
| 2002/0150577 A1 | 10/2002 | Lee et al. | |
| 2003/0083252 A1 | 5/2003 | Celeste et al. | |
| 2003/0104977 A1 | 6/2003 | Ripamonti et al. | |
| 2003/0167492 A1 | 9/2003 | Lee et al. | |
| 2003/0170213 A1 | 9/2003 | Charette | |
| 2003/0224501 A1 | 12/2003 | Young et al. | |
| 2005/0197367 A1 | 9/2005 | Li et al. | |
| 2006/0172391 A1 | 8/2006 | Wozney et al. | |
| 2006/0216279 A1 | 9/2006 | Glass et al. | |
| 2007/0253962 A1 | 11/2007 | Hirsch et al. | |
| 2007/0275895 A1 | 11/2007 | Duan et al. | |
| 2008/0044387 A1 | 2/2008 | Conboy et al. | |
| 2009/0215671 A1 | 8/2009 | Calof et al. | |
| 2009/0263402 A1 | 10/2009 | Lee et al. | |
| 2010/0196332 A1 | 8/2010 | Wichterle et al. | |
| 2010/0221777 A1 | 9/2010 | Choe et al. | |
| 2011/0027177 A1 | 2/2011 | Jacoby et al. | |
| 2011/0105395 A1 | 5/2011 | Fallon et al. | |
| 2011/0200580 A1 | 8/2011 | Karp et al. | |
| 2013/0071393 A1 | 3/2013 | Seehra et al. | |

(Continued)

FOREIGN PATENT DOCUMENTS

| | | |
|---|---|---|
| EP | 1378572 B2 | 10/2006 |
| EP | 1790726 B1 | 7/2013 |

(Continued)

OTHER PUBLICATIONS

Andersson, et al., "Growth Differentiation Factor 11 Signals Through the Transforming Growth Factor-β Receptor ALK5 to Regionalize the Anterior-Posterior Axis," *EMBO Reports*, 7(8)831-837, (2006).
Hannan, et al., "BMP-11 and Myostatin Support Undifferentiated Growth of Human Embryonic Stem Cells in Feeder-Free Cultures," *Cloning and Stem Cells*, 11(3):427-435, (2009).
Wu, et al., "Autoregulations of Neurogenesis by GDF-11," *Neuron*, 37:197-207, (Jan. 23, 2003).
Extended European Search Report for EP 14810402.9, dated Feb. 13, 2017.
Nedachi, et al. Contractile C2C12 myotube model for studying exercise-inducible responses in skeletal muscle. Am J Physiol Endocrinol Metab. 295(5):E1191-204; (2008).

(Continued)

*Primary Examiner* — Marcela M Cordero Garcia
(74) *Attorney, Agent, or Firm* — Morse, Barnes-Brown & Pendleton, P.C.; Lisa M. Warren, Esq.

(57) ABSTRACT

Methods and compositions for rejuvenating skeletal muscle stem cells are disclosed.

14 Claims, 26 Drawing Sheets
Specification includes a Sequence Listing.

(56) References Cited

U.S. PATENT DOCUMENTS

| | | | |
|---|---|---|---|
| 2013/0108645 A1 | 5/2013 | Farah | |
| 2013/0156767 A1 | 6/2013 | Walsh et al. | |
| 2015/0218522 A1* | 8/2015 | Peterson | C12N 5/0676 |
| | | | 435/366 |
| 2016/0220640 A1 | 8/2016 | Rubin et al. | |
| 2016/0264657 A1 | 9/2016 | Lee et al. | |
| 2016/0287667 A1* | 10/2016 | Wagers | A61K 38/1875 |

FOREIGN PATENT DOCUMENTS

| | | |
|---|---|---|
| WO | WO 98/35019 | 8/1998 |
| WO | WO 99/24058 A2 | 5/1999 |
| WO | WO 2002/10214 | 2/2002 |
| WO | WO 2002/068650 A2 | 9/2002 |
| WO | WO 2005/094446 A2 | 10/2005 |
| WO | WO 2006/116269 A2 | 11/2006 |
| WO | WO 2010/099219 A2 | 9/2010 |
| WO | WO 2012/135623 A1 | 10/2012 |
| WO | WO 2013/142114 A1 | 9/2013 |
| WO | WO 2014/168973 | 10/2014 |
| WO | WO 2014/201143 A1 | 12/2014 |
| WO | WO 2015/034897 A1 | 3/2015 |
| WO | WO 2015/070076 A2 | 5/2015 |
| WO | WO 2015/073396 A1 | 5/2015 |
| WO | WO 2015/171691 | 11/2015 |
| WO | WO 2016/049662 A1 | 3/2016 |
| WO | WO 2017/120450 A1 | 7/2017 |

OTHER PUBLICATIONS

Zhu, et al. Follistatin improves skeletal muscle healing after injury and disease through an interaction with muscle regeneration, angiogenesis, and fibrosis. Am J Pathol., 179(2):915-30; (2011).

Marzetti, et al. Mitochondrial death effectors: relevance to sarcopenia and disuse muscle atrophy. Biochim Biophys Acta, 1800(3):235-44; (2010).

Krakora, et al., Neuromuscular Junction Protection for the Potential Treatment of Amyotrophic Lateral Sclerosis, Hindawi Publishing CorporationNeurology Research International vol. 2012; 8 pages.

Ruckh, et al.,"Rejuvenation of regeneration in the aging central nervous System," Cell Stem Cell 10(1): 96-103 (2012).

Wagers, et al., "Cellular and Molecular Signatures of Muscle Regeneration: Current Concepts and Controversies in Adult Myogenesis," Cell, vol. 122, 659-667 (2005).

Souza, et al. "Proteomic Identification and Functional Validation of Activins and Bone Morphogenetic Protein 11 as Candidate Novel Muscle Mass Regulators," Molecular Endocrinology 22(12):2689-2702 (2008).

Amy Wagers, "Systemic regulation of aging phenotypes in mammalian tissues" HHMI, Harvard University, and Joslin Diabetes Center Sep. 26, 2013.

International Search Report for International Application PCT/US2014/33376, dated Sep. 26, 2015.

International Search Report for International Application PCT/US2014/064648, dated May 20, 2015.

Katsimpardi, et al., "Vascular and Neurogenic Rejuvenation of the Aging Mouse Brain by Young Systemic Factors," Science, 344:630-634, (May 9, 2014).

International Search Report for PCT/US2017/012505, dated May 4, 2017.

Final Office Action from U.S. Appl. No. 14/897,605, dated May 23, 2017.

Final Office Action for U.S. Appl. No. 14/897,605, dated Nov. 2, 2017.

Final Office Action for U.S. Appl. No. 15/035,331, dated Nov. 2, 2017.

Bowie, et al., "Deciphering the Message in Protein Sequences: Tolerance to Amino Acid Substitutions," Science, 247(4948):1306-1310, (Mar. 16, 1990).

Burgess, et al., "Possible Dissociation of the Heparin Binding and Mitogenic Activities of Heparin-Binding (Acidic Fibroblast) Growth Factor-1 from Its Receptor-Binding Activities by Site-Directed Mutagenesis of a Single Lysine Residue," J. of Cell Biol., 111:2129-2138, (1990).

Coyle, et al., "Physical Activity as a Metabolic Stressor," Am. J. Clin. Nutr., 72:512S-20S, (2000).

Pawson, et al., "Assembly of Cell Regulatory Systems Through Protein Interaction Domains," Science, 300:445-452, (Apr. 18, 2003).

Non-Final Office Action from U.S. Appl. No. 15/035,331 dated Apr. 20, 2017.

Egerman, et al., "GDF11 Increases with Age and Inhibits Skeletal Muscle Regeneration," Cell Metabolism, 22:164-174, (2015).

Lee, et al., "Regulation of GDF-11 and Myostatin Activity by GASP-1 and GASP-2," Proc Natl Acad Sci USA, 110(39):3713-3722, (Sep. 2013).

Loffredo, et al., "Growth Differentiation Factor 11 is a Circulating Factor that Reverses Age-Related Cardiac Hyperthrophy," Cell, 153(4):828-839, (May 2013).

Loffredo, et al., "Heart Failure with Preserved Ejection Fraction: Molecular Pathways of the Aging Myocardium," Circ Res, 115(1):97-107, (Jun. 2014).

Extended European Search Report from EP 14782154.0, dated Nov. 22, 2016.

International Search Report for International Application No. PCT/US2014/041952, dated Oct. 31, 2014.

International Search Report for International Application PCT/US2015/062226, dated Mar. 4, 2016.

Non-Final Office Action for U.S. Appl. No. 14/897,605, dated Dec. 14, 2016.

Anger, "Animal Test Systems to Study Behavioral Dysfunction," Neurotoxicology, 12(3):403-413, (1991).

Aziz, et al. "Diastolic Heart Failure: A Concise Review," J. Clin. Med. Res., 5(5):327-334, (2013).

Brack, "Ageing of the Heart Reversed by Youthful Systemic Factors," The EMBO Journal, 32:2189-2190, (2013).

Brun, et al., "GDF11 and the Mythical Fountain of Youth," Cell Metabolism, 22:54-54, (2015).

Harper, et al., "Is Growth Differentiation Factor 11 a Realistic Therapeutic for Aging-Dependent Muscle Defects," Cir. Res., 118(7):1143-1150, (Apr. 1, 2016).

Lach-Trifilieff, et al., "An Antibody Blocking Activin Type II Receptors Induces Strong Skeletal Muscle Hypertrophy and Protects from Atrophy," Mol. Cell. Biol. Doi:10.1128/MCB, published online Dec. 2, 2013, pp. 1-40.

Lara-Pezzi, et al., "Abstract 2459: A Potentially Novel Role of the Follistatin-Activing Pathway in Heart Failure and Myocardial Recovery Following Lvad Combination Therapy," Circulation, 116:116:II_541, pp. 1-3, (2007).

Lee, et al., "Regulation of GDF-11 and Myostatin Activity by GASP-1 and GASP-2," PNAS, published online Sep. 9, 2013, pp. E3713-E3722.

Shimano, et al., "Cardiac Myocyte-Specific Ablation of Follistatin-Like 3 Attenuates Stress-Induced Myocardial Hypertrophy," Journal of Biological Chemistry, 286(11):9840-9848, (Mar. 18, 2011).

Tayebati, "Animal Models of Cognitive Dysfunction," Mechanisms of Ageing and Development, 127:100-108, (2006).

Non-Final Office Action for U.S. Appl. No. 15/513,979, dated Mar. 29, 2018.

* cited by examiner

Figure 7

```
>lcl|1497 unnamed protein product
Length=405

Score =  727 bits (1876),  Expect = 0.0, Method: Compositional matrix adjust.
Identities = 359/361 (99%), Positives = 359/361 (99%), Gaps = 0/361 (0%)

Query   47   RSSRPAPSVAPEPDGCPYCVBRQHSRELRLESIRSQILSKLRLKEAPNISREVVKQLLPK   106
             RSSRPAPS  PEPDGCPYCVBRQHSEELRLESIRSQILSKLRLKEAPNISREVVKQLLPK
Sbjct   45   RSSRPAPSAPPEPDGCPYCVBRQHSRELRLESIRSQILSKLRLKEAPNISREVVKQLLPK   104

Query   107  APPLQQIILDLRDFQGDALQPEDFLEEDEYHATTETVISMAQETDPAVQTDGSPLCCHFHF   166
             APPLQQIILDLRDFQGDALQPEDFLEEDEYHATTETVISMAQETDPAVQTDGSPLCCHFHF
Sbjct   105  APPLQQIILDLRDFQGDALQPEDFLEEDEYHATTETVISMAQETDPAVQTDGSPLCCHFHF   164

Query   167  SPKVHFTKYLKAQLWVTLRPYPRPATVYIQILRLKPLTGEGTAGGGGGGRHIRSLKI   226
             SPKVHFTKYLKAQLWVTLRPYPRPATVYIQILRLKPLTGEGTAGGGGGGRHIRSLKI
Sbjct   165  SPKVHFTKYLKAQLWVTLRPYPRPATVYIQILRLKPLTGEGTAGGGGGGRHIRSLKI   224

Query   227  ELHSRSGHBQSIDFKQVLHSBFRQPQSMWGTEINAFDPSGTDLAVTSLGPGAEGLHPPME   286
             ELHSRSGH QSIDFKQVLHSBFRQPQSMWGTEINAFDPSGTDLAVTSLGPGAEGLHPPME
Sbjct   225  ELHSRSGHBQSIDFKQVLHSBFRQPQSMWGTEINAFDPSGTDLAVTSLGPGAEGLHPPME   284

Query   287  LRVLEWTKRSSRHNLGLDCDEHSSESBCCRFFLTVDFEAFGWDWIIAPKDYTANPTCSGQCE   346
             LRVLEWTKRSSRHNLGLDCDEHSSESBCCRFFLTVDFEAFGWDWIIAPKDYTANPTCSGQCE
Sbjct   285  LRVLEWTKRSSRHNLGLDCDEHSSESBCCRFFLTVDFEAFGWDWIIAPKDYTANPTCSGQCE   344

Query   347  YMFMQKYPHTHLVQQANPRGSAGPCCTPTKHSPINMLYFRNDKQQIIYGKIPGMYVDRCGC   406
             YMFMQKYPHTHLVQQANPRGSAGPCCTPTKHSPINMLYFRNDKQQIIYGKIPGMYVDRCGC
Sbjct   345  YMFMQKYPHTHLVQQANPRGSAGPCCTPTKHSPINMLYFRNDKQQIIYGKIPGMYVDRCGC   404

Query   407  S   407
             S
Sbjct   405  S   405
```

Figure 8

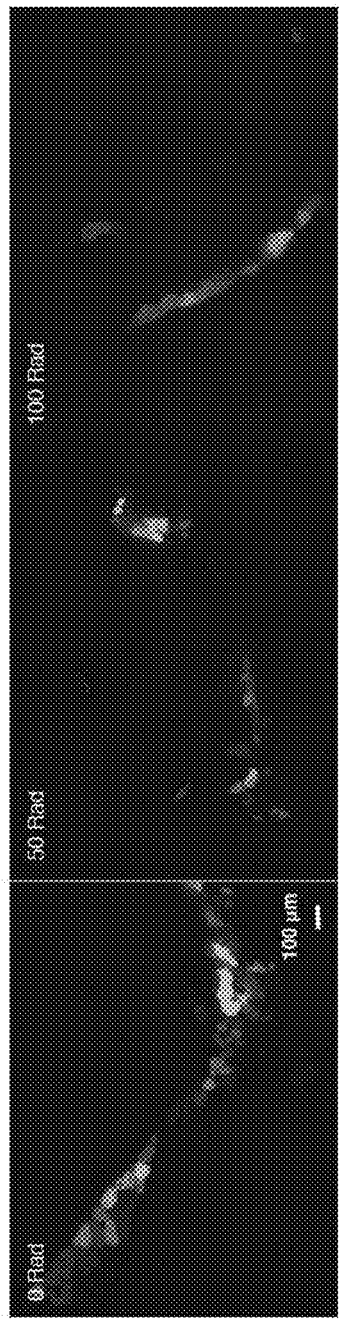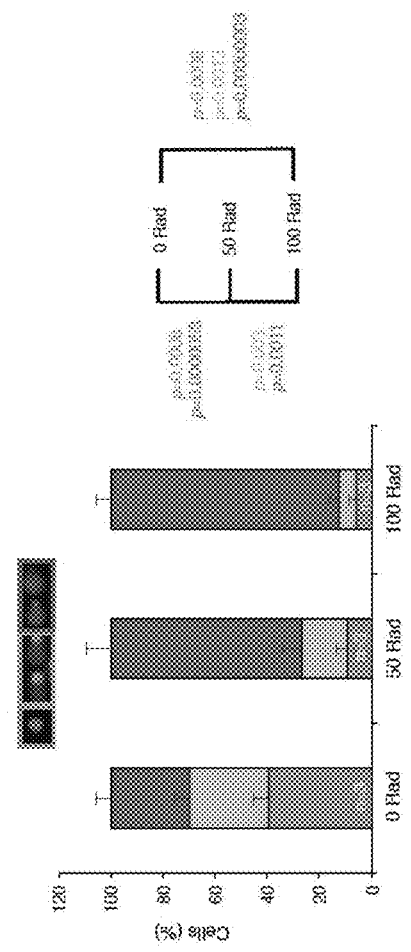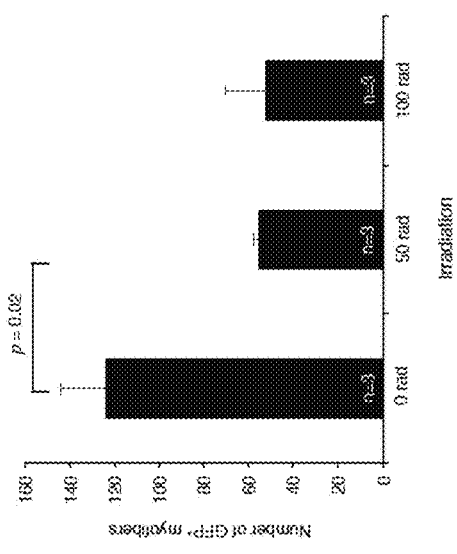
Figure 9

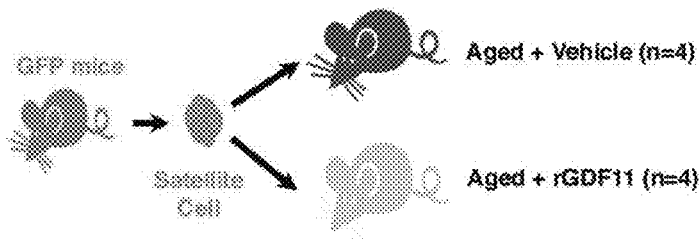
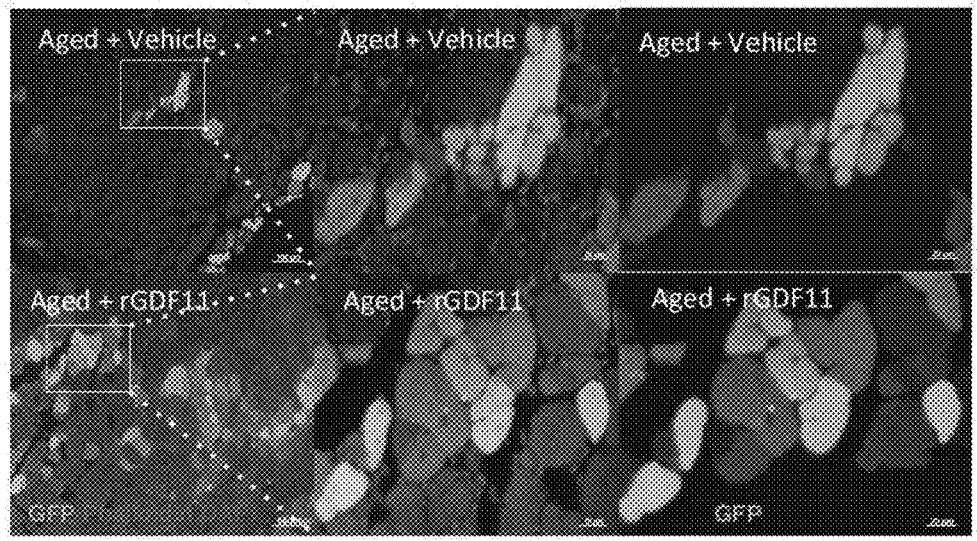
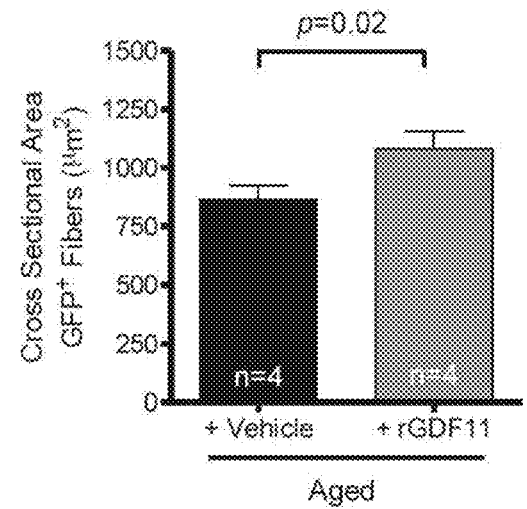
*Figure 16*

A
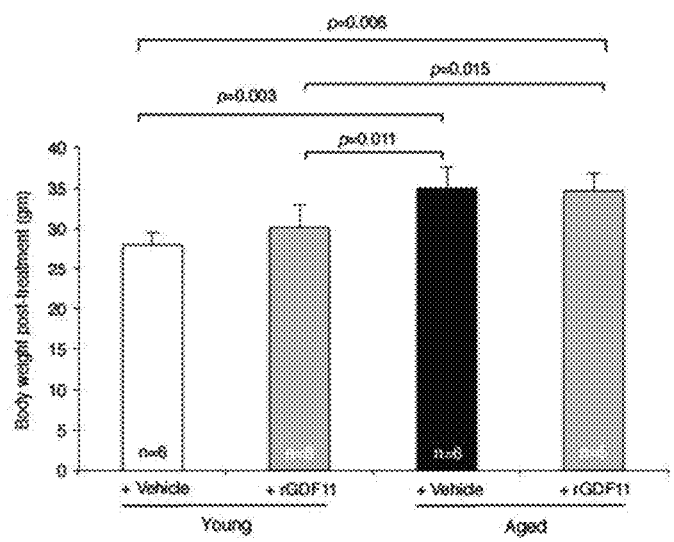
B
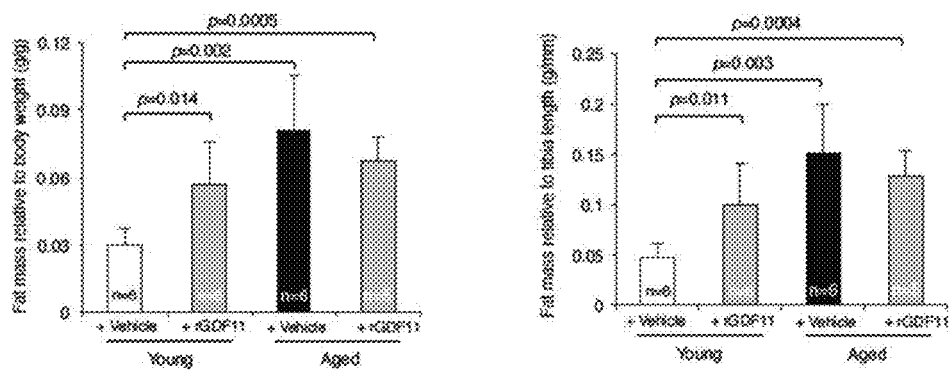
C
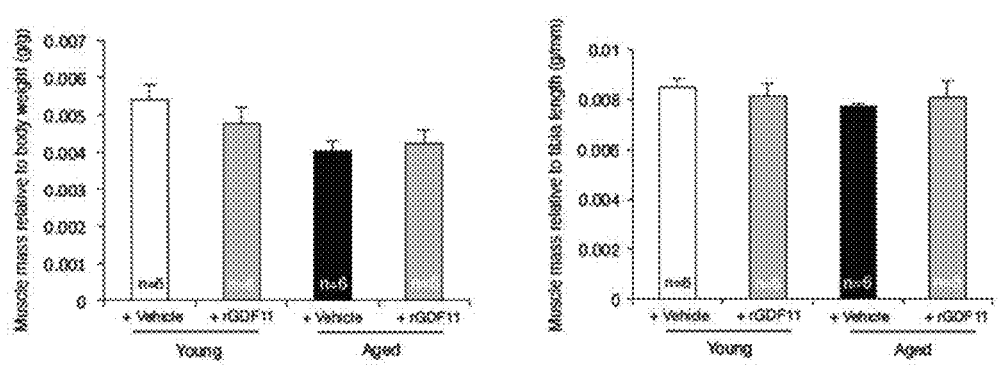
*Figure 17*

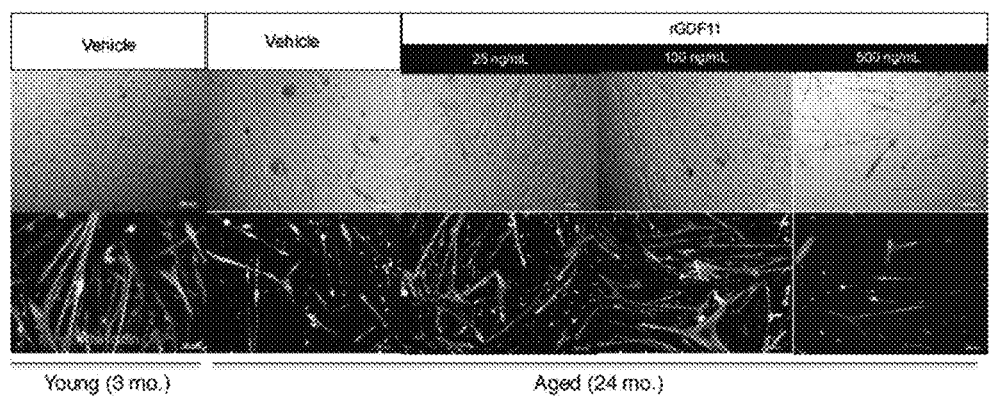
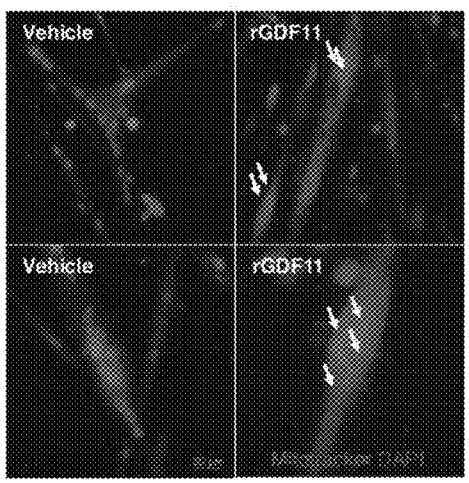 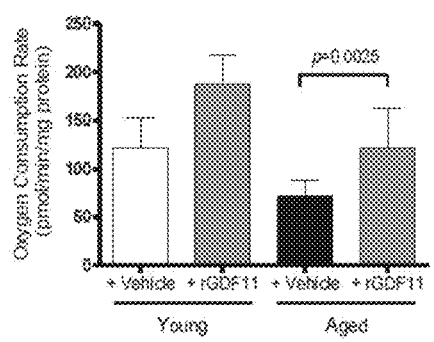
*Figure 20*

METHODS AND COMPOSITIONS FOR REJUVENATING SKELETAL MUSCLE STEM CELLS

RELATED APPLICATIONS

This application is a national stage filing under 35 U.S.C. 371 of International Application No. PCT/US2014/033376, filed Apr. 8, 2014, which claims the benefit of U.S. Provisional Application No. 61/809,784, filed Apr. 8, 2013, the entire teachings of which are incorporated herein by reference. International Application PCT/US2014/033376 was published under PCT Article 21(2) in English.

GOVERNMENT SUPPORT

This invention was made with government support under UO1 HL100402, R01 AG033053, R01 AG032977 and R01 AG040019 awarded by the National Institutes of Health. The government has certain rights in the invention.

BACKGROUND OF THE INVENTION

Age-dependent dysfunction in adult stem cells is attributable to both cell-intrinsic and -extrinsic inputs. Critical mechanisms underlying the functional decline of aged stem cells remain elusive. Accordingly, there exists a need to identify factors that are able to promote or reverse age-associated changes in tissues as diverse as the skeletal muscle, liver and CNS (Wagers and Conboy, Cell 2005; 122, 659; Ruckh et al. Cell Stem Cell 2005; 10, 96).

SUMMARY OF THE INVENTION

The methods and compositions described herein are useful for rejuvenating skeletal muscle stem cells, promoting skeletal muscle regeneration, improving exercise endurance, regenerating skeletal muscle degeneration associated with an age-related disorder of skeletal muscle, and treating, preventing, or reversing skeletal muscle conditions.

In some aspects, the present invention provides a method of rejuvenating skeletal muscle stem cells in a subject in need thereof, comprising administering to the subject a composition which increases the level of GDF11 polypeptide in the subject. In some embodiments, the composition causes the subject's skeletal muscle stem cells to increase in frequency or number, increase the sizes of regenerating myofibers, increase the efficiency of myogenic colony formation, increase the percentage of intact nuclei, and decrease the percentage of severely damaged deoxyribonucleic acid (DNA), thereby rejuvenating the skeletal muscle stem cells in the subject.

In some aspects, the present invention provides a method of promoting skeletal muscle regeneration in a subject in need thereof, comprising administering to the subject a composition which increases the level of GDF11 polypeptide in the subject, wherein the composition causes the subject's skeletal muscle stem cells to increase in frequency or number, increase the sizes of regenerating myofibers, increase the efficiency of myogenic colony formation, increase the percentage of intact nuclei, and decrease the percentage of severely damaged DNA, thereby promoting skeletal muscle regeneration in the subject.

In some aspects, the present invention provides a method of treating or preventing a skeletal muscle condition in a subject in need thereof, comprising administering to the subject an effective amount of a composition which increases the level of GDF11 polypeptide in the subject, wherein the composition causes the subject's skeletal muscle stem cells to increase in frequency or number, increase the sizes of regenerating myofibers, increase the efficiency of myogenic colony formation, increase the percentage of intact nuclei, and decrease the percentage of severely damaged DNA, thereby treating or preventing the skeletal muscle condition in the subject.

In some aspects, the present invention provides a method of treating or preventing sarcopenia in a subject in need thereof, comprising administering to the subject an effective amount of a composition which increases the level of GDF11 polypeptide in the subject, wherein the composition causes the subject's skeletal muscle stem cells to increase in frequency or number, increase the sizes of regenerating myofibers, increase the efficiency of myogenic colony formation, increase the percentage of intact nuclei, and decrease the percentage of severely damaged DNA, thereby treating or preventing sarcopenia in the subject.

In some aspects, the present inventions provide a method of increasing muscle repair in a subject in need thereof, comprising administering to the subject an effective amount of a composition which increases the level of GDF11 polypeptide in the subject, wherein the composition causes skeletal muscle stem cells to increase in frequency or number, increase the sizes of regenerating myofibers, increase the efficiency of myogenic colony formation and increase the percentage of intact nuclei, thereby increasing the muscle repair in the subject.

In some aspects, the present inventions provide a method of increasing mitochondrial biogenesis in a subject, comprising administering to the subject an effective amount of a composition which increases the level of GDF11 polypeptide in the subject, wherein the composition causes improvements of myofibrillar and mitochondrial morphology, a reduction of atypical and swollen mitochondria in the subject, reduced accumulation of vacuoles, and restoration of regular sarcomeric and interfibrillar mitochondrial patterning, thereby increasing the mitochondrial biogenesis in the subject. In certain embodiments, such improvement in mitochondrial function may be associated or comprise an increase in proliferator-activated receptor gamma co-activator 1α (PGC-1α) in the muscles of the subject.

In certain aspects, the present inventions provide a method of enhancing, increasing or restoring satellite cell regenerative function in a subject in need thereof, comprising administering to the subject an effective amount of a composition which increases the level of GDF11 polypeptide in the subject. In certain embodiments, such restoration of satellite cell regenerative functions is accompanied by reversal of accumulated DNA damage in the subject's skeletal muscle stem cells. In other embodiments, such restoration of satellite cell function is accompanies by an increase in the frequency and/or number, an increase in the sizes of regenerating myofibers, an increase the efficiency of myogenic colony formation and/or an increase the percentage of intact nuclei in the subject.

In some embodiments, the present inventions provide a method of increasing the efficiency or robustness of muscle repair in a subject. In other embodiments, the present inventions provide methods of increasing or accelerating the recovery from muscle damage in a subject.

In some aspects, the present inventions provide a method of increasing the strength (e.g., muscle strength) or exercise endurance capacity (e.g., muscle endurance) in a subject in need thereof, comprising administering to the subject a composition which increases the level of GDF11 polypeptide in the subject, thereby increasing the strength or exercise endurance capacity.

In some embodiments, the composition comprises a GDF11 polypeptide. In some embodiments, the composition comprises a GDF11 polypeptide comprising the amino acid sequence of human mature GDF11. In some embodiments, the composition comprises a GDF11 polypeptide comprising the amino acid sequence of the human GDF11 propeptide. In some embodiments, the composition comprises a GDF11 polypeptide comprising the amino acid sequence of the human GDF11 precursor polypeptide. In some embodiments, the composition comprises a GDF11 polypeptide comprising the amino acid sequence of the human GDF11 N-terminal polypeptide.

In some aspects, the present invention provides a pharmaceutical composition comprising a GDF11 polypeptide or a functional fragment or variant thereof, and a pharmaceutically acceptable carrier.

In some aspects, the present invention relates to the use of a composition comprising a GDF11 polypeptide or functional fragment or variant thereof for rejuvenating skeletal muscle stem cells in a subject in need thereof, wherein increased levels of the GDF11 polypeptide or functional fragment or variant thereof in the subject rejuvenate skeletal muscle stem cells in the subject. In some embodiments, the composition causes the subject's skeletal muscle stem cells to increase in frequency or number, increase the sizes of regenerating myofibers, increase the efficiency of myogenic colony formation, increase the percentage of intact nuclei, and decrease the percentage of severely damaged DNA, thereby rejuvenating the skeletal muscle stem cells in the subject.

In some aspects, the present invention relates to the use of a composition comprising a GDF11 polypeptide or a functional fragment or variant thereof for promoting skeletal muscle regeneration in a subject in need thereof, wherein increased levels of the GDF11 polypeptide or functional fragment or variant thereof in the subject cause the subject's skeletal muscle stem cells to increase in frequency or number, increase the sizes of regenerating myofibers, increase the efficiency of myogenic colony formation, increase the percentage of intact nuclei, and decrease the percentage of severely damaged DNA, thereby promoting skeletal muscle regeneration in the subject.

In some aspects, the present invention relates to the use of a composition comprising a GDF11 polypeptide or a functional fragment or variant thereof for treating or preventing a skeletal muscle condition in a subject in need thereof, wherein increased levels of the GDF11 polypeptide or functional fragment or variant thereof cause the subject's skeletal muscle stem cells to increase in frequency or number, increase the sizes of regenerating myofibers, increase the efficiency of myogenic colony formation, increase the percentage of intact nuclei, and decrease the percentage of severely damaged DNA, thereby treating or preventing the skeletal muscle condition in the subject.

In some aspects, the present invention relates to the use of a composition comprising a GDF11 polypeptide or a functional fragment or variant thereof for increasing muscle repair in a subject in need thereof, wherein increased levels of the GDF11 polypeptide or functional fragment or variant thereof causes the subject's skeletal muscle stem cells to increase in frequency or number, to increase the sizes of regenerating myofibers, to increase the efficiency of myogenic colony formation and to increase the percentage of intact nuclei, thereby increasing the muscle repair in the subject.

In some embodiments, the present inventions relate to the use of a composition comprising a GDF11 polypeptide or a functional fragment or variant thereof for increasing satellite cell mitochondrial biogenesis in a subject in need thereof, wherein increasing the level of the GDF11 polypeptide or functional fragment or variant thereof causes improvement of myofibrillar and mitochondrial morphology, a reduction of atypical and swollen mitochondria, reduced accumulation of vacuoles, and restoration of regular sarcomeric and interfibrillar mitochondrial patterning, thereby increasing the mitochondrial biogenesis in the subject.

In some aspects, the present invention relates to the use of a composition comprising a GDF11 polypeptide or a functional fragment or variant thereof for increasing strength (e.g., muscle strength) or exercise endurance capacity (e.g., muscle endurance) in a subject in need thereof, wherein increasing the level or the GDF11 polypeptide or functional fragment or variant thereof causes an increased strength or exercise endurance in the subject.

In some embodiments, the skeletal muscle condition is selected from the group consisting of atrophy, bony fractures associated with muscle wasting or weakness, cachexia, denervation, diabetes, dystrophy, exercise-induced skeletal muscle fatigue, fatigue, frailty, inflammatory myositis, metabolic syndrome, neuromuscular disease, obesity, post-surgical muscle weakness, post-traumatic muscle weakness, sarcopenia, toxin exposure, wasting, and weakness.

In some aspects, the present invention relates to the use of a composition comprising a GDF11 polypeptide or a functional fragment or variant thereof for treating or preventing sarcopenia in a subject in need thereof, wherein increased levels of the GDF11 polypeptide or functional fragment or variant thereof cause the subject's skeletal muscle stem cells to increase in frequency or number, increase the sizes of regenerating myofibers, increase the efficiency of myogenic colony formation, increase the percentage of intact nuclei, and decrease the percentage of severely damaged DNA, thereby treating or preventing sarcopenia in the subject.

In some embodiments, the subject has been diagnosed with a skeletal muscle condition due to aging.

In some embodiments, the composition increases the level of GDF11 polypeptide in the systemic circulation of the subject. In some embodiments, the composition increases the level of GDF11 polypeptide in the skeletal muscle tissue of the subject.

In some embodiments, the composition comprises an isolated or recombinant GDF11 polypeptide.

In some embodiments, the GDF11 polypeptide comprises the amino acid sequence of a human mature GDF11. In some embodiments, the GDF11 polypeptide comprises the amino acid sequence of a human GDF11 pro-peptide. In some embodiments, the GDF11 polypeptide comprises the amino acid sequence of a human GDF11 precursor polypeptide. In some embodiments, the GDF11 polypeptide comprises the amino acid sequence of a human GDF11 N-terminal polypeptide.

In some embodiments, the composition comprises homodimers of GDF11 polypeptides comprising the amino acid sequence of any of a human GDF11 precursor polypeptide, a human GDF11 pro-peptide, a human mature GDF11 or a human GDF11 N-terminal polypeptide. In some embodiments, the composition comprises complexes of GDF11 polypeptides comprising the amino acid sequence of any of a human GDF11 precursor polypeptide, a human GDF11 pro-peptide, a human mature GDF11 or a human GDF11 N-terminal polypeptide.

In some embodiments, the composition comprises a nucleic acid encoding the GDF11 polypeptide or functional fragment or variant thereof.

In some embodiments, the composition is administered via a route selected from the group consisting of intravenously, subcutaneously, intra-arterially, and intra-muscularly.

In some embodiments, the level of GDF11 polypeptide is increased by at least 100%. In some embodiments, the level of GDF11 polypeptide is increased to at least 75% of a healthy reference level.

BRIEF DESCRIPTION OF THE DRAWINGS

FIG. 7 depicts an alignment of human GDF11 precursor polypeptide (query sequence: residues 62-407 of SEQ ID NO: 1) and human GDF8 precursor polypeptide (subject sequence: SEQ ID NO: 2).

FIG. 8 depicts an alignment of human GDF11 precursor peptide (query sequence: residues 47-407 of SEQ ID NO: 1) and murine GDF11 precursor peptide (subject sequence: SEQ ID NO: 3).

FIG. 9 depicts the reduced engraftment of irradiated young GFP+ satellite cells into mdx mice. (A) Representative images of transverse cryosections of TA from mdx recipients that were transplanted with non-irradiated (0 rad) or irradiated (50 or 100 rad) GFP+ satellite cells (from 8-week old male GFP-transgenic donors) by intramuscular injection. (B) Bar graph representing the maximum number of GFP+ fibers per recipient, as analyzed by direct epifluorescence on serial transverse sections. Data are shown as mean±SEM from n=3 animals per group and p-values were calculated using Students t-test. (C) Quantification of alkaline single cell gel electrophoresis assays performed with GFP+ satellite cells used for transplantation, showing increased DNA damage among irradiated cells. Data represents mean±SD from 3 experimental replicates. Color coded visual scoring key of DNA damage assays and p-values, indicating only statistically significant differences, are shown at top and right.

FIG. 16 illustrates that rGDF11 increases the cross sectional area of engrafted, regenerating fibers in aged muscle. (A) Schematic diagram depicting experimental design. GFP+ satellite cells were sorted from GFP transgenic mice and transplanted into aged recipients (n=4 per group) who were treated with rGDF11 or vehicle alone for 4 weeks prior and 2 weeks following transplantation. (B) Representative images of transverse cryosections of tibialis anterior (TA) muscle harvested 2 weeks after transplantation with 30,000 double-sorted GFP+ satellite cells isolated from young mice (4-6 weeks of age). Satellite cells were injected into the TA muscles of vehicle- (top) or rGDF11 (bottom)-treated aged mice, which were pre-injured by cardiotoxin injection 1 day prior to satellite cell transplantation. Muscles were analyzed for GFP expression by direct epifluorescence at 40× magnification. (C) Quantification of myofiber cross-sectional area for newly regenerated GFP+ fibers (shown in B). Data represent mean±SD and p-value was calculated by Student's t-test.

FIG. 17 illustrates that no detectable alterations in bodyweight, fat-mass or muscle-mass after rGDF11 supplementation in young or aged animals. (A) Bar graph representation of body weight in grams after 30 days of vehicle- or rGDF11-treatment in young or aged male mice. All mice were housed and treated in the same facility. (B) Bar graph representation of fat-mass normalized to body weight (left panel) or tibia length (right panel) as indicated. Fat-mass represents sum of excised white fat pads at inguinal, gonadal and axillary locations of both sides of each animal. (C) Bar graph representation of muscle-mass normalized to body weight (left panel) or tibia length (right panel) as indicated. Muscle mass represents a sum of TA and EDL muscle-mass of both hind limbs of each animal. Number of animals used for analysis is shown within each bar as "n=". Data represents mean±SD. p-values, calculated by Students t-test, are shown only for statistically significant differences.

FIG. 20 shows that rGDF11 promotes myogenic differentiation and mitochondrial function in vitro. (A) Representative brightfield (top) or immunofluorescence (bottom) images of satellite cells harvested from young (3 mo.) or aged mice, proliferated with vehicle (control) or rGDF11 at the concentration indicated for 5 days in growth media followed by differentiation media for 5 days (young) or 7 days (aged). Cells were stained after culture to identify nuclei (DAPI, blue), cellular actin (Phalloidin, green), and myosin heavy chain (MyHC, red). Cultures of aged satellite cells exposed to rGDF11 at 25 or 100 ng/mL showed enhanced myogenic differentiation. (B) Representative immunofluorescence images of Mitotracker™ stained myotubes, differentiated in the presence of vehicle alone or 100 ng/ml rGDF11. Mitotracker is a mitochondrial membrane potential dependent dye and arrows indicate puncta of mitochondria in differentiated myotubes. (C) Bar graph of basal oxygen consumption rate (OCR) in Seahorse metabolic flux assays of young or aged satellite cells differentiated for 7 days in the presence of vehicle alone or of 100 ng/ml rGDF11. Cells exposed to rGDF11 show increased Mitotracker staining and increased OCR, indicative of enhanced mitochondrial content and bioenergetics. Data represents average of 5 technical replicates±SD and only significant p-values are shown, calculated using Student's t-test.

DETAILED DESCRIPTION OF THE INVENTION

Figure 1:
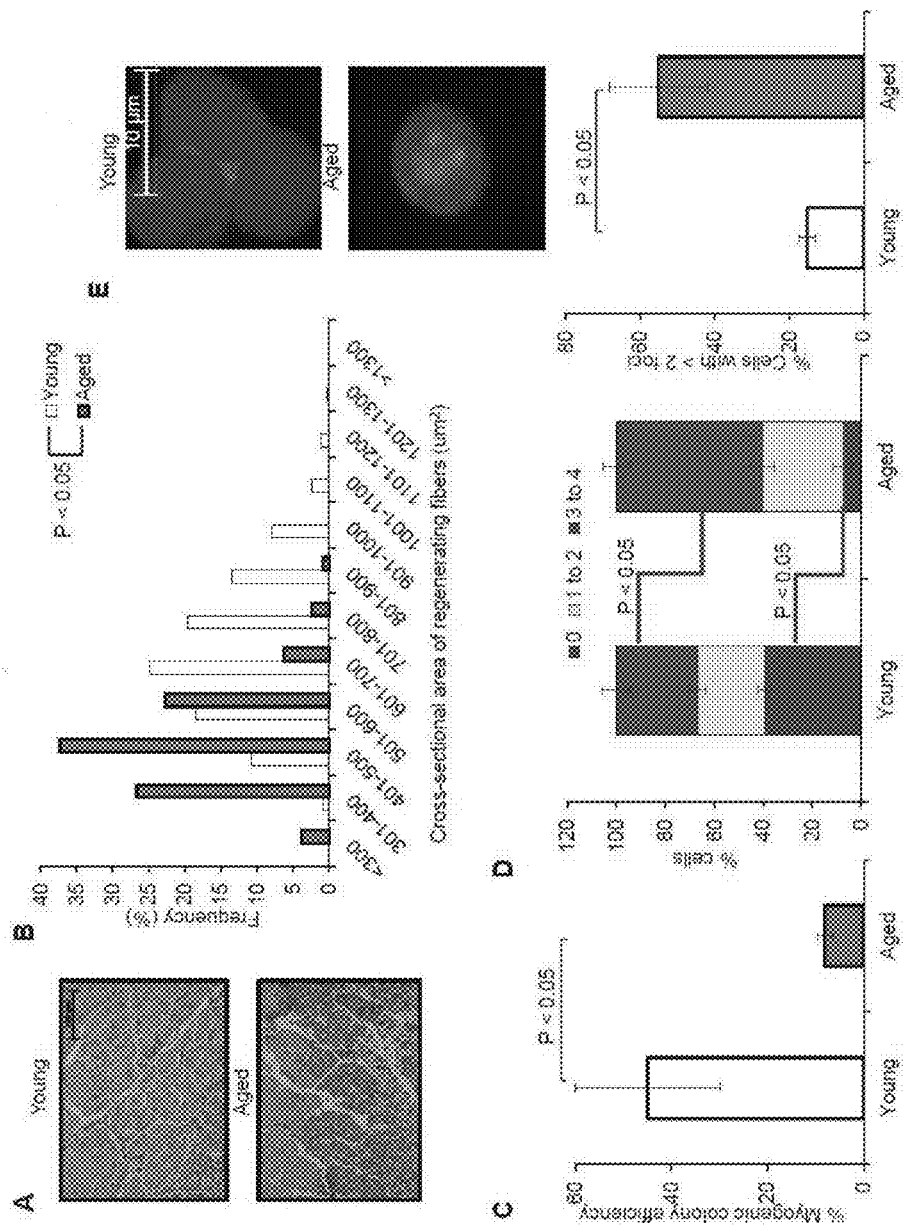
FIG. 1 shows age-dependent alterations in function of aged muscle stem cells. (A) Representative images of regenerating tibialis anterior (TA) muscle cross-sections stained by H&E on day 7 after cryoinjury of young or aged mice. (B) Frequency distribution of myofiber size in regenerating muscle (day 7 after cryoinjury) of young or aged mice. (C) Myogenic colony forming efficiency of satellite cells isolated from young (white column) or aged (black column) mice. (D) Quantification of DNA damage in freshly isolated satellite cells from young or aged mice by alkaline comet assays. Different colors represent different scores of comets as indicated (see also FIG. 4). (E) Representative immunofluorescence images of phosphorylated H2AX foci (green) in freshly isolated satellite cells from young or aged mice. (100× magnification, nuclei stained with DAPI (blue)). Quantification is shown below. All graphs represent mean+/−standard deviations from 5-8 independent experiments. Student's t-test was performed for statistical analysis in C, D and E. Step-down Bonferroni method was used for statistical analysis in B.

Described herein are methods and compositions based on the discovery that as animals age, the level of GDF11 polypeptide in their blood decreases and results in diminished regenerative potential of skeletal muscle due to deterioration of skeletal muscle stem cells. The methods and compositions described herein are useful for rejuvenating skeletal muscle stem cells, promoting skeletal muscle regeneration, improving exercise endurance, and regenerating skeletal muscle degeneration associated with an age-related disorder of skeletal muscle. The methods and compositions described herein generally relate to increasing the level of GDF11 polypeptide in a subject to treat, prevent, or reverse the skeletal muscle conditions described herein.

For convenience, certain terms employed herein, in the specification, examples and appended claims are collected here. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs.

As used herein, "skeletal muscle condition" refers to a condition in skeletal muscle mediated or characterized by a reduction in circulating GDF11 polypeptide in a subject. Non-limiting examples of skeletal muscle conditions include atrophy, bony fractures associated with muscle wasting or weakness, cachexia, denervation, diabetes, dystrophy, exercise-induced skeletal muscle fatigue, fatigue, frailty, inflammatory myositis, metabolic syndrome, neuromuscular disease, obesity, post-surgical muscle weakness, post-traumatic muscle weakness, sarcopenia, toxin exposure, wasting, and weakness As used herein, "frailty" is a syndrome characterized by meeting at least one of the following five attributes: unintentional weight loss, muscle weakness, slow walking speed, exhaustion, and low physical activity.

As used herein, "cachexia" means a state often associated with cancer or other serious diseases or conditions, (e.g., chronic obstructive pulmonary disease, chronic kidney disease), that is characterized by progressive weight loss, muscle atrophy and fatigue, due to the deletion of adipose tissue and skeletal muscle.

As used herein, "post-surgical muscle weakness" refers to a reduction in the strength of one or more muscles following surgical procedure. Weakness may be generalized (i.e., total body weakness) or localized to a specific area, side of the body, limb, or muscle.

As used herein, "post-traumatic muscle weakness" refers to a reduction in the strength of one or more muscles following a traumatic episode (e.g., bodily injury). Weakness may be generalized (e.g., total body weakness) or localized to a specific area, side of the body, limb, or muscle.

As used herein, "neuromuscular disease" means any disease or condition that affects any part of the nerve and muscle. Neuromuscular disease encompasses critical illness polyneuropathy, prolonged neuromuscular blockade, acute myopathy as well as acute inflammatory demyelinating polyradiculoneuropathy, amyotrophic lateral sclerosis (ALS), autonomic neuropathy, Charcot-Marie-Tooth disease and other hereditary motor and sensory neuropathies, chronic inflammatory demyelinating polyradiculoneuropathy, dermatomyositis/polymyositis, diabetic neuropathy, dystrophinopathies, endocrine myopathies, focal muscular atrophies, hemifacial spasm, hereditary neuropathies of the Charcot-Marie-Tooth disease type, inclusion body myositis, Kennedy disease, Lambert-Eaton myasthenic syndrome, muscular dystrophy (e.g., limb-girdle, Duchenne, Becker, myotonic, facioscapulohumeral, etc.), metabolic myopathies, metabolic neuropathy, multifocal motor neuropathy with conduction blocks, myasthenia gravis, neuropathy of Friedreich Ataxia, neuropathy of leprosy, nutritional neuropathy, periodic paralyses, primary lateral sclerosis, restrictive lung disease, sarcoidosis and neuropathy, Schwartz-Jampel Syndrome, spinal muscular atrophy (SMA), stiff person syndrome, thyroid disease, traumatic peripheral nerve lesions, vasculitic neuropathy, among others.

As used herein, "sarcopenia" means a loss of skeletal muscle mass, quality, and strength. Often sarcopenia is associated with aging, but may also occur in association with HIV infection and a variety of chronic conditions. Sarcopenia may lead to frailty, for example, in the elderly. Sacropenia also encompasses a condition or symptom associated with sacropenia including, but not limited to loss of skeletal muscle mass, muscle weakness, fatigue, disability, and morbidity.

The terms "decrease," "reduce," "reduced," "reduction," "decrease," and "inhibit" are all used herein generally to mean a decrease by a statistically significant amount relative to a reference. However, for avoidance of doubt, "reduce," "reduction" or "decrease" or "inhibit" typically means a decrease by at least 10% as compared to a reference level and can include, for example, a decrease by at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, up to and including, for example, the complete absence of the given entity or parameter as compared to the reference level, or any decrease between 10-99% as compared to the absence of a given treatment.

The terms "increased," "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90%, or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or more as compared to a reference level.

The term "isolated" or "partially purified" as used herein refers, in the case of a nucleic acid or polypeptide, to a nucleic acid or polypeptide separated from at least one other component (e.g., nucleic acid or polypeptide) that is present with the nucleic acid or polypeptide as found in its natural source and/or that would be present with the nucleic acid or polypeptide when expressed by a cell, or secreted in the case of secreted polypeptides. A chemically synthesized nucleic acid or polypeptide or one synthesized using in vitro transcription/translation is considered "isolated."

The term "biological sample" as used herein denotes a sample taken or isolated from a biological organism, e.g., skeletal muscle sample, blood sample, cell lysate, a homogenate of a tissue sample from a subject, or a fluid sample from a subject. Exemplary biological samples include, but are not limited to, skeletal muscle tissue biopsies or blood and/or serum samples. In some embodiments, the sample is from a resection, biopsy, or core needle biopsy. In addition, fine needle aspirate samples can be used. Samples can include paraffin-embedded and frozen tissue. The term "biological sample" also includes untreated or pretreated (or pre-processed) biological samples. In some embodiments, the biological sample is an untreated biological sample. The sample can be obtained by removing a sample of cells from a subject, but can also be accomplished by using previously isolated cells (e.g. isolated at a prior time point and isolated by the same or another person).

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments, the subject is a mammal, e.g., a primate, e.g., a human. The terms, "patient", "individual" and "subject" are used interchangeably herein. Preferably, the subject is a mammal. The mammal can be a human, non-human primate, mouse, rat, dog, cat, horse, or cow, but are not limited to these examples. Mammals other than humans can be advantageously used, for example, as subjects that represent animal models of, for example, sarcopenia. In addition, the methods described herein can be used to treat domesticated animals and/or pets. A subject can be male or female. A subject can be one who has been previously diagnosed with or identified as suffering from or having a condition in need of treatment (e.g., a skeletal muscle condition, e.g., sarcopenia) or one or more complications related to such a condition, and optionally, but need not have already undergone treatment for a condition or the one or more complications related to the condition. Alternatively, a subject can also be one who has not been previously diagnosed as having a condition in need of treatment or one or more complications related to such a condition. Rather, a subject can include one who exhibits one or more risk factors for a condition or one or more complications related to a condition. A "subject in need" of treatment for a particular condition can be a subject having that condition, diagnosed as having that condition, or at increased risk of developing that condition relative to a given reference population.

As used herein the term "comprising" or "comprises" is used in reference to compositions, methods, and respective component(s) thereof, that are essential to the method or composition, yet open to the inclusion of unspecified elements, whether essential or not.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment.

The term "statistically significant" or "significantly" refers to statistical significance and generally means a p value greater than 0.05 (calculated by the relevant statistical test). Those skilled in the art will readily appreciate that the relevant statistical test for any particular experiment depends on the type of data being analyzed. Additional definitions are provided in the text of individual sections below.

Definitions of common terms in cell biology and molecular biology can be found in "The Merck Manual of Diagnosis and Therapy", 19th Edition, published by Merck Research Laboratories, 2006 (ISBN 0-911910-19-0); Robert S. Porter et al. (eds.), The Encyclopedia of Molecular Biology, published by Blackwell Science Ltd., 1994 (ISBN 0-632-02182-9); The ELISA guidebook (Methods in molecular biology 149) by Crowther J. R. (2000); Immunology by Werner Luttmann, published by Elsevier, 2006. Definitions of common terms in molecular biology can also be found in Benjamin Lewin, Genes X, published by Jones & Bartlett Publishing, 2009 (ISBN-10: 0763766321); Kendrew et al. (eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

Unless otherwise stated, the present invention was performed using standard procedures, as described, for example in Sambrook et al., Molecular Cloning: A Laboratory Manual (3 ed.), Cold Spring Harbor Laboratory Press, Cold Spring Harbor, N.Y., USA (2001) and Davis et al., Basic Methods in Molecular Biology, Elsevier Science Publishing, Inc., New York, USA (1995) which are both incorporated by reference herein in their entireties.

Described herein are methods comprising administering to a subject a composition which increases the level of GDF11 polypeptide in the subject. In some embodiments, the subject is one who has, or has been diagnosed as having a skeletal muscle condition due to aging. As used herein, a "skeletal muscle condition" due to aging refers to a skeletal muscle condition described herein which is attributable to a subject's age. In some embodiments, the subject is one who is at risk of developing a skeletal muscle condition due to aging. In some embodiments, the subject is an elderly subject. In some embodiments, an elderly subject is over the age of 50, 55, 60, 65, 70, 75, 80, 85, 90, or 100 years.

In some embodiments, the composition which increases the level of GDF11 polypeptide is administered to a subject who has or has been diagnosed with a neuromuscular disease described herein.

In some embodiments, the level of GDF11 polypeptide is the level of GDF11 in the circulation of a subject. In some embodiments, the level of GDF11 polypeptide is the level of GDF11 in the skeletal muscle tissue of a subject. In some embodiments, the level of GDF11 polypeptide is determined by measuring the level of an mRNA encoding a GDF11 polypeptide. The level of GDF11 in a subject can be determined by obtaining a biological sample from the subject and determining the level of GDF11 in the biological sample. Methods for determining the level of a polypeptide in a subject or a sample obtained from a subject are well known in the art and include, but are not limited to, ELISA, radioimmunoassay, immunohistochemistry, methods involving a labeled antibody specific for GDF11, dot blot analysis, functional bioassays, Northern blot, in-situ hybridization, and RT-PCR, aptamer-based proteomic technology (e.g., SOMAscan™ commercially available from SomaLogic, Inc.) among others. Antibodies specific for GDF11 are commercially available, (e.g. Cat. No. ab71347 from Abcam: Cambridge, Mass.). In some embodiments, the antibodies are antibodies which do not cross-react with GDF8. In some embodiments, the antibodies are selective GDF11 monoclonal antibodies. In some embodiments, the level of GDF11 can be measured as described in Souza et al., Molecular Endocrinology 2008 22:2689-2702; which is incorporated by reference herein in its entirety.

As animals age, skeletal muscle often atrophies and experiences diminished regenerative potential due to deterioration of skeletal muscle stem cells, which is often accompanied by one or more skeletal muscle conditions (e.g., sarcopenia). Without wishing to be bound by theory, it is believed that deterioration of skeletal muscle stem cells and characteristic attendant reduced skeletal muscle mass results in part from decreased levels of circulating GDF11 polypeptide. Whereas work described previously by the inventors showed that cardiac hypertrophy or enlargement of the cardiac muscle due to aging correlated with decreased levels of circulating GDF11 polypeptide, the work described herein demonstrates that decreased levels of circulating GDF11 polypeptide results in diminished skeletal muscle regenerative potential due to deterioration of skeletal muscle stem cells. In previous work, the inventors found that increasing levels of circulating GDF11 polypeptide in a subject effectively reversed cardiac hypertrophy and actually shrunk cardiac tissue. In contrast, the work described herein surprisingly and unexpectedly demonstrates that GDF11 polypeptide rejuvenates skeletal muscle stem cells and actually enlarges skeletal muscle, thereby improving the regenerative potential of skeletal muscle.

Surprisingly, the work described herein demonstrates that aged mice treated in vivo with daily IP injection of recombinant GDF11 (rGDF11) caused the subjects' skeletal muscle stem cells to increase in frequency or number, increase regenerating myofibers size, increase the efficiency of myogenic colony formation, increase the percentage of intact muscle stem cell nuclei, and decrease the percentage of severely damaged deoxyribonucleic acid (DNA) (i.e., treatment with rGDF11 rejuvenated the subject's skeletal muscle stem cells). In particular, the rGDF11 treatment altered the distribution sizes of regenerating fibers cross-sectional area from about 300-700 μm to about 400-1000 μm (FIG. 3B), increased the frequency of skeletal muscle stem cells (e.g., increased presence of regenerative cells) in aged muscles by between about 33% to 66% (FIG. 3C), increased myogenic colony formation efficiency by about 2 fold (FIG. 3D), increased the percentage of intact nuclei (green bars, FIG. 3E), decreased the percentage of aged skeletal muscle stem cells with severely damaged DNA by 4 fold (red bars, FIG. 3E).

Accordingly, in one aspect, the present invention provides a method of rejuvenating skeletal muscle stem cells in a subject in need thereof, comprising administering to the subject a composition which increases the level of GDF11 polypeptide in the subject. In some embodiments, the composition causes the subject's skeletal muscle stem cells to increase in frequency or number, increases the sizes of regenerating myofibers, increases the efficiency of myogenic colony formation, increases the percentage of intact muscle stem cell nuclei, and decreases the percentage of severely damaged deoxyribonucleic acid (DNA), thereby rejuvenating the skeletal muscle stem cells in the subject.

In another aspect, the present invention provides a method of promoting skeletal muscle regeneration in a subject in need thereof, comprising administering to the subject a composition which increases the level of GDF11 polypeptide in the subject, wherein the composition causes the subject's skeletal muscle stem cells to increase in frequency or number, increases the sizes of regenerating myofibers, increases the efficiency of myogenic colony formation, increases the percentage of intact nuclei, and decreases the percentage of severely damaged DNA, thereby promoting skeletal muscle regeneration in the subject.

The methods and compositions described herein relate to increasing the level of GDF11 polypeptide in a subject. As used herein, "GDF11" refers to "Growth and Differentiation Factor 11" (NCBI Gene ID No: 10220), a member of the Transforming Growth Factor-beta superfamily of growth factors. GDF11 is known to bind TGFβ3 superfamily type I receptors including ALK4, ALK5, and ALK7. For signaling in mammalian development, GDF11 predominantly uses ALK4 and ALK5. In some embodiments, GDF11 signaling can also occur via the ACVR2B receptor. GDF11 is also closely related to GDF8 (also known as myostatin). GDF11 can also be referred to as bone morphogenic protein 11 or BMP11. As used herein, "GDF11" can include the human precursor polypeptide (SEQ ID NO: 1, NCBI Ref Seq: NP 005802); the human pro-peptide; the human N-terminal polypeptide; and the human mature forms of GDF11 as well as homologs from other species, including but not limited to bovine, dog, cat, chicken, murine, rat, porcine, bovine, turkey, horse, fish, baboon and other primates. The terms also refer to fragments or variants of GDF11 that maintain at least 50% of the skeletal muscle stem cell rejuvenating effect of the full length GDF11 of a human GDF11 pro-peptide, a human GDF11 precursor polypeptide, or a human mature GDF11, e.g. as measured in an appropriate animal model (e.g., heterochronic parabiosis of aged mice).

Conservative substitution variants that maintain the skeletal muscle stem cell rejuvenating effect of wild type GDF11 will include a conservative substitution as defined herein. The identification of amino acids most likely to be tolerant of conservative substitution while maintaining at least 50% of the activity of the wild type GDF11 is guided by, for example, sequence alignment with GDF11 homologs or paralogs from other species. Amino acids that are identical between GDF11 homologs are less likely to tolerate change, while those showing conservative differences are obviously much more likely to tolerate conservative change in the context of an artificial variant. Similarly, positions with non-conservative differences are less likely to be critical to function and more likely to tolerate conservative substitution in an artificial variant. Variants can be tested for activity, for example, by administering the variant to an appropriate animal model (e.g., cryoinjured aged mice to induce post-injury regeneration).

For human GDF11, the pro-peptide plus signal sequence (e.g. the precursor polypeptide) is 407 amino acids long. Cleavage of the 24 amino acid signal peptide generates a pro-peptide of 383 amino acids and cleavage of the pro-peptide results in a mature GDF11 polypeptide of 109 amino acids that corresponds to the C-terminal 109 amino acids of the pro-peptide. The mature polypeptide forms a disulfide-linked homodimer. Cleavage of the pro-peptide also generates the N-terminal polypeptide comprising amino acids 25-298 of a human GDF11 precursor polypeptide (SEQ ID NO: 1). The N-terminal GDF11 polypeptide can antagonize the activity of, e.g., the polypeptides of the human GDF11 pro-peptide and human mature GDF11, at least in vitro by forming a complex with other forms of GDF11 polypeptides and can thus be used to modulate the activity of GDF11 compositions as described herein. Thus, to the extent that GDF11 polypeptides as described herein rejuvenate skeletal muscle stem cells or promote skeletal muscle regeneration, and to the extent the N-terminal GDF11 polypeptide can antagonize such effects, the human GDF11 N-terminal polypeptide can be excluded from the meaning of "GDF11 polypeptide" as that term is used herein.

As used herein, the terms "proteins" and "polypeptides" are used interchangeably to designate a series of amino acid residues connected to the other by peptide bonds between the alpha-amino and carboxy groups of adjacent residues. The terms "protein", and "polypeptide" refer to a polymer of protein amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when refining to a gene product and fragments thereof.

Thus, exemplary polypeptides or proteins include gene products, naturally occurring proteins, homologs, orthologs, paralogs, fragments and other equivalents, variants, fragments, and analogs of the foregoing.

As used herein, "pro-peptide" used in reference to GDF11 refers to a GDF11 polypeptide in which the signal domain (e.g. amino acids 1-24 of SEQ ID NO: 1) has been cleaved off during formation of the mature and/or active forms of GDF11. As used herein, "precursor peptide" used in reference to a GDF11 polypeptide comprising the signal domain, e.g., a polypeptide comprising the amino acid sequence of a human GDF11 precursor polypeptide (SEQ ID NO: 1).

In some embodiments, the level of GDF11 in a subject is increased by administering a composition comprising a GDF11 polypeptide and/or a nucleic acid encoding a GDF11 polypeptide. A GDF11 polypeptide administered to a subject according to the methods described herein can comprise a GDF11 polypeptide as described herein above, e.g. a pro-peptide or mature form. In some embodiments, the GDF11 polypeptide comprises the amino acid sequence of a human GDF11 precursor polypeptide (SEQ ID NO: 1). In some embodiments, the GDF11 polypeptide comprises the amino acid sequence of the human GDF11 pro-peptide. In some embodiments, the GDF11 polypeptide comprises the amino acid sequence of human mature GDF11. In some embodiments, the GDF11 polypeptide comprises the amino acid sequence of the human GDF11 N-terminal polypeptide.

In some embodiments, the composition administered to the subject can comprise GDF11 polypeptide homodimers comprising polypeptides of the amino acid sequence of a human mature GDF11. In some embodiments, the composition administered to the subject can comprise GDF11 polypeptide homodimers comprising polypeptides of the amino acid sequence of the human GDF11 N-terminal polypeptide. In some embodiments, the composition administered to the subject can comprise GDF11 polypeptide homodimers comprising polypeptides of the amino acid sequence of a human GDF11 pro-peptide. In some embodiments, the composition administered to the subject can comprise GDF11 polypeptide homodimers comprising polypeptides of the amino acid sequence of a human GDF11 precursor polypeptide (SEQ ID NO: 1). In some embodiments, the composition administered to the subject can comprise GDF11 polypeptide heterodimers comprising polypeptides of any of the amino acid sequence of a human GDF11 N-terminal polypeptide, human mature GDF11, a human GDF11 pro-peptide, and/or a human GDF11 precursor polypeptide (SEQ ID NO: 1).

In some embodiments, a variant or fragment of a GDF11 polypeptide can be administered to a subject. In some embodiments, the variant of GDF11 is a conservatively modified variant. In some embodiments of any of the aspects described herein, the subject can be administered a variant or fragment (e.g. a conservatively modified variant or a functional fragment or a nucleic acid encoding such a polypeptide) of a polypeptide selected from Collectin kidney 1 (e.g. NCBI Gene ID No: 78989), Cathespin D (e.g. NCBI Gene ID No: 1509), Dickkopf-related protein 4 (e.g. NCBI Gene ID No: 27121), Erythrocyte membrane protein 4.1 (e.g. NCBI Gene ID No: 2035), esterase D (e.g. NCBI Gene ID No: 2098), hemoglobin (e.g. NCBI Gene ID No: 3043 or 3047), interleukin-1 receptor accessory protein (e.g. NCBI Gene ID No: 3556), natural killer group 2 member D (e.g. NCBI Gene ID No: 22914), Ras-related C3 botulinum toxin substrate 1 (e.g. NCBI Gene ID No: 5879), GTP-binding nuclear protein Ran (e.g. NCBI Gene ID No: 5901), tissue inhibitor of metalloproteases 3 (e.g. NCBI Gene ID No: 7078), and thymidylate synthase (e.g. NCBI Gene ID No: 7298).

In some embodiments, the GDF11 polypeptide can be a variant of a sequence described herein, e.g. a variant of a GDF11 polypeptide comprising the amino acid sequence of a human GDF11 N-terminal polypeptide, a human mature GDF11, a human GDF11 precursor polypeptide (SEQ ID NO: 1), or a human GDF11 pro-peptide. In some embodiments, the variant is a conservative substitution variant. Variants can be obtained by mutations of native nucleotide sequences, for example. A "variant," as referred to herein, is a polypeptide substantially homologous to a native or reference polypeptide, but which has an amino acid sequence different from that of the native or reference polypeptide because of one or a plurality of deletions, insertions or substitutions. Polypeptide-encoding DNA sequences encompass sequences that comprise one or more additions, deletions, or substitutions of nucleotides when compared to a native or reference DNA sequence, but that encodes a variant protein or fragment thereof that retains the relevant biological activity relative to the reference protein, e.g., can rejuvenate skeletal muscle stem cells at least 50% as well as wild type GDF11. As to amino acid sequences, one of skill will recognize that individual substitutions, deletions or additions to a nucleic acid, peptide, polypeptide, or protein sequence which alters a single amino acid or a small percentage, (e.g., 5% or fewer, e.g. 4% or fewer, or 3% or fewer, or 1% or fewer) of amino acids in the encoded sequence is a "conservatively modified variant" where the alteration results in the substitution of an amino acid with a chemically similar amino acid. It is contemplated that some changes can potentially improve the relevant activity, such that a variant, whether conservative or not, has more than 100% of the activity of wild type GDF11, e.g. 110%, 125%, 150%, 175%, 200%, 500%, 1000% or more.

Figure 7:
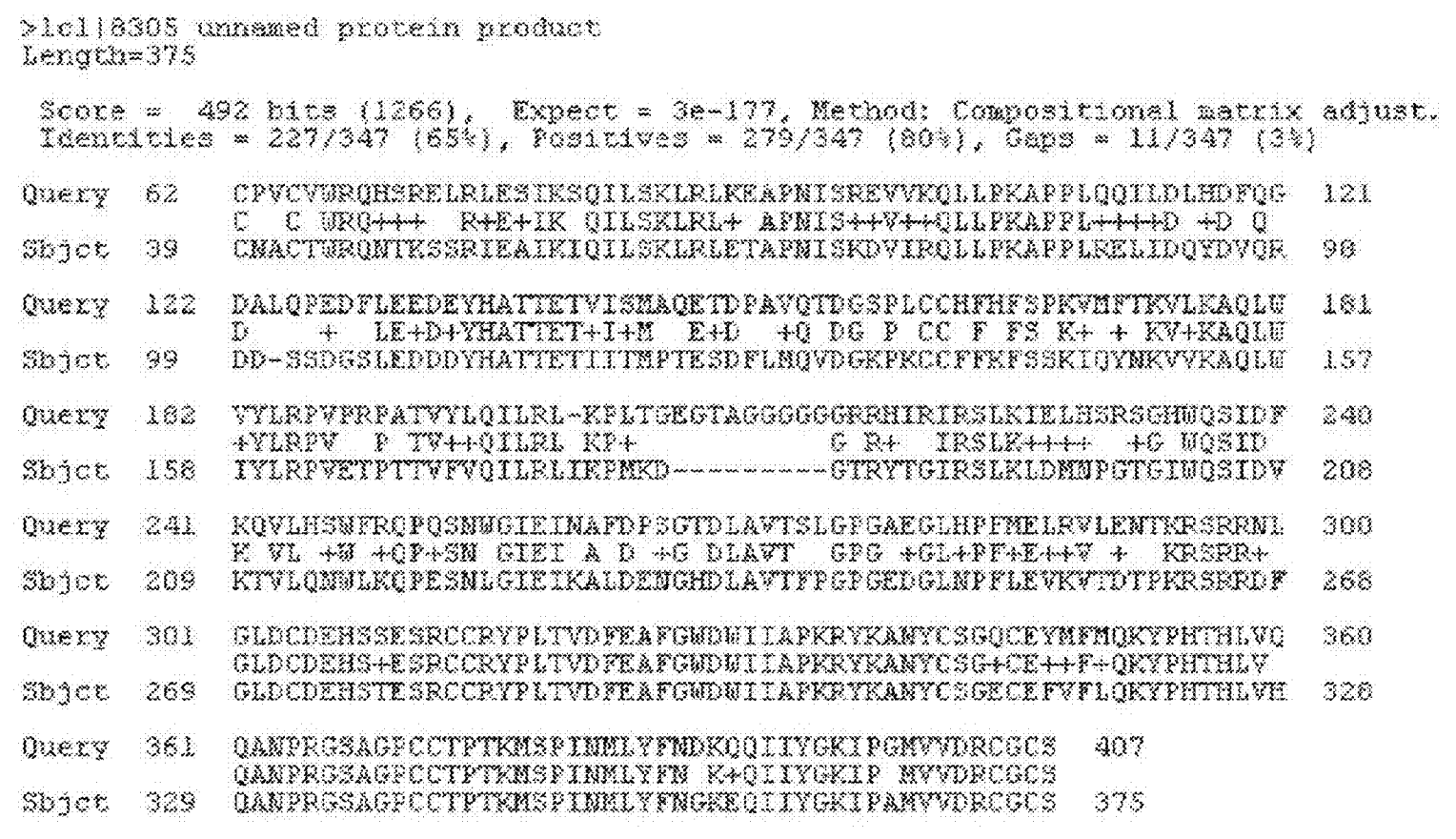

One method of identifying amino acid residues which can be substituted is to align, for example, human GDF11 to a GDF11 homolog from one or more non-human species. Alignment can provide guidance regarding not only residues likely to be necessary for function but also, conversely, those residues likely to tolerate change. Where, for example, an alignment shows two identical or similar amino acids at corresponding positions, it is more likely that that site is important functionally. Where, conversely, alignment shows residues in corresponding positions to differ significantly in size, charge, hydrophobicity, etc., it is more likely that that site can tolerate variation in a functional polypeptide. Similarly, alignment with a related polypeptide from the same species, e.g. GDF8, which does not show the same activity, can also provide guidance with respect to regions or structures required for GDF11 activity. FIG. 7 depicts an example of an alignment between human GDF11 precursor peptide (query sequence; residues 62-407 of SEQ ID NO: 1) and human GDF8 precursor peptide (SEQ ID NO: 2) created using the default settings of the alignment tool of the BLASTP program, freely available on the world wide web at http://blast.ncbi.nlm.nih.gov/. FIG. 8 depicts an example of an alignment between human GDF11 precursor peptide (query sequence; residues 47-407 of SEQ ID NO: 1) and murine GDF11 precursor peptide (SEQ ID NO: 3) created using the default settings of the alignment tool of the BLASTP program, freely available on the world wide web at http://blast.ncbi.nlm.nih.gov/. The variant amino acid or DNA sequence can be at least 90%, at least 95%, at least 96%, at least 97%, at least 98%, at least 99%, or more, identical to a native or reference sequence, e.g. a human GDF11 N-terminal polypeptide, a human mature GDF11, a human GDF11 precursor polypeptide (SEQ ID NO: 1), or human GDF11 pro-peptide or a nucleic acid encoding one of those amino acid sequences. The degree of homology (percent identity) between a native and a mutant sequence can be determined, for example, by comparing the two sequences using freely available computer programs commonly employed for this purpose on the World Wide Web. The variant amino acid or DNA sequence can be at least 90%, at least 91%, at least 92%, at least 93%, at least 94%, at least 95%, at least 96%, at least 97%, at least 98%, at least 99%, or more, similar to the sequence from which it is derived (referred to herein as an "original" sequence). The degree of similarity (percent similarity) between an original and a mutant sequence can be determined, for example, by using a similarity matrix. Similarity matrices are well known in the art and a number of tools for comparing two sequences using similarity matrices are freely available online, e.g. BLASTp (available on the world wide web at http://blast.ncbi.nlm.nih.gov), with default parameters set.

It is noted that the mature GDF11 polypeptide includes likely intrachain disulfide bonds between, e.g. amino acid 313 and 372; 341 and 404; and 345 and 406 (numbered relative to the full length polypeptide, including the signal sequence) and that amino acid 371 likely participates in interchain disulfide bonding.

A given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are well known. Polypeptides comprising conservative amino acid substitutions can be tested in any one of the assays described herein to confirm that a desired apoptotic activity of a native or reference polypeptide is retained. Conservative substitution tables providing functionally similar amino acids are well known in the art. Such conservatively modified variants are in addition to and do not exclude polymorphic variants, interspecies homologs, and alleles consistent with the disclosure. Typically conservative substitutions for one another include: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

Any cysteine residue not involved in maintaining the proper conformation of the polypeptide also can be substituted, generally with serine, to improve the oxidative stability of the molecule and prevent aberrant crosslinking. Conversely, cysteine bond(s) can be added to the polypeptide to improve its stability or facilitate oligomerization.

In some embodiments, the GDF11 polypeptide administered to a subject can comprise one or more amino acid substitutions or modifications. In some embodiments, the substitutions and/or modifications can prevent or reduce proteolytic degradation and/or prolong half-life of the polypeptide in the subject. In some embodiments, a GDF11 polypeptide can be modified by conjugating or fusing it to other polypeptide or polypeptide domains such as, by way of non-limiting example, transferrin (W006096515A2), albumin (Yeh et al., 1992), growth hormone (US2003104578AA); cellulose (Levy and Shoseyov, 2002); and/or Fc fragments (Ashkenazi and Chamow, 1997). The references in the foregoing paragraph are incorporated by reference herein in their entireties.

In some embodiments, a GDF11 polypeptide as described herein can comprise at least one peptide bond replacement. A single peptide bond or multiple peptide bonds, e.g. 2 bonds, 3 bonds, 4 bonds, 5 bonds, or 6 or more bonds, or all the peptide bonds can be replaced. An isolated peptide as described herein can comprise one type of peptide bond replacement or multiple types of peptide bond replacements, e.g. 2 types, 3 types, 4 types, 5 types, or more types of peptide bond replacements. Non-limiting examples of peptide bond replacements include urea, thiourea, carbamate, sulfonyl urea, trifluoroethylamine, ortho-(aminoalkyl)-phenylacetic acid, para-(aminoalkyl)-phenylacetic acid, meta (aminoalkyl)-phenylacetic acid, thioamide, tetrazole, boronic ester, olefinic group, and derivatives thereof.

In some embodiments, a GDF11 polypeptide as described herein can comprise naturally occurring amino acids commonly found in polypeptides and/or proteins produced by living organisms, e.g. Ala (A), Val (V), Leu (L), Ile (I), Pro (P), Phe (F), Trp (W), Met (M), Gly (G), Ser (S), Thr (T), Cys (C), Tyr (Y), Asn (N), Gln (Q), Asp (D), Glu (E), Lys (K), Arg (R), and His (H). In some embodiments, a GDF11 polypeptide as described herein can comprise alternative amino acids. Non-limiting examples of alternative amino acids include, D-anlino acids; beta-amino acids; homocysteine, phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine (3-mercapto-D-valine), ornithine, citruline, alpha-methyl-alanine, parabenzoylphenylalanine, para-amino phenylalanine, p-fluorophenylalanine, phenylglycine, propargylglycine, sarcosine, and tert-butylglycine), diaminobutyric acid, 7-hydroxytetrahydroisoquinoline carboxylic acid, naphthylalanine, biphenylalanine, cyclohexylalanine, aminoisobutyric acid, norvaline, norleucine, tert-leucine, tetrahydroisoquinoline carboxylic acid, pipecolic acid, phenylglycine, homophenylalanine, cyclohexylglycine, dehydroleucine, 2,2-diethylglycine, 1-amino-1cyclopentanecarboxylic acid, 1-amino-1-cyclohexanecarboxylic acid, amino-benzoic acid, aminonaphthoic acid, gamma-aminobutyric acid, difluorophenylalanine, nipecotic acid, alpha-anlino butyric acid, thienyl-alanine, t-butylglycine, trifluorovaline; hexafluoroleucine; fluorinated analogs; azidemodified amino acids; alkyne-modified amino acids; cyano-modified amino acids; and derivatives thereof.

In some embodiments, a GDF11 polypeptide can be modified, e.g. by addition of a moiety to one or more of the amino acids comprising the peptide. In some embodiments, a GDF11 polypeptide as described herein can comprise one or more moiety molecules, e.g. 1 or more moiety molecules per peptide, 2 or more moiety molecules per peptide, 5 or more moiety molecules per peptide, 10 or more moiety molecules per peptide or more moiety molecules per peptide. In some embodiments, a GDF11 polypeptide as described herein can comprise one more types of modifications and/or moieties, e.g. 1 type of modification, 2 types of modifications, 3 types of modifications or more types of modifications. Non-limiting examples of modifications and/or moieties include PEGylation; glycosylation; HESylation; ELPylation; lipidation; acetylation; amidation; end-capping modifications; cyano groups; phosphorylation; albumin, and cyclization. In some embodiments, an end-capping modification can comprise acetylation at the N-terminus, N-terminal acylation, and N-terminal formylation. In some embodiments, an end-capping modification can comprise amidation at the C terminus, introduction of C-terminal alcohol, aldehyde, ester, and thioester moieties. The half-life of a GDF11 polypeptide can be increased by the addition of moieties, e.g. PEG or albumin.

In some embodiments, the GDF11 polypeptide administered to the subject can be a functional fragment of one of the GDF11 amino acid sequences described herein. As used herein, a "functional fragment" is a fragment or segment of a peptide which can rejuvenate skeletal muscle stem cells in a subject in accordance with the work described herein. A functional fragment can comprise conservative substitutions of the sequences disclosed herein. In some embodiments, a functional fragment can comprise the 12.5 kDa C-terminus of GDF11. In some embodiments, the 12.5 kDa C-terminus of GDF11 can function as a monomer. In some embodiments, the 12.5 kDa C-terminus of GDF11 can function as a homodimer. In some embodiments, the 12.5 kDa C-terminus of GDF11 can function as a heterodimer with the GDF11 pro-peptide.

Alterations of the original amino acid sequence can be accomplished by any of a number of techniques known to one of skill in the art. Mutations can be introduced, for example, at particular loci by synthesizing oligonucleotides containing a mutant sequence, flanked by restriction sites permitting ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required. Techniques for making such alterations include those disclosed by Walder et al. (Gene 42:133, 1986); Bauer et al. (Gene 37:73, 1985); Craik (BioTechniques, January 1985, 12-19); Smith et al. (Genetic Engineering: Principles and Methods, Plenum Press, 1981); and U.S. Pat. Nos. 4,518,584 and 4,737,462, which are herein incorporated by reference in their entireties. In some embodiments, a GDF11 polypeptide as described herein can be chemically synthesized and mutations can be incorporated as part of the chemical synthesis process.

In some embodiments, a GDF11 polypeptide as described herein can be formulated as a pharmaceutically acceptable prodrug. As used herein, a "prodrug" refers to compounds that can be converted via some chemical or physiological process (e.g., enzymatic processes and metabolic hydrolysis) to a therapeutic agent. Thus, the term "prodrug" also refers to a precursor of a biologically active compound that is pharmaceutically acceptable. A prodrug may be inactive when administered to a subject, i.e. an ester, but is converted in vivo to an active compound, for example, by hydrolysis to the free carboxylic acid or free hydroxyl. The prodrug compound often offers advantages of solubility, tissue compatibility or delayed release in an organism. The term "prodrug" is also meant to include any covalently bonded carriers, which release the active compound in vivo when such prodrug is administered to a subject. Prodrugs of an active compound may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a subject, cleaves to form a free hydroxy, free amino or free mercapto group, respectively. Examples of prodrugs include, but are not limited to, acetate, formate and benzoate derivatives of an alcohol or acetamide, formamide and benzamide derivatives of an amine functional group in the active compound and the like. See Harper, "Drug Latentiation" in Jucker, ed. *Progress in Drug Research* 4:221-294 (1962); Morozowich et al, "Application of Physical Organic Principles to Prodrug Design" in E. B. Roche ed. *Design of Biophamzaceutical Properties through Prodrugs and Analogs*, APHA Acad. Pharm. Sci. 40 (1977); *Bioreversible Carriers in Drug in Drug Design, Theory and Application*, E. B. Roche, ed., APHA Acad. Pharm. Sci. (1987); *Design of Prodrugs*, H. Bundgaard, Elsevier (1985); Wang et al. "Prodrug approaches to the improved delivery of peptide drug" in *Curr. Pharm. Design*. 5(4):265-287 (1999); Pauletti et al.

(1997) Improvement in peptide bioavailability: Peptidomimetics and Prodrug Strategies, *Adv. Drug. Delivery Rev.* 27:235-256; Mizen et al. (1998) "The Use of Esters as Prodrugs for Oral Delivery of (3-Lactam antibiotics," *Pharm. Biotech.* 11, 345-365; Gaignault et al. (1996) "Designing Prodrugs and Bioprecursors I. Carrier Prodrugs," *Pract. Med. Chern.* 671-696; Asgharnejad, "Improving Oral Drug Transport", in *Transport Processes in Pharmaceutical Systems*, G. L. Amidon, P. I. Lee and E. M. Topp, Eds., Marcell Dekker, p. 185-218 (2000); Balant et al., "Prodrugs for the improvement of drug absorption via different routes of administration", *Eur. J. Drug Metab. Pharmacokinet.*, 15(2): 143-53 (1990); Balimane and Sinko, "Involvement of multiple transporters in the oral absorption of nucleoside analogues", *Adv. Drug Delivel)' Rev.*, 39(1-3): 183-209 (1999); Browne, "Fosphenytoin (Cerebyx)", *Clin. Neuropharmacol.* 20(1): 1-12 (1997); Bundgaard, "Bioreversible derivatization of drugs-principle and applicability to improve the therapeutic effects of drugs", *Arch. Pharm. Chemi* 86(1): 1-39 (1979); Bundgaard H. "Improved drug delivery by the prodrug approach", *Controlled Drug Delivery* 17: 179-96 (1987); Bundgaard H. "Prodrugs as a means to improve the delivery of peptide drugs", *Arfv. Drug Delivel)' Rev.* 8(1): 1-38 (1992); Fleisher et al. "Improved oral drug delivery: solubility limitations overcome by the use of prodrugs", *Arfv. Drug Delivery Rev.* 19(2): 115-130 (1996); Fleisher et al. "Design of prodrugs for improved gastrointestinal absorption by intestinal enzyme targeting", *Methods Enzymol.* 112 (Drug Enzyme Targeting, Pt. A): 360-81, (1985); Farquhar D, et al., "Biologically Reversible Phosphate-Protective Groups", *Pharm. Sci.*, 72(3): 324-325 (1983); Freeman S, et al., "Bioreversible Protection for the Phospho Group: Chemical Stability and Bioactivation of Di(4-acetoxybenzyl) Methylphosphonate with Carboxyesterase," *Chern. Soc., Chern. Commun.*, 875-877 (1991); Friis and Bundgaard, "Prodrugs of phosphates and phosphonates: Novel lipophilic alphaacyloxyalkyl ester derivatives of phosphate- or phosphonate containing drugs masking the negative charges of these groups", *Eur. J. Pharm. Sci.* 4: 49-59 (1996); Gangwar et al., "Pro-drug, molecular structure and percutaneous delivery", *Des. Biophamz. Prop. Prodrugs Analogs, [Symp.] Meeting Date* 1976, 409-21. (1977); Nathwani and Wood, "Penicillins: a current review of their clinical pharmacology and therapeutic use", *Drugs* 45(6): 866-94 (1993); Sinhababu and Thakker, "Prodrugs of anticancer agents", *Adv. Drug Delivery Rev.* 19(2): 241-273 (1996); Stella et al., "Prodrugs. Do they have advantages in clinical practice?", *Drugs* 29(5): 455-73 (1985); Tan et al. "Development and optimization of anti-HIV nucleoside analogs and prodrugs: A review of their cellular pharmacology, structure-activity relationships and pharmacokinetics", *Adv. Drug Deliva}' Rev.* 39(1-3): 117-151 (1999); Taylor, "Improved passive oral drug delivery via prodrugs", *Adv. Drug Delivery Rev.*, 19(2): 131-148 (1996); Valentino and Borchardt, "Prodrug strategies to enhance the intestinal absorption of peptides", *Drug Discovery Today* 2(4): 148-155 (1997); Wiebe and Knaus, "Concepts for the design of anti-HIV nucleoside prodrugs for treating cephalic HIV infection", *Adv. Drug Delivery Rev.:* 39(1-3):63-80 (1999); Waller et al., "Prodrugs", *Br. J. Clin. Pharmac.* 28: 497-507 (1989), which are incorporated by reference herein in their entireties.

In some embodiments, a GDF11 polypeptide as described herein can be a pharmaceutically acceptable solvate. The term "solvate" refers to a peptide as described herein in the solid state, wherein molecules of a suitable solvent are incorporated in the crystal lattice. A suitable solvent for therapeutic administration is physiologically tolerable at the dosage administered. Examples of suitable solvents for therapeutic administration are ethanol and water. When water is the solvent, the solvate is referred to as a hydrate. In general, solvates are formed by dissolving the compound in the appropriate solvent and isolating the solvate by cooling or using an antisolvent. The solvate is typically dried or azeotroped under ambient conditions.

The peptides of the present invention can be synthesized by using well known methods including recombinant methods and chemical synthesis. Recombinant methods of producing a peptide through the introduction of a vector including nucleic acid encoding the peptide into a suitable host cell is well known in the art, such as is described in Sambrook et al., Molecular Cloning: A Laboratory Manual, 2d Ed, Vols 1 to 8, Cold Spring Harbor, N.Y. (1989); M. W. Pennington and B. M. Dunn, Methods in Molecular Biology: Peptide Synthesis Protocols, Vol 35, Humana Press, Totawa, N.J. (1994), contents of both of which are herein incorporated by reference. Peptides can also be chemically synthesized using methods well known in the art. See for example, Merrifield et al., J. Am. Chem. Soc. 85:2149 (1964); Bodanszky, M., Principles of Peptide Synthesis, Springer-Verlag, New York, N.Y. (1984); Kirnmerlin, T. and Seebach, D. J. Pept. Res. 65:229-260 (2005); Nilsson et al., Annu. Rev. Biophys. Biomol. Struct. (2005) 34:91-118; W. C. Chan and P. D. White (Eds.) Frnoc Solid Phase Peptide Synthesis: A Practical Approach, Oxford University Press, Cary, N.C. (2000); N. L. Benoiton, Chemistry of Peptide Synthesis, CRC Press, Boca Raton, Fla. (2005); J. Jones, Amino Acid and Peptide Synthesis, 2nd Ed, Oxford University Press, Cary, N.C. (2002); and P. Lloyd-Williams, F. Albericio, and E. Giralt, Chemical Approaches to the synthesis of pep tides and proteins, CRC Press, Boca Raton, Fla. (1997), contents of all of which are herein incorporated by reference. Peptide derivatives can also be prepared as described in U.S. Pat. Nos. 4,612,302; 4,853,371; and 4,684,620, and U.S. Pat. App. Pub. No. 2009/0263843, contents of all which are herein incorporated by reference.

In some embodiments, the technology described herein relates to a nucleic acid encoding a GDF11 polypeptide as described herein. As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one strand nucleic acid of a denatured double stranded DNA. Alternatively, it can be a single-stranded nucleic acid not derived from any double stranded DNA. In one aspect, the template nucleic acid is DNA. In another aspect, the template is RNA. Suitable nucleic acid molecules are DNA, including genomic DNA or cDNA. Other suitable nucleic acid molecules are RNA, including mRNA. The nucleic acid molecule can be naturally occurring, as in genomic DNA, or it may be synthetic, i.e., prepared based upon human action, or may be a combination of the two. The nucleic acid molecule can also have certain modification such as 2'-deoxy, 2'-deoxy-2'fluoro, 2'-0-methyl, 2'-0-methoxyethyl (2'-0-MOE), 2'-0-aminopropyl (2'-0-AP), 2'-0-dimethylaminoethyl (2'-O-DMAOE), 2'-0-dimethylaminopropyl (2'-0-DMAP), 2'-0-dimethylaminoethyloxyethyl (2'-0-DMAEOE), or 2'-0-N-methylacetamido (2'-0-NMA), cholesterol addition, and phosphorothioate backbone as described in US Patent Application 20070213292; and certain ribonucleoside that are is linked between the 2'-oxygen and the 4'-carbon atoms with a methylene unit as described in U.S. Pat. No. 6,268,490, wherein both patent and patent application are incorporated hereby reference in their entirety.

In some embodiments, a nucleic acid encoding a GDF11 polypeptide can comprise the nucleotide sequence of GDF11. In some embodiments, a nucleic acid encoding a GDF11 polypeptide as described herein is comprised by a vector. In some of the aspects described herein, a nucleic acid sequence encoding a GDF11 polypeptide as described herein, or any module thereof, is operably linked to a vector. The term "vector," as used herein, refers to a nucleic acid construct designed for delivery to a host cell or for transfer between different host cells. As used herein, a vector can be viral or non-viral. The term "vector" encompasses any genetic element that is capable of replication when associated with the proper control elements and that can transfer gene sequences to cells. A vector can include, but is not limited to, a cloning vector, an expression vector, a plasmid, phage, transposon, cosmid, chromosome, virus, virion, etc.

As used herein, the term "expression vector" refers to a vector that directs expression of an RNA or polypeptide from sequences linked to transcriptional regulatory sequences on the vector. The sequences expressed will often, but not necessarily, be heterologous to the cell. An expression vector may comprise additional elements, for example, the expression vector may have two replication systems, thus allowing it to be maintained in two organisms, for example in human cells for expression and in a prokaryotic host for cloning and amplification. The term "expression" refers to the cellular processes involved in producing RNA and proteins and as appropriate, secreting proteins, including where applicable, but not limited to, for example, transcription, transcript processing, translation and protein folding, modification and processing. "Expression products" include RNA transcribed from a gene, and polypeptides obtained by translation of mRNA transcribed from a gene. The term "gene" means the nucleic acid sequence which is transcribed (DNA) to RNA in vitro or in vivo when operably linked to appropriate regulatory sequences. The gene may or may not include regions preceding and following the coding region, e.g. 5' untranslated (5'UTR) or "leader" sequences and 3' UTR or "trailer" sequences, as well as intervening sequences (introns) between individual coding segments (exons).

As used herein, the term "viral vector" refers to a nucleic acid vector construct that includes at least one element of viral origin and has the capacity to be packaged into a viral vector particle. The viral vector can contain the nucleic acid encoding a GDF11 polypeptide as described herein in place of non-essential viral genes. The vector and/or particle may be utilized for the purpose of transferring any nucleic acids into cells either in vitro or in vivo. Numerous forms of viral vectors are known in the art.

By "recombinant vector" is meant a vector that includes a heterologous nucleic acid sequence, or "transgene" that is capable of expression in vivo. It should be understood that the vectors described herein can, in some embodiments, be combined with other suitable compositions and therapies. In some embodiments, the vector is episomal. The use of a suitable episomal vector provides a means of maintaining the nucleotide of interest in the subject in high copy number extra chromosomal DNA thereby eliminating potential effects of chromosomal integration.

In some embodiments the level of GDF11 in the subject is increased by at least 20% over the level of GDF11 in the subject prior to treatment, e.g. 20% or more, 30% or more, 40% or more, 50% or more, 100% or more, 150% or more, 200% or more, 250% or more, 300% or more, or 350% or more. In some embodiments the level of GDF11 in the subject is increased by at least 100% over the level of GDF11 in the subject prior to treatment. In some embodiments the level of GDF11 in the subject is increased by at least 200% over the level of GDF11 in the subject prior to treatment. In some embodiments the level of GDF11 in the subject is increased by about 250% over the level of GDF11 in the subject prior to treatment. In some embodiments, the level of GDF11 in the subject is increased to at least 50% of a healthy reference level, e.g. 50% or more, 60% or more, 70% or more, 80% or more, 90% or more, or 100% or more of a healthy reference level. In some embodiments, the level of GDF11 in the subject is increased to at least 60% of a healthy reference level. In some embodiments, the level of GDF11 in the subject is increased to at least 75% of a healthy reference level. In some embodiments, the level of GDF11 in the subject is increased to at least 90% of a healthy reference level. A healthy reference level can be the average level of GDF11 in a population of human subjects (e.g., young individuals) not exhibiting any signs or symptoms of skeletal muscle stem cell deterioration, or related conditions.

As used herein, "skeletal muscle stem cell deterioration" refers to a decrease in cell number, a decrease in regenerating myofiber size, a decrease in the efficiency of myogenic colony formation, a decrease in the percentage of intact nucleic, and an increase in the percentage of severely damaged DNA as assessed by a Comet assay, in skeletal muscle stem cells.

In some embodiments, a healthy reference level can be the average level of GDF11 in a population of human subjects not exhibiting any signs or symptoms of skeletal muscle stem cell deterioration, or related conditions and who are under the age of 70. In some embodiments, a healthy reference level can be the average level of GDF11 in a population of human subjects not exhibiting any signs or symptoms of skeletal muscle stem cell deterioration, or related conditions and who are under the age of 65. In some embodiments, a healthy reference level can be the average level of GDF11 in a population of human subjects not exhibiting any signs or symptoms of skeletal muscle stem cell deterioration, or related conditions and who are under the age of 60. In some embodiments, a healthy reference level can be the average level of GDF11 in a population of human subjects not exhibiting any signs or symptoms of skeletal muscle stem cell deterioration, or related conditions and who are under the age of 55. In some embodiments, a healthy reference level can be the average level of GDF11 in a population of human subjects not exhibiting any signs or symptoms of skeletal muscle stem cell deterioration, or related conditions and who are under the age of 50. In some embodiments, a healthy reference level can be the average level of GDF11 in a population of human subjects not exhibiting any signs or symptoms of skeletal muscle stem cell deterioration, or related conditions and who are under the age of 45. In some embodiments, a healthy reference level can be the average level of GDF11 in a population of human subjects not exhibiting any signs or symptoms of skeletal muscle stem cell deterioration, or related conditions and who are under the age of 40. In some embodiments, a healthy reference level can be the average level of GDF11 in a population of human subjects not exhibiting any signs or symptoms of skeletal muscle stem cell deterioration, or related conditions and who are under the age of 35. In some embodiments, a healthy reference level can be the average level of GDF11 in a population of human subjects not exhibiting any signs or symptoms of skeletal muscle stem cell deterioration, or related conditions and who are under the age of 30. In some embodiments, a healthy reference level can be the average level of GDF11 in a population of human subjects not exhibiting any signs or symptoms of skeletal muscle stem cell deterioration, or related conditions and who are under the age of 25. In some embodiments, a healthy reference level can be the average level of GDF11 in a population of human subjects not exhibiting any signs or symptoms of skeletal muscle stem cell deterioration, or related conditions and who are under the age of 20.

In some embodiments, the methods described herein can comprise selecting a subject with a level of GDF11 which is lower than a healthy reference level and administering a treatment as described herein.

In some embodiments, the level of GDF11 in a subject is increased in order to treat a skeletal muscle condition (e.g. sarcopenia or a sarcopenia associated condition or symptom as described herein). In some embodiments, the level of GDF11 in a subject is increased in order to prevent a skeletal muscle condition (e.g., sarcopenia or a sarcopenia associated condition or symptom as described herein).

Skeletal muscle conditions related to low or decreased GDF11 polypeptide tend to develop with the decrease in GDF11 levels that occur with increasing age. Thus, it is expected that such conditions can be prevented or, at a minimum, delayed, by maintaining GDF11 polypeptide levels at or near the level found in normal, healthy young adults (e.g., by administering a GDF11 polypeptide or a nucleic acid encoding a GDF11 polypeptide with advancing age, but prior to the onset of a skeletal muscle condition).

In another aspect, the present invention provides a method of treating or preventing a skeletal muscle condition in a subject in need thereof, comprising administering to the subject an effective amount of a composition which increases the level of GDF11 polypeptide in the subject, wherein the composition causes the subject's skeletal muscle stem cells to increase in frequency or number, increase the sizes of regenerating myofibers, increase the efficiency of myogenic colony formation, increase the percentage of intact nuclei, and decrease the percentage of severely damaged DNA, thereby treating or preventing the skeletal muscle condition. In some embodiments, the skeletal muscle condition is selected from the group consisting of atrophy, bony fractures associated with muscle wasting or weakness, cachexia, denervation, diabetes, dystrophy, exercise-induced skeletal muscle fatigue, fatigue, frailty, inflammatory myositis, metabolic syndrome, neuromuscular disease, obesity, post-surgical muscle weakness, post-traumatic muscle weakness, sarcopenia, toxin exposure, wasting, and weakness.

Class I sarcopenia has been defined as an appendicular lean body mass index (ALBMI)<or=6.44 kg·m(−2) (appendicular lean body mass/height) (Messier V, Karelis A D, Lavoie M E, Brochu M, Faraj M, Strychar I, Rabasa-Lhoret R. Metabolic profile and quality of life in class I sarcopenic overweight and obese postmenopausal women: a MONET study. Appl Physiol Nutr Metab. 2009 February; 34(1):18-24.) This definition requires scanning of the legs and/or arms to determine muscle bulk. It has also been argued that these scans may not be necessary and that sarcopenia can be defined by measuring anthropometric measurements like arm muscle circumference and calf circumference to determine a below normal amount of limb skeletal muscle (Bauer J M, Kaiser M J, Sieber C C. Sarcopenia in nursing home residents. J Am Med Dir Assoc. 2008 October; 9(8):545-51). A working definition has been given which identifies sarcopenia when skeletal muscle mass in an older subject is more than 2 standard deviations below the mean for healthy younger adults (Baumgartner R N, Koehler K M, Gallagher D, et al (April 1998). "Epidemiology of sarcopenia among the elderly in New Mexico". Am. J. Epidemiol. 147 (8): 755-63).

The compositions and methods described herein are useful for treating or preventing sarcopenia or a condition or symptom associated with sarcopenia (e.g., loss of skeletal muscle mass associated with sarcopenia; fatigue associated with sarcopenia; disability associated with sarcopenia; morbidity associated with sarcopenia; muscle weakness associated with sarcopenia) or to increase the strength of skeletal muscle in sarcopenia or to reduce the risk of bony fractures in a patient with sarcopenia; or for the prevention or treatment of muscle wasting associated with aging; muscle weakness associated with muscle wasting associated with aging; disuse atrophy; muscle weakness associated with disuse atrophy; or for the prevention or secondary prevention of bony fractures associated with muscle wasting or weakness associated with aging or sarcopenia.

Accordingly, in still another aspect, the present invention provides a method of treating or preventing sarcopenia in a subject in need thereof, comprising administering to the subject an effective amount of a composition which increases the level of GDF11 polypeptide in the subject, wherein the composition causes the subject's skeletal muscle stem cells to increase in frequency or number, increase the sizes of regenerating myofibers, increase the efficiency of myogenic colony formation, increase the percentage of intact nuclei, and decrease the percentage of severely damaged DNA, thereby treating or preventing sarcopenia in the subject.

Aspects of the technology described herein relate to compositions comprising a GDF11 polypeptide as described herein or a nucleic acid encoding a GDF11 polypeptide as described herein. In some embodiments, the composition is a pharmaceutical composition. As used herein, the term "pharmaceutical composition" refers to the active agent in combination with a pharmaceutically acceptable carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

In some aspects, a composition described herein comprising a GDF11 polypeptide or functional fragment or variant thereof can be used for rejuvenating skeletal muscle stem cells in a subject in need thereof, wherein increased levels of the GDF11 polypeptide or functional fragment or variant thereof in the subject rejuvenate skeletal muscle stem cells in the subject. In some embodiments, the composition causes the subject's skeletal muscle stem cells to increase in frequency or number, increase the sizes of regenerating myofibers, increase the efficiency of myogenic colony formation, increase the percentage of intact nuclei, and decrease the percentage of severely damaged DNA, thereby rejuvenating the skeletal muscle stem cells in the subject.

In some aspects, a composition described herein comprising a GDF11 polypeptide or a functional fragment or variant thereof can be used for promoting skeletal muscle regeneration in a subject in need thereof, wherein increased levels of the GDF11 polypeptide or functional fragment or variant thereof in the subject cause the subject's skeletal muscle stem cells to increase in frequency or number, increase the sizes of regenerating myofibers, increase the efficiency of myogenic colony formation, increase the percentage of intact nuclei, and decrease the percentage of severely damaged DNA, thereby promoting skeletal muscle regeneration in the subject.

In some aspects, a composition described herein comprising a GDF11 polypeptide or a functional fragment or variant thereof can be used for treating or preventing a skeletal muscle condition in a subject in need thereof, wherein increased levels of the GDF11 polypeptide or functional fragment or variant thereof cause the subject's skeletal muscle stem cells to increase in frequency or number, increase the sizes of regenerating myofibers, increase the efficiency of myogenic colony formation, increase the percentage of intact nuclei, and decrease the percentage of severely damaged DNA, thereby treating or preventing the skeletal muscle condition in the subject. In some embodiments, the skeletal muscle condition is selected from the group consisting of atrophy, bony fractures associated with muscle wasting or weakness, cachexia, denervation, diabetes, dystrophy, exercise-induced skeletal muscle fatigue, fatigue, frailty, inflammatory myositis, metabolic syndrome, neuromuscular disease, obesity, post-surgical muscle weakness, post-traumatic muscle weakness, sarcopenia, toxin exposure, wasting, and weakness.

In some aspects, a composition comprising a GDF11 polypeptide or a functional fragment or variant thereof can be used for treating or preventing sarcopenia in a subject in need thereof, wherein increased levels of the GDF11 polypeptide or functional fragment or variant thereof cause the subject's skeletal muscle stem cells to increase in frequency or number, increase the sizes of regenerating myofibers, increase the efficiency of myogenic colony formation, increase the percentage of intact nuclei, and decrease the percentage of severely damaged DNA, thereby treating or preventing sarcopenia in the subject.

In some embodiments of this and other aspects described herein, the subject has been diagnosed with a skeletal muscle condition due to aging.

A still further aspect of the invention provides a pharmaceutical composition or kit of parts according to the invention for use in treating or preventing sarcopenia or loss of skeletal muscle mass associated with sarcopenia; fatigue associated with sarcopenia; disability associated with sarcopenia; morbidity associated with sarcopenia; muscle weakness associated with sarcopenia; or to increase the strength of skeletal muscle in sarcopenia or to reduce the risk of bony fractures in a patient with sarcopenia; or for the prevention or treatment of muscle wasting associated with ageing; muscle weakness associated with muscle wasting associated with ageing; disuse atrophy; muscle weakness associated with disuse atrophy; or for the prevention or secondary prevention of bony fractures associated with muscle wasting or weakness associated with ageing or sarcopenia.

The preparation of a pharmacological composition that contains active ingredients dissolved or dispersed therein is well understood in the art and generally need not be limited based on formulation. Typically such compositions are prepared as injectable either as liquid solutions or suspensions, however, solid forms suitable for solution, or suspension, in liquid prior to use can also be prepared. The preparation can also be emulsified or presented as a liposome composition. The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents, and the like which enhance the effectiveness of the active ingredient. The therapeutic composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic, and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine, and the like. Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline.

Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active agent used in the invention that will be effective in the treatment of a particular disorder or condition will depend on the nature of the disorder or condition, and can be determined by standard clinical techniques.

In some embodiments, a GDF11 polypeptide or nucleic acid encoding a GDF11 polypeptide as described herein can be administered by controlled- or delayed-release means. Controlled release pharmaceutical products have a common goal of improving drug therapy over that achieved by their non-controlled release counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. Kim, Chemg-ju, Controlled-release Dosage Form Design, 2 (Technomic Publishing, Lancaster, Pa.: 2000).

Conventional dosage forms generally provide rapid or immediate drug release from the formulation. Depending on the pharmacology and pharmacokinetics of the drug, use of conventional dosage forms can lead to wide fluctuations in the concentrations of the drug in a patient's blood and other tissues. These fluctuations can impact a number of parameters, such as dose frequency, onset of action, duration of efficacy, maintenance of therapeutic blood levels, toxicity, side effects, and the like.

Advantageously, controlled-release formulations can be used to control a drug's onset of action, duration of action, plasma levels within the therapeutic window, and peak blood levels. In particular, controlled or extended-release dosage forms or formulations can be used to ensure that the maximum effectiveness of a drug is achieved while minimizing potential adverse effects and safety concerns, which can occur both from under-dosing a drug (i.e., going below the minimum therapeutic levels) as well as exceeding the toxicity level for the drug.

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, ionic strength, osmotic pressure, temperature, enzymes, water, and other physiological conditions or compounds.

A variety of known controlled- or extended-release dosage forms, formulations, and devices can be adapted for use with the salts and compositions of the disclosure. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185 B 1; each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), or a combination thereof to provide the desired release profile in varying proportions.

In some embodiments, the technology described herein relates to a syringe comprising a therapeutically effective amount of a composition e.g. a pharmaceutical preparation comprising a GDF11 polypeptide as described herein.

As used herein, the phrase "therapeutically effective amount", "effective amount" or "effective dose" refers to an amount that provides a therapeutic or aesthetic benefit in the treatment, prevention, or management of, for example, sarcopenia, e.g. an amount that provides a statistically significant decrease in at least one symptom, sign, or marker of sarcopenia.

Determination of a therapeutically effective amount is well within the capability of those skilled in the art. Generally, a therapeutically effective amount can vary with the subject's history, age, condition, sex, as well as the severity and type of the medical condition in the subject, and administration of other pharmaceutically active agents.

In one aspect, the technology described herein relates to a method comprising administering a GDF11 polypeptide or a nucleic acid encoding a GDF11 polypeptide to a subject. In some embodiments, the subject is in need of treatment for a skeletal muscle condition, or a related condition as described herein. In some embodiments, the method is a method of treating a subject. In some embodiments, the method is a method of treating or preventing sarcopenia in a subject. Such conditions are described herein.

As used herein, "treat," "treatment," "treating," or "amelioration" when used in reference to a disease, disorder or medical condition, refer to therapeutic treatments for a condition, wherein the object is to reverse, alleviate, ameliorate, inhibit, slow down or stop the progression or severity of a symptom or condition. The term "treating" includes reducing or alleviating at least one adverse effect or symptom of a condition. Treatment is generally "effective" if one or more symptoms or clinical markers are reduced. Alternatively, treatment is "effective" if the progression of a condition is reduced or halted. That is, "treatment" includes not just the improvement of symptoms or markers, but also a cessation or at least slowing of progress or worsening of symptoms that would be expected in the absence of treatment. Beneficial or desired clinical results include, but are not limited to, alleviation of one or more symptom(s), diminishment of extent of the deficit, stabilized (i.e., not worsening) state of, for example, sarcopenia, delay or slowing of sarcopenia, and an increased lifespan as compared to that expected in the absence of treatment.

As used herein, the term "administering," refers to the placement of the composition comprising a GDF11 polypeptide or a nucleic acid encoding a GDF11 polypeptide as disclosed herein into a subject by a method or route which results in delivery to a site of action. The pharmaceutical composition comprising a GDF11 polypeptide or a nucleic acid encoding a GDF11 polypeptide can be administered by any appropriate route which results in an effective treatment in the subject.

Data described herein indicate that systemic administration via the vascular system can be effective. Thus administration via the intravenous route is specifically contemplated. However, with appropriate formulation, other routes are contemplated, including, for example, intranasally, intraarterially; intra-coronary arterially; orally, by inhalation, intraperitoneally, intramuscularly, subcutaneously, intracavity, or by other means known by those skilled in the art. The compositions are administered in a manner compatible with the dosage formulation, and in a therapeutically effective amount. The quantity to be administered and timing depends on the subject to be treated, capacity of the subject's system to utilize the active ingredient, and degree of therapeutic effect desired.

Therapeutic compositions containing at least one agent can be conventionally administered in a unit dose, for example. The term "unit dose" when used in reference to a therapeutic composition refers to physically discrete units suitable as unitary dosage for the subject, each unit containing a predetermined quantity of active material calculated to produce the desired therapeutic effect in association with the required physiologically acceptable diluent, i.e., carrier, or vehicle.

The dosage ranges for the agent depends upon the potency, and are amounts large enough to produce the desired effect e.g., rejuvenation of a subject's skeletal muscle stem cells or a reversal of a skeletal muscle condition (e.g., sarcopenia). The dosage should not be so large as to cause unacceptable adverse side effects.

Generally, the dosage will vary with the age, condition, and sex of the patient and can be determined by one of skill in the art. The dosage can also be adjusted by the individual physician in the event of any complication. Typically, the dosage can range from 0.001 mg/kg body weight to 0.5 mg/kg body weight. In one embodiment, the dose range is from 5 µg/kg body weight to 30 µg/kg body weight.

Administration of the doses recited above can be repeated. In some embodiments, the doses are given once a day, or multiple times a day, for example, but not limited to, three times a day. In some embodiments, the doses recited above are administered daily for weeks or months. The duration of treatment depends upon the subject's clinical progress and responsiveness to therapy. Without wishing to be bound by theory, where the GDF11 polypeptide apparently diminishes with age in affected individuals, it is expected that long-term therapy would be required to establish and maintain the benefit of GDF11-based treatment, e.g. a skeletal muscle condition, such as sarcopenia.

Precise amounts of active ingredient required to be administered depend on the judgment of the practitioner and are particular to each individual. However, suitable dosage ranges for systemic application are disclosed herein and depend on the route of administration. Suitable regimes for administration are also variable, but are typified by an initial administration followed by repeated doses at one or more intervals by a subsequent administration. Alternatively, continuous intravenous infusion sufficient to maintain concentrations in the blood in the ranges specified for in vivo therapies are contemplated. In some embodiments, the dosage range is sufficient to maintain concentrations in the blood in the range found in the blood of a population of normal, healthy human subjects (e.g. those with no signs, symptoms, or makers of skeletal muscle stem cell deterioration) under the age of 50. In some embodiments, the dosage range is sufficient to maintain concentrations in the blood in the range found in normal, healthy human subjects under the age of 40. In some embodiments, the dosage range is sufficient to maintain concentrations in the blood in the range found in normal, healthy human subjects under the age of 30.

A therapeutically effective amount is an amount of an agent that is sufficient to produce a statistically significant, measurable change in, for example, a skeletal muscle condition (e.g., sarcopenia). Such effective amounts can be gauged in clinical trials as well as animal studies. Efficacy of an agent can be determined by assessing physical indicators of, for example skeletal muscle stem cell deterioration as described above herein. In experimental systems, assays for efficacy include measurement of skeletal muscle mass as well as, determination of myofiber size as determined by histological microscopy, and/or a reduction in expression of aged skeletal muscle stem cell marker such as immunoreactivity for the phosphorylated form of the variant histone H2AX (pH2AX). Such assays are well known in the art and described in detail in the Examples herein. Clinically acceptable methods for detecting or monitoring skeletal muscle stem cell rejuvenation are described herein. In addition, efficacy of an agent can be measured by an increase in GDF11 polypeptides or fragments thereof in a subject being treated with an agent comprising a GDF11 polypeptide or a nucleic acid encoding GDF11 polypeptide.

The efficacy of a given treatment for a skeletal muscle condition (e.g., sarcopenia) can be determined by the skilled clinician. However, a treatment is considered "effective treatment," as the term is used herein, if any one or all of the signs or symptoms of e.g., a skeletal muscle condition are altered in a beneficial manner, other clinically accepted symptoms are improved or ameliorated, e.g., by at least 10% following treatment with an agent as described herein. Efficacy can also be measured by a failure of an individual to worsen as assessed by hospitalization or need for medical interventions (i.e., progression of the disease is halted). Methods of measuring these indicators are known to those of skill in the art and/or described herein.

In some embodiments, the methods further comprise administering the pharmaceutical composition described herein along with one or more additional agents, biologics, drugs, or treatments beneficial to a subject suffering from skeletal muscle stem cell deterioration or a skeletal muscle condition as part of a combinatorial therapy. In some such embodiments, the agent, biologic, drug, or treatment can be selected from the group consisting of: modulators of one or more of skeletal myosin, skeletal actin, skeletal tropomyosin, skeletal troponin C, skeletal troponin I, skeletal troponin T, and skeletal muscle, including fragments and isoforms thereof, and the skeletal sarcomere and other suitable therapeutic agents useful in the treatment of the aforementioned diseases including: anti-obesity agents, anti-sarcopenia agents, anti-wasting syndrome agents, anti-frailty agents, anti-cachexia agents, anti-muscle spasm agents, agents against post-surgical and post-traumatic muscle weakness, and anti-neuromuscular disease agents, as well as the agents described in U.S. Patent Application No. 2005/0197367.

Suitable additional medicinal and pharmaceutical agents include, for example: orlistat, sibramine, diethylpropion, phentermine, benzaphetamine, phendimetrazine, estrogen, estradiol, levonorgestrel, norethindrone acetate, estradiol valerate, ethinyl estradiol, norgestimate, conjugated estrogens, esterified estrogens, medroxyprogesterone acetate, insulin-derived growth factor, human growth hormone, riluzole, cannabidiol, prednisone, beta agonists (e.g., albuterol), myostatin inhibitors, selective androgen receptor modulators, non-steroidal anti-inflammatory drugs, and botulinum toxin.

Other suitable medicinal and pharmaceutical agents include TRH, diethylstilbesterol, theophylline, enkephalins, E series prostaglandins, compounds disclosed in U.S. Pat. No. 3,239,345 (e.g., zeranol), compounds disclosed in U.S. Pat. No. 4,036,979 (e.g., sulbenox), peptides disclosed in U.S. Pat. No. 4,411,890 growth hormone secretagogues such as GHRP-6, GHRP-1 (disclosed in U.S. Pat. No. 4,411,890 and publications WO 89/07110 and WO 89/07111), GHRP-2 (disclosed in WO 93/04081), NN703 (Novo Nordisk), LY444711 Lilly), MK-677 (Merck), CP424391 (Pfizer) and B-HT920, growth hormone releasing factor and its analogs, growth hormone and its analogs and somatomedins including IGF-1 and IGF-2, leukemia inhibitory factor, cilia neurotrophic factor, brain derived neurotrophic factor, interleukin 6, interleukin 15, alpha-adrenergic agonists, such as clonidine or serotonin 5-$HT_D$ agonists, such as sumatriptan, agents which inhibit somatostatin or its release, such as physostigmine, pyridostigmine, parathyroid hormone, PTH (1-34), and bisphosphonates, such as MK-217 (alendronate).

Still other suitable medicinal and pharmaceutical agents include estrogen, testosterone, selective estrogen receptor modulators, such as tamoxifen or raloxifene, other androgen receptor modulators, such as those disclosed in Edwards, J. P. et. al., Bio. Med. Chem. Let., 9, 1003-1008 (1999) and Hamann, L. G. et. al., J. Med. Chem., 42, 210-212 (1999), and progesterone receptor agonists ("PRA"), such as levonorgestrel, medroxyprogesterone acetate (MPA).

Still other suitable medicinal and pharmaceutical agents include aP2 inhibitors, such as those disclosed in U.S. Ser. No. 09/519,079 filed Mar. 6, 2000, PPAR gamma antagonists, PPAR delta agonists, beta 2 adrenergic agonists, beta 3 adrenergic agonists, such as AJ9677 (Takeda/Dainippon), L750355 (Merck), or CP331648 (Pfizer), other beta 3 agonists as disclosed in U.S. Pat. Nos. 5,541,204, 5,770,615, 5,491,134, 5,776,983 and 5,488,064, a lipase inhibitor, such as orlistat or ATL-962 (Alizyme), a serotonin (and dopamine) reuptake inhibitor, such as sibutramine, topiramate (Johnson & Johnson) or axokine (Regeneron), a thyroid receptor beta drug, such as a thyroid receptor ligand as disclosed in WO 97/21993, WO 99/00353, and GB98/284425, and anorectic agents, such as dexamphetamine, phentermine, phenylpropanolamine or mazindol.

Still other suitable medicinal and pharmaceutical agents include HIV and AIDS therapies, such as indinavir sulfate, saquinavir, saquinavir mesylate, ritonavir, lamivudine, zidovudine, lamivudine/zidovudine combinations, zalcitabine, didanosine, stavudine, and megestrol acetate.

Still other suitable medicinal and pharmaceutical agents include antiresorptive agents, hormone replacement therapies, vitamin D analogues, elemental calcium and calcium supplements, cathepsin K inhibitors, MMP inhibitors, vitronectin receptor antagonists, Src $SH_2$ antagonists, vacular—$H^+$-ATPase inhibitors, ipriflavone, fluoride, Tibo lone, pro stanoids, 17-beta hydroxysteroid dehydrogenase inhibitors and Src kinase inhibitors.

The above other therapeutic agents, when employed in combination with the chemical entities described herein, may be used, for example, in those amounts indicated in the Physicians' Desk Reference (PDR) or as otherwise determined by one of ordinary skill in the art.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. These and other changes can be made to the disclosure in light of the detailed description.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or prior publication, or for any other reason. All statements as to the date or representation as to the contents of these documents is based on the information available to the applicants and does not constitute any admission as to the correctness of the dates or contents of these documents.

One skilled in the art readily appreciates that the present invention is well adapted to carry out the objects and obtain the ends and advantages mentioned, as well as those inherent therein. The details of the description and the examples herein are representative of certain embodiments, are exemplary, and are not intended as limitations on the scope of the invention. Modifications therein and other uses will occur to those skilled in the art. These modifications are encompassed within the spirit of the invention. It will be readily apparent to a person skilled in the art that varying substitutions and modifications may be made to the invention disclosed herein without departing from the scope and spirit of the invention.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention provides all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. It is contemplated that all embodiments described herein are applicable to all different aspects of the invention where appropriate. It is also contemplated that any of the embodiments or aspects can be freely combined with one or more other such embodiments or aspects whenever appropriate. Where elements are presented as lists, e.g., in Markush group or similar format, it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. For example, any one or more active agents, additives, ingredients, optional agents, types of organism, disorders, subjects, or combinations thereof, can be excluded.

Where the claims or description relate to a composition of matter, it is to be understood that methods of making or using the composition of matter according to any of the methods disclosed herein, and methods of using the composition of matter for any of the purposes disclosed herein are aspects of the invention, unless otherwise indicated or unless it would be evident to one of ordinary skill in the art that a contradiction or inconsistency would arise. Where the claims or description relate to a method, e.g., it is to be understood that methods of making compositions useful for performing the method, and products produced according to the method, are aspects of the invention, unless otherwise indicated or unless it would be evident to one of ordinary skill in the art that a contradiction or inconsistency would arise.

Where ranges are given herein, the invention includes embodiments in which the endpoints are included, embodiments in which both endpoints are excluded, and embodiments in which one endpoint is included and the other is excluded. It should be assumed that both endpoints are included unless indicated otherwise. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise. It is also understood that where a series of numerical values is stated herein, the invention includes embodiments that relate analogously to any intervening value or range defined by any two values in the series, and that the lowest value may be taken as a minimum and the greatest value may be taken as a maximum. Numerical values, as used herein, include values expressed as percentages. For any embodiment of the invention in which a numerical value is prefaced by "about" or "approximately", the invention includes an embodiment in which the exact value is recited. For any embodiment of the invention in which a numerical value is not prefaced by "about" or "approximately", the invention includes an embodiment in which the value is prefaced by "about" or "approximately".

"Approximately" or "about" generally includes numbers that fall within a range of 1% or in some embodiments within a range of 5% of a number or in some embodiments within a range of 10% of a number in either direction (greater than or less than the number) unless otherwise stated or otherwise evident from the context (except where such number would impermissibly exceed 100% of a possible value). It should be understood that, unless clearly indicated to the contrary, in any methods claimed herein that include more than one act, the order of the acts of the method is not necessarily limited to the order in which the acts of the method are recited, but the invention includes embodiments in which the order is so limited. It should also be understood that unless otherwise indicated or evident from the context, any product or composition described herein may be considered "isolated".

This invention is further illustrated by the following examples which should not be construed as limiting.

EXAMPLES

Materials and Methods
Mice and In Vivo Procedures

Aged C57BL/6 mice (22-24 months) were obtained from the National Institutes of Aging (NIA) and young C57BL/6 mice (2-3 months) were purchased from Jackson Laboratories, Bar Harbor, Me., USA. Mice were housed and treated as per Institutional Animal Care and Use Committees at Harvard University approved protocol.

For parabiosis experiments, surgeries were performed as described previously (Bunster and Meyer, 1933; Ruckh et al., 2012). Blood chimerism was confirmed in a subset of young isochronic and heterochronic parabiotic pairs by flow cytometry measuring the frequency of donor-derived blood cells from one partner (CD45.1+) in the spleen of the other partner (CD45.2+) after 4 weeks of joining. Partner-derived cells typically represented 40-50% of splenocytes, indicative of establishment of parabiotic cross-circulation. This method could not be used to verify the establishment of chimerism in old isochronic pairs, because old CD45.1+ mice are not available for purchase from NIA. After 4 weeks of joining, parabiotic mice were sacrificed and muscles were harvested for subsequent experiments.

For treatment with GDF11, mice were randomly divided into two groups: 1 group of mice was treated with GDF11 by daily IP injection at 0.1 mg/kg of mouse body weight whereas the other group of control mice was injected with the vehicle (PBS with 0.1% BSA and 4 mM HCl). Individual lots of rGDF11 were quality controlled by spectrophotometer, gel electrophoresis and K562 erythroid differentiation bioactivity assay according to the supplier's recommendations, before use in in vivo assays. After 30 days of treatment, unless specified otherwise, mice were sacrificed and muscles were harvested for subsequent experiments. For in vivo BrdU labeling of proliferating cells, mice were fed BrdU (0.5 mg/ml) in drinking water containing 5% sucrose for 4-6 weeks before they were sacrificed and tissues were harvested for analysis.

Muscle Stem Cell Isolation

Muscle stem cells were isolated from intact limb muscles (extensor digitorum longus, gastrocnemius, quadriceps, soleus, tibialis anterior, and triceps brachii) as described previously. (Cerletti et al., 2008; Conboy et al., 2003; Sherwood et al., 2004). After isolation, all myofiber-associated cells were incubated in Hank's Buffered Salt Solution (Gibco) containing 2% donor bovine calf serum on ice for 20 min. with the following antibodies: 30-F11 (1:200, anti-mouse CD45, phycoerythrin (PE) or allophycocyanin (APC) conjugate (eBioscience, San Diego, Calif.)); M1/70 (1:200, anti-mouse CD11b, PE conjugate, (eBioscience); or 1:800, antimouse CD11b, APC conjugate, (eBioscience)); D7 (1:800, anti-Sca-1, Ly-6A/E, APC conjugate (eBioscience)), $\beta$1-integrin (1:200, anti-mouse CD29, purified, (BD Pharmingen, San Jose, Calif.; or 1:400, anti-mouse/rat CD29, PE conjugate (Biolegend, San Diego, Calif.); CXCR4 (1:100, biotinylated anti-mouse CD184 (BD Pharmingen)), Streptavidin (1:100, Cy7-PE conjugate (eBioscience)), anti-armenian hamster IgG, fluorescein isothiocyanate (FITC) conjugate (1:100, eBioscience). Muscle stem cells, identified as CD45−Sca-1−Mac-1−CXCR4+$\beta$1-integrin+(Cerletti et al., 2008; Sherwood et al., 2004) were sorted by Fluorescence Activated Cell Sorting method using Aria II, MoFlo or Bertha (BD Life Sc.) Live cells were identified as calcein blue positive (1:1000, Invitrogen, Carlsbad, Calif.) and propidium iodide negative (PI, 1 mg/mL).

Muscle stem cells were double-sorted to maximize purity. For intracellular staining, myofiber-associated cells were first stained for surface antigen markers and then fixed and permeabilized using cytofix/cytoperm buffer (APC BrdU Flow Kit, BD Pharmingen™) according to the manufacturers' instructions. Cells were subsequently stained with APC-anti-BrdU (APC BrdU Flow Kit, BD Pharmingen™), or anti-activated (cleaved) caspase-3 (Asp175) Alexa-488 conjugate (1:50, Cell signaling), or anti-phospho-53BP1 (S25) (1:50, Bethyl laboratories). If secondary antibody staining was required, cells were first blocked with goat serum (1/100) and anti-CD16/32 NA/LE (2.4G2, BD) and then stained with goat anti-rabbit-Alexa488 (1:100, Invitrogen). For studies of activated caspase-3 or phospho-53BP1 expression, a subset of myofiber-associated cells was treated with 950 µM H2O2 at 37° C. for 2 hours to generate a positive control for staining, and a distinct subset was stained with secondary antibody alone to serve as negative control, as indicated. FACS data were collected using DIVA (Becton Dickinson (BD), Franklin Lakes, N.J.) and analyzed offline using Flowjo software (Tree Star, Inc., version 8.6.1, Ashland, Oreg.) to determine yield as the total number of CD45−Sca1−Mac1−CXCR4+$\beta$1-integrin+ cells sorted per gram of muscle tissue or frequency out of live cells.

Single Cell Gel Electrophoresis or Comet Assay

For Comet assay, approximately 3,000 muscle stem cells were double sorted into Eppendorf tubes containing 350 ul of Hank's Buffered Salt Solution (Gibco) with 2% donor bovine calf serum. Comet assay was performed according to manufacturer's instructions (Cell Biolabs, Inc. San Diego, Calif.). Briefly, cells were centrifuged at 700 rcf for 3 min. at room temperature and the cell pellet was re-suspended with molten low melting point agarose pre-incubated at 37° C. for at least 20 min. The cell-agarose suspension was then applied onto the comet slides gently allowing to form a thin layer and the agaorse layer was allowed to solidify on ice before being submerged into the lysis buffer. The lysis of cells was carried out for 12 hours at 4° C. and the DNA was then electrophoresed in neutral or alkaline buffer as indicated. Extreme care was taken to minimize exposure to light during sorting or subsequent processing and handling of cells until they were electrophoresed. Finally electrophoresed and VistaDye stained DNA was visualized under Zeiss Imager M1 Fluorescence microscope (Carl Zeiss, Thornwood, N.Y.) and 100-250 nuclei per animal were visually scored according to published protocols. This scoring approach has been documented to be equally effective for detecting differences as other methods (e.g. calculation of tail moment).

Immno-Fluorescence Staining of Muscle Stem Cells, Single Myofibers and Muscle Cryosections For immunostaining, approximately 5,000 muscle stem cells were directly sorted into a small droplet of PBS and allowed to settle onto the slides by gently resting the slides on ice for 30 minutes before fixation with 4% PFA for 20 minutes at room temperature. Immunostaining of single myofibers was performed on dissected hindlimb muscles from young (2 mo.) and old (24 mo.) mice. Dissected muscles were digested with 0.2% collagenase type II, minced, and fixed in 4% paraformaldehyde in PBS. Sorted cells, single myofibers or muscle cryosections were washed with PBS, permeabilized and blocked using 2% BSA/0.5% Goat Serum/0.5% Triton X in PBS for 60 min. at room temperature. For immunostaining with primary antibodies raised in mouse, the M.O.M immunodetection kit (Vector Laboratories, Burlingame, Calif.) was used as per manufacturer's instructions. Primary antibodies (mouse monoclonal anti-Pax7 (1:100 DSHB, University of Iowa) and rabbit polyclonal anti-γH2AX (1:500, Abcam), mouse anti-CD31 (1:250), rabbit-polyclonal anti-laminin(1:500)) were incubated with samples for 12-16 hours at 4° C., and secondary antibodies (1:200, AlexaFluor 555 or AlexaFluor 488, Invitrogen) for 60 min. at room temperature (with 3-4 washes in PBS following each incubation). For 53BP1 immunostaining, serum block (10% goat serum) and detergent (0.1% Tween20) were included during both primary and secondary antibody incubations. For single myofibers, after secondary antibody incubation and washing with DPBS and one extra wash with DPBS containing 0.01% Tween20 was introduced. Likewise, for muscle cryosections, after fixation with 4% PFA and wash with PBS, antigen retrieval was performed with 2% SDS in PBS for 20 minutes at room temperature. All samples were mounted on slides in VECTASHIELD® mounting medium containing DAPI. Fluorescence images were obtained under Zeiss Imager M1 Fluorescence microscope (Carl Zeiss, Thornwood, N.Y.) and quantified using ImageJ. 50-100 confocal images of sorted cells per sample were obtained using an Inverted LSM 510 Meta or Inverted LSM 700 Meta (Carl Zeiss, Thornwood, N.Y.) and quantified using AIM software and ImageJ.

Neuromuscular Junction Immunofluorescence.

Extensor digitorum longus (EDL) muscles were fixed for 1 hour at room temperature (4% paraformaldehyde in PBS). Unless otherwise indicated, all incubations were performed at room temperature. EDL muscles were teased into bundles of muscle fibers. Muscles were washed twice for 15 min. in PBS, incubated 15 min. with 100 mM glycine in PBS, and rinsed in PBS. After removal of the overlying connective tissue, muscles were permeabilized and blocked for 1 hr. in PBS containing 2% bovine serum albumin, 4% normal goat serum, and 0.5% Triton X-100. To quantify the number and density of acetylcholine receptors (AChRs), muscles were stained with AlexaFluor 594 α-Bungarotoxin (BTX), first for 1 hr. at room temperature and then overnight at 4° C. After three 30 min washes in PBS, muscles were rinsed in PBS, fixed 30 min with 1% formaldehyde in PBS, washed three times for 10 min. in PBS, and flat-mounted in Vectashield with DAPI (Vector Laboratories, Burlingame, Calif.). Images were acquired using a Zeiss M1 or LSM 510 confocal microscope.

Myogenesis Assays

Myogenesis assays. Muscle satellite cells from young or aged mice were clone-sorted (single cell/well) or bulk-sorted (200 cells/well) into 96-well plates containing growth medium (F10, 20% horse serum, 1% Glutamax and 1% pen/strep) using the automated cell deposition unit (ACDU) of the Aria II (BD Biosciences). Prior to sorting, 96-well plates were coated with collagen/laminin by incubating the wells with PBS containing collagen (1 mg/ml, Sigma) and laminin (10 mg/ml, Invitrogen) for at least an hour at 37° C. Satellite cells were cultured in growth media comprised of F10, 1% glutamax, 1% Penstrep and 20% horse serum or knock-out serum replacement (KOSR, Invitrogen), where indicated, with fresh bFGF added daily at 5 ng/ml final concentration. Purified recombinant GDF11 (rGDF11, catalog #120-11, PeproTech), resuspended in PBS containing 0.1% BSA and 4 mM HCl, was added daily at the concentrations indicated. Individual lots of rGDF11 were quality controlled by spectrophotometer, gel electrophoresis and K562 erythroid differentiation bioactivity assay according to the manufacturer's recommendations, before use in in vitro assays. Wells containing myogenic colonies were either counted by brightfield microscopy or fixed with 4% PFA and the number of cells per well was counted on a Celigo automated microscope as Hoechst-stained nuclei at the indicated time points. For differentiation assays, satellite cells were sorted into 24-well plates at 5000 cells per well. Cells were cultured in growth media (described above) supplemented with bFGF for 5 days. At 5-8 days after plating, media were changed to differentiation media (DMEM, 1% GlutaMax, 1% pen-strep, and 2% FBS) and cultured for an additional 3-7 days. For differentiation analyses, myotubes were stained with anti-fast myosin (Sigma), DAPI, and AlexaFluor 488 conjugated Phalloidin (Life Technologies). For mitochondrial staining on myotubes, satellite cells were proliferated and differentiated into myotubes on 24-well plate compatible for microscope imaging (ibidi μ-plate). After 5 days in differentiation media, myotubes were washed in PBS and incubated in 250 nM Mitotracker Orange for 1 hr. at 37° C. Cells were washed twice and fixed in 2% paraformaldehyde for 10 min. at room temperature. Myotubes were counterstained with DAPI and Phalloidin (Life Technologies). Images were acquired using a Zeiss Observer D1 inverted microscope.

Muscle Injury and Muscle Sectioning

Tibialis anterior (TA) muscles of anesthetized mice were cryoinjured or injured with cardiotoxin (at 0.3 mg/ml) one week before harvest. Harvested muscles were fixed in 4% PFA and embedded in paraffin for sectioning. H&E staining was performed on 8-10 μm paraffin-embedded sections for quantification of centrally nucleated regenerating myofibers of injured and contralateral, uninjured TA muscles. For each sample, cross sectional area of 120-150 regenerating myofibers were blindly measured from 4 slides with 3 consecutive sections on each slide.

Satellite Cell Transplantation.

Anesthetized mdx mice were injected with 25 µl (0.03 mg/ml) of Naja mossambica mossambica cardiotoxin (Sigma) into TA muscles 1 day prior to cell transplantation. The next day, double-sorted satellite cells isolated from 6-8 weeks old GFP transgenic mice (C57BL/Ka-β-actin-EGFP (3-5)) and irradiated with gamma-irradiation at indicated dosages (0, 50 or 100 rad) were re-suspended in 5-10 µl PBS and injected directly into these pre-injured muscles. Injected TA muscles were harvested 4 weeks after transplant, snap-frozen in liquid nitrogen cooled methylbutane, and serially sectioned throughout the TA muscle from tendon to belly using Microm HM550 cryostat (Thermo Scientific). For transplantation experiments in aged mice, male mice (22 months old) were randomized into control (PBS, n=4) or rGDF11 (n=4) groups and treated as described above. After 4 weeks of vehicle or rGDF11 treatment, TA muscles were injured with cardiotoxin and GFP+ satellite cells (30,000 per leg) were transplanted the following day. Injected TA muscles were harvested 2 weeks after transplant, frozen muscle sections were processed for immunofluorescence as described above. Briefly, sections were fixed in 4% PFA for 1 hr and washed three times in PBS for 10 min. at RT. Sections were counterstained with Alexa488 conjugated anti-GFP and AlexaFluor 555 conjugated Phalloidin (Life Technologies) and mounted with Vectashield with DAPI (Vector Laboratory). 7-8 slides per muscle and 10-12 sections per slide from each experimental group were prepared and analyzed blindly to determine the maximum number of engrafted (GFP+) fibers and cross-sectional area of engrafted fibers using Axiovision software (Zeiss).

Physical Endurance Test.

For endurance exercise testing, vehicle- or rGDF11-treated aged (24 mo. of age) C57Bl/6 male mice were exercised using an adjustable variable speed belt treadmill (AccuPacer, AccuScan Instruments, Inc). Animals were first acclimated to the treadmill by walking at 5 meters per minute (mpm) with inclination set at 0° for 5 minutes. The speed and inclination of the treadmill were gradually increased in a step-wise manner to a maximum of 20 mpm and 15° respectively. Animals were exercised on the treadmill for a maximum of 90 minutes or until they were exhausted. Exhaustion was determined by refusal of mice to remain on the treadmill for at least 20 seconds.

Measurement of Biochemical Metabolites after Treadmill Exercise.

Immediately following a 20 min. bout of exercise, the tails of exercised mice were nicked with a scalpel and the tail vein was massaged to obtain an appropriate volume of blood (approximately 3 µl) for both glucose and lactate measurements. Blood glucose was measured using an OneTouch® Ultra Blood Glucose Meter (Lifescan). Blood lactate was measured using the Lactate Plus Meter (Nova Biomedical). Measurements of glucose and lactate levels during exercise were performed at the indicated time point (i.e., at 0, 20, 40, 60 minutes of running, and at exhaustion).

Grip-Strength Test.

For measurement of in vivo muscle force and neuromuscular function, vehicle- or rGDF11-treated (for 4 weeks) aged (25 mo. of age) C57Bl/6 male mice were allowed to grasp onto the horizontal metal grid of the grip strength meter (Columbus Instruments, Columbus, Ohio) by using only the forelimbs and pulled backwards 3 times. The force applied to the grid each time before the animal lost its grips was recorded in Newton. The maximum force in Newton was also normalized to the body weight of each animal and represented in the data.

Quantitative PCR

For RNA isolation from satellite cells, at least 10,000 cells were directly sorted into 500 ul Trizol reagent (Life technologies) and manufacturer's instructions were followed. Isolated RNA was converted to cDNA using Superscript III Reverse Transcriptase Supermix Kit (Invitrogen, 11752-050). Real-time quantitative PCR reactions were carried out in an ABI 7900HT machine, using SYBR Green PCR mix (Applied Biosystems, 4309155). actin was used as a housekeeping gene, and mRNA transcript levels of the genes of interest were normalized to actin mRNA levels. Experimentally validated primer sequences designed to span introns were obtained from PrimerBank.

ELISA and Western.

For ELISA, crushed muscle (tibialis anterior) extracts (10 mg/ml) or plasma harvested from young (2-3 mo.) and aged male C57BL/6 mice (24 mo.) were diluted as indicated and used on TGF-β1 Immunoassay Quantikine® ELISA Catalog #MB100B and Myostatin Immunoassay Quantikine® ELISA Catalog # DGDF80 (R&D systems, Minneapolis, Minn.) as per manufacturer's instructions. For Westerns, 100 µg of plasma or whole muscle (quadriceps or gastrocnemius) extracts were loaded onto appropriate (4-20%) gradient Criterion Tris-HCl polyacrylamide gels (Biorad Labs) and immunoblotted for proteins as indicated using the following antibodies: anti-GDF11 (Abcam rabbit mAb 1:1000), anti-GDF11 (mouse mAb 1:500, obtained from Richard Lee), anti-PGC-1α (1:1000, Santa Cruz), and anti LC3B (1:1000, Novus). Densitometric quantification of Western data were normalized to GAPDH (1:2000, Santa Cruz) or Actin (1:1000, Sigma) serving as loading controls.

Mitochondrial Function Assay.

The rate of oxygen consumption (OCR) was measured using Seahorse Bioscience extracellular flux analyzer (XF24). FACS isolated satellite cells were seeded into 24-well plates at a density of 5000/well and differentiated into myotubes as described above. Basal and maximal oxygen consumption rates (OCR) were calculated by comparing values with or without the mitochondrial uncoupler, FCCP (5 µM). The final OCR values (pmol/min) were normalized to total protein concentration per well.

RNA Transcriptome Analysis.

RNA transcriptome analysis was performed using Affymetrix GeneChip Mouse Genome 430 2.0 arrays. Raw microarray data have been deposited in the Gene Expression Omnibus database. www.ncbi.nlm.nih.gov/geo (GSE50821). A subset of differentially expressed myogenic transcripts was chosen to generate a heatmap from the original dataset normalized by gcRMA algorithm and SAM cutoff (<10% q-values) using R statistical software.

Discussion

Age-dependent dysfunction in adult tissue stem cells has been cited as a significant contributor to the deficits in function and regenerative potential that arise in many organs as a result of physiological aging. The blood, CNS, and other tissues have been reported to show altered stem cell numbers and reduced stem cell function with age.

In many tissues, resident stem cell populations are required to maintain appropriate function, structure and regenerative potential, and age-related dysfunction is often accompanied by a reduced activity and/or number of these cells.

Age-dependent dysfunction in adult stem cells is attributable to both cell-intrinsic and extrinsic inputs, including systemic soluble factors that regulate regenerative function (Liu and Rando. *J. Cell Biology* 2011; 193, 257). Among cell intrinsic properties, compromised genomic integrity has been hypothesized to be one of the critical mechanisms underlying the functional decline of aged stem cells, and among cell extrinsic signals, recent efforts have focused particularly on systemic factors and their ability to promote or reverse age-associated changes in regeneration in tissues as diverse as the skeletal muscle, liver and CNS (Wagers and Conboy. *Cell* 2005; 122, 659; Ruckh et al. *Cell Stem Cell* 2005; 10, 96). Importantly, while the molecular mediators of these systemic effects clearly represent promising targets for therapeutic intervention, their molecular identities are just beginning to be revealed.

Here, the present investigators employed heterochronic parabiosis to investigate the impact of extrinsic (systemic) factors on intrinsic (genomic integrity) properties of tissue stem cells. Using skeletal muscle as an experimental system, with its well-characterized stem cell population and regenerative responses, we show that aged muscle stem cells, also known as satellite cells, acquire increased levels of DNA damage in old age and that exposure to a youthful circulation restores satellite cell genomic integrity and myogenic function. We further demonstrate that similar functional and genomic reprogramming can be accomplished by restoration of youthful levels of the circulating hormone Growth Differentiation Factor 11 (GDF11), which typically declines with age.

Skeletal muscle exhibits age-related deficits in regenerative activity, as demonstrated by analysis of skeletal muscle histology in young (2 month) or old (24 month) mice challenged by muscle cryoinjury. Regenerating tissue in aged mice exhibits a marked decrease in the overall number of centrally nucleated (newly regenerated) fibers (FIG. 1A, analyzed 7 days after injury) (Cerletti, et al. *Cell Stem Cell* 2012; 10, 515), which are significantly smaller across a range of cross-sectional areas (FIG. 1B, $p<0.05$ by Step-down Bonferroni analysis) as compared to regenerating tissue in young mice. These findings indicate a reduced efficiency or robustness of muscle repair in aged animals, which slows recovery from damage and may contribute to age-related muscle dysfunction.

Muscle regenerative potential is determined in large part by a specialized subset of muscle fiber-associated mononuclear cells called "satellite cells" (Jang et al. *Cold Spring Harb Symp Quant Biol* 2011; 76, 101). Satellite cells are located beneath the basal lamina, adjacent to the plasma membrane of muscle fibers, and act as muscle stem cells with self-renewal and differentiation capacity. Satellite cells can be isolated using Fluorescence Activated Cell Sorting (FACS) based on their unique cell surface marker profile (CD45−Sca-1−Mac-1−CXCR4+β1-integrin+) (Sherwood et al. *Cell* 2004; 119, 543). Importantly, these phenotypic markers that identify satellite cells are distinct from those that mark mature skeletal muscle cells or myoblasts, and >95% of FACS-sorted satellite cells express the canonical satellite cell marker Pax7. This cell population also contains all of the cell-autonomous myogenic activity of adult mouse skeletal muscle (Sherwood et al. 2004), indicating that changes in the number or function of this cell population are likely to translate directly into changes in muscle regenerative potential.

Figure 4:
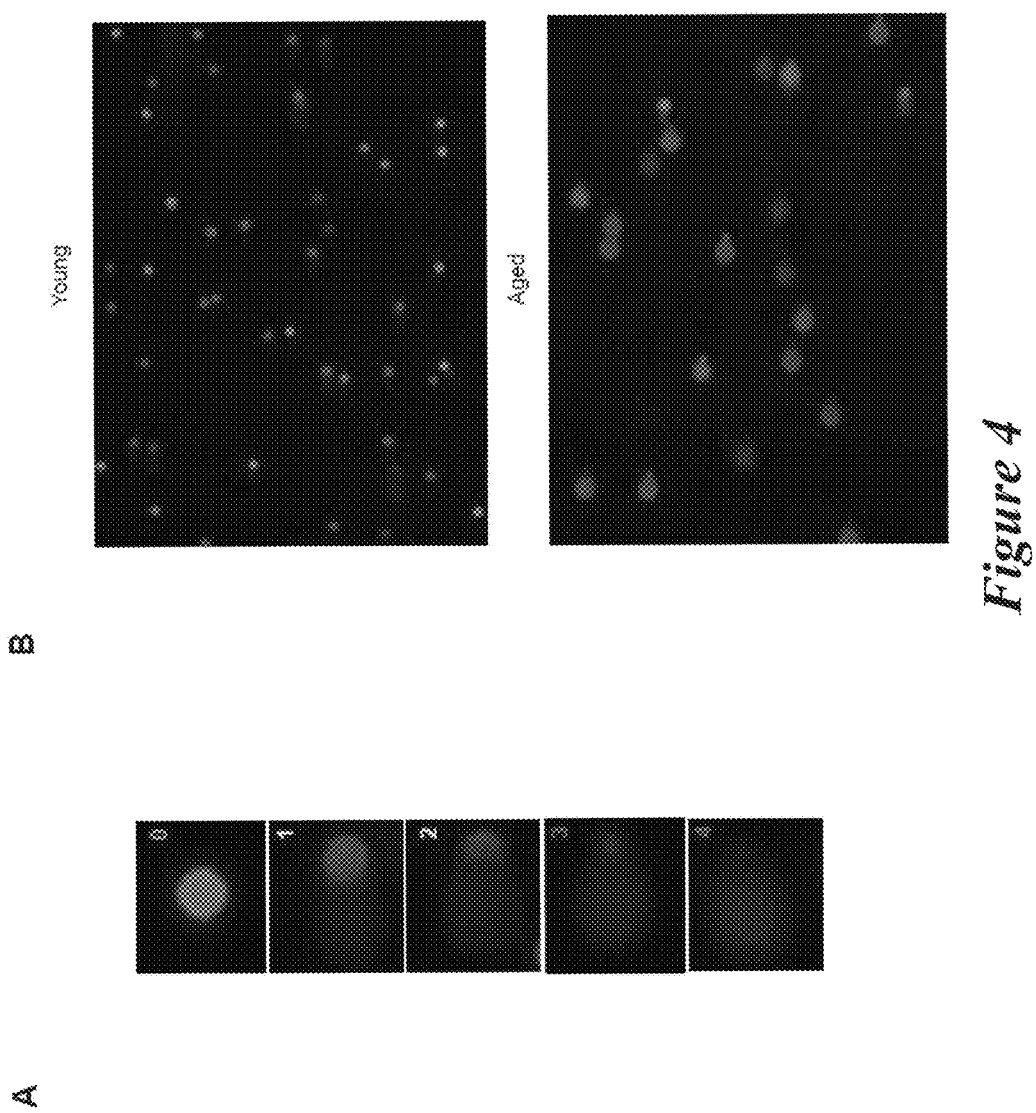
FIG. 4 shows results of comet assays performed on freshly sorted satellite cells (i.e., skeletal muscle stem cells). (A) Visual scoring key of comet assays. Scores are shown on the top right corner and represent the extent of damage by a scale of 0 to 4, with 0 being no damage and 4 being maximal damage. Numbers are also color coded for quantification as in FIG. 1D. (B) Representative comet images of satellite cell nuclei from young (Top, 2 mo. of age) and aged (bottom, 24 mo. of age). Muscle stem cell nuclei from aged mice show increased DNA damage as compared to muscle stem cells from young mice.
Figure 5:
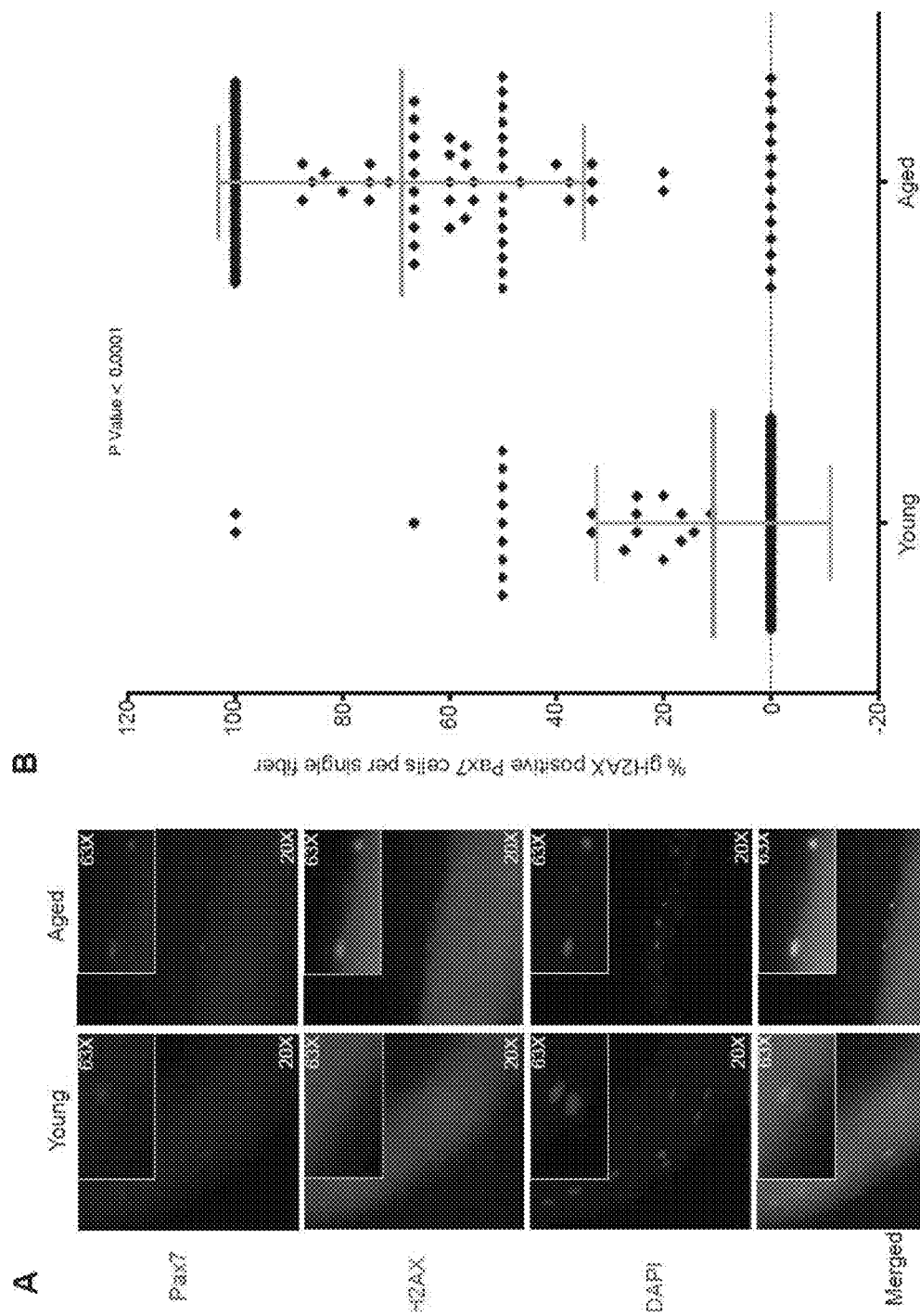
FIG. 5 shows Pax7-staining muscle stem cells on isolated myofibers also exhibited increased immunoreactivity for the phosphorylated form of the variant histone H2AX (pH2AX). (A) Representative immunofluorescent images of pH2AX (green) in aged and young Pax7+ nuclei on isolated myofibers. Magnification at 20×, with inset at 63×. (B) Quantification of % pH2AX+ nuclei among young or aged satellite cells stained as in (A). Data compiled from 3 independent experiments. Each black diamond represents data from a single fiber (n=30 fibers analyzed per group). Orange lines represent mean±SD; P value as indicated was calculated by Mann-Whitney test.
Figure 6:
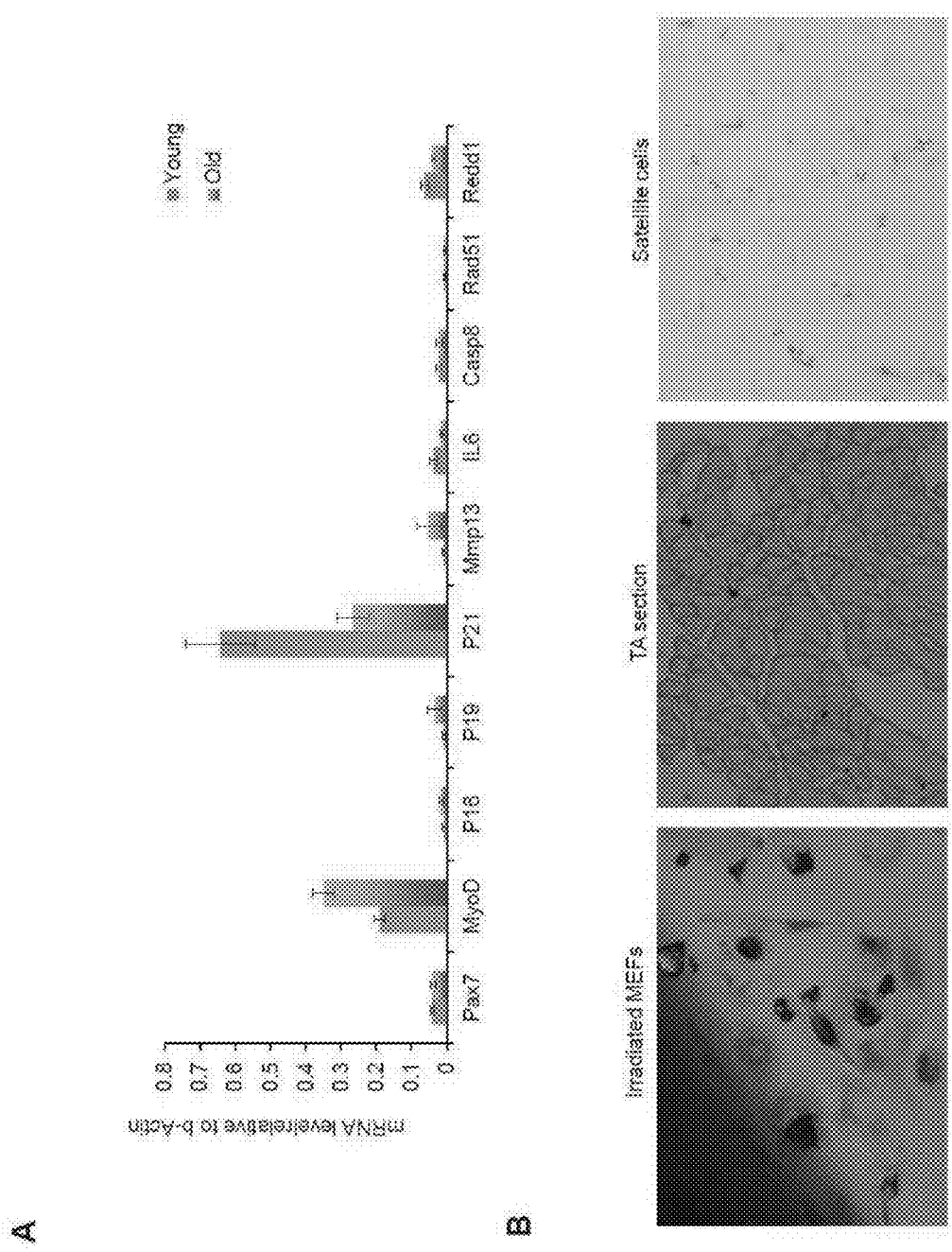
FIG. 6 shows expression analysis of gene transcripts associated with myogenic differentiation, cell cycle, or DNA damage by qRT-PCR (A) or SA-βGal assay to detect senescent cells in muscle sections (TA section), sorted muscle stem cells (satellite cells) or irradiated mouse embryo fibroblasts (MEFs) as control (B). Muscle stem cells from aged mice show higher levels of MyoD and lower levels of p21, and Redd1 as compared to young satellite cells (A). Cellular senescence was not detected in muscle sections or sorted muscle stem cells of aged mice (B).

Aged muscle exhibits decreased satellite cell number, impaired satellite cell function and reduced regenerative potential. To evaluate possible age-related changes in muscle satellite cells, the present investigators used a clonal myogenic assay (Cerletti et al. 2012) that permits analysis on a per cell basis of satellite cell function. Satellite cells, identified by the CD45−Sca-1−Mac-1−CXCR4+β1-integrin+ marker phenotype described above were double sorted (>98% purity), and single cells seeded and grown ex vivo in a 96-well plate. These assays revealed a severe impairment of aged satellite cells, which showed up to a 4 fold reduced colony forming efficiency as compared to young cells (FIG. 1C, $p<0.05$ by Student's t test). This decreased myogenic activity of aged satellite cells was accompanied by a marked reduction in DNA integrity, as scored by comet assays performed on freshly sorted satellite cells (FIG. 1D and FIGS. 4A and 4B). Only 8-20% of aged satellite cell nuclei contained absolutely intact (green bars, FIG. 1D) DNA, while approximately 60% of aged cells exhibited severely compromised DNA integrity (red bars, FIG. 1D, $p<0.05$ by Student's t test as compared to young satellite cells). Likewise, nearly 60% of satellite cells sorted from aged muscle (FIG. 1E) or identified by Pax7-staining on isolated myofibers (FIG. 5) also exhibited increased immunoreactivity for the phosphorylated form of the variant histone H2AX (pH2AX), a widely used marker of DNA damage in cells. In contrast, approximately 40% of the freshly isolated young satellite cells were devoid of any DNA breaks (FIG. 1D) and young satellite cell nuclei rarely contained more than 2 pH2AX foci when assayed after cell sorting (FIG. 1E) or on single myofibers (FIG. 5). Induction of DNA damage by X-irradiation reduced the myogenic function of young satellite cells in transplantation assays (FIG. 9), suggesting that increased DNA damage could cause impaired regeneration in aged muscle. These data indicate that age-associated deficiencies in muscle regeneration, likely arise from functional defects in muscle satellite cells and are associated with compromised DNA integrity. Notably, this apparent accumulation of DNA damage does not appear to induce senescence in aged satellite cells, as assessed by expression analysis of senescence-associated gene transcripts by qRT-PCR (FIG. 6A) or SA-βGal assay (FIG. 6B, right panel), nor did the aged cells reside in a senescent muscle microenvironment (FIG. 6B, middle panel).

Figure 2:
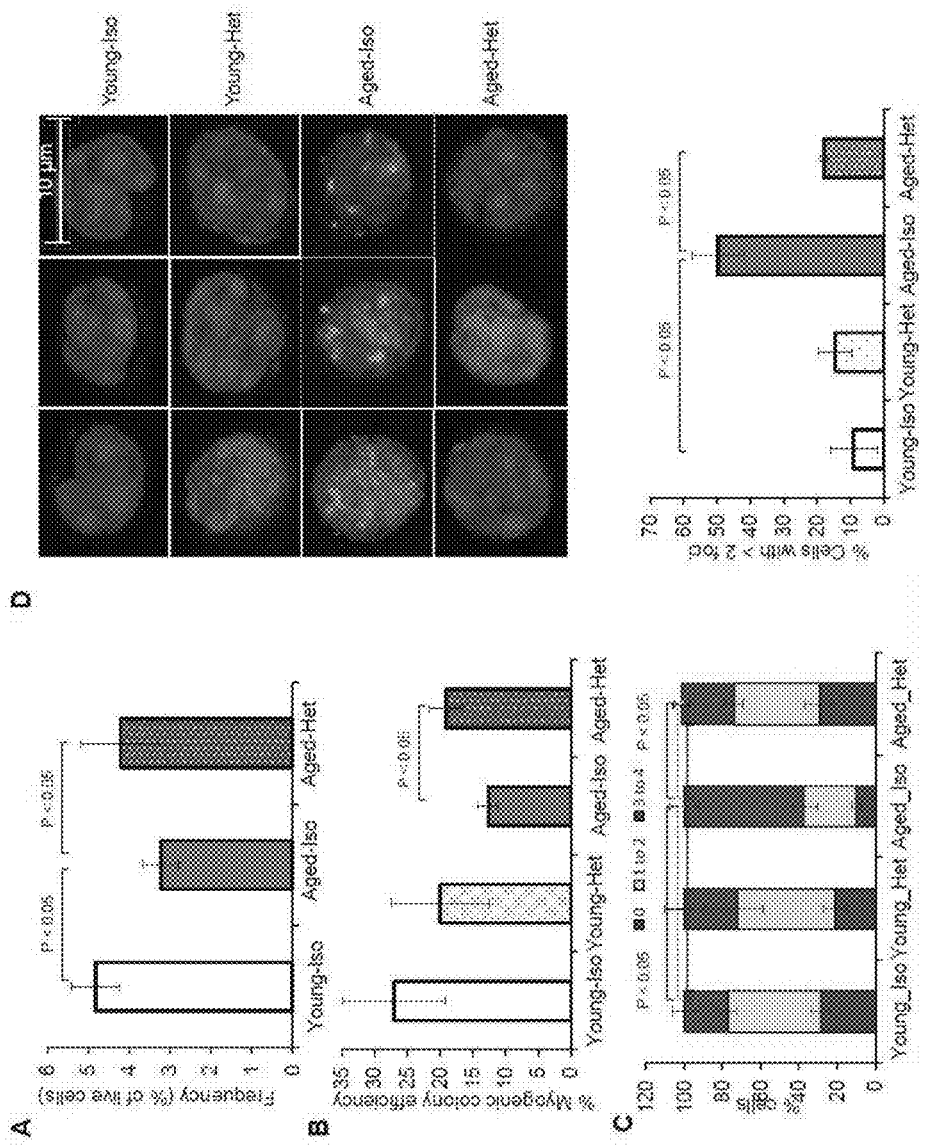
FIG. 2 shows rejuvenation of function and genomic integrity in aged muscle stem cells. (A) Satellite cell frequency analyzed by flow cytometry for cells harvested from aged partners of heterochronically (Het) joined mice (n=7 pairs) and young or aged partners of isochronically (iso) joined mice (n=5 pairs Iso-young and 5 pairs Iso-old). (B) Myogenic colony-forming efficiency of satellite cells isolated from young or aged partners of Iso or Het joined mice. (C) DNA damage analysis in freshly isolated satellite cells from young or aged partners of Iso or Het joined mice, detected by alkaline comet assays. (D) Representative immunofluorescence images of phosphorylated H2AX foci (green) in freshly isolated satellite cells from young or aged partners of Iso or Het joined pairs (n=3 mice analyzed per group). Data shown as projected images from confocal z-stacks of nuclei stained with DAPI (blue) and phosphorylated H2AX (green) at 100× magnification. Quantification is shown below. All graphs represent mean+/−standard deviations from 5-7 independent experiments. Student's t-test was used for statistical analysis.
Figure 10:
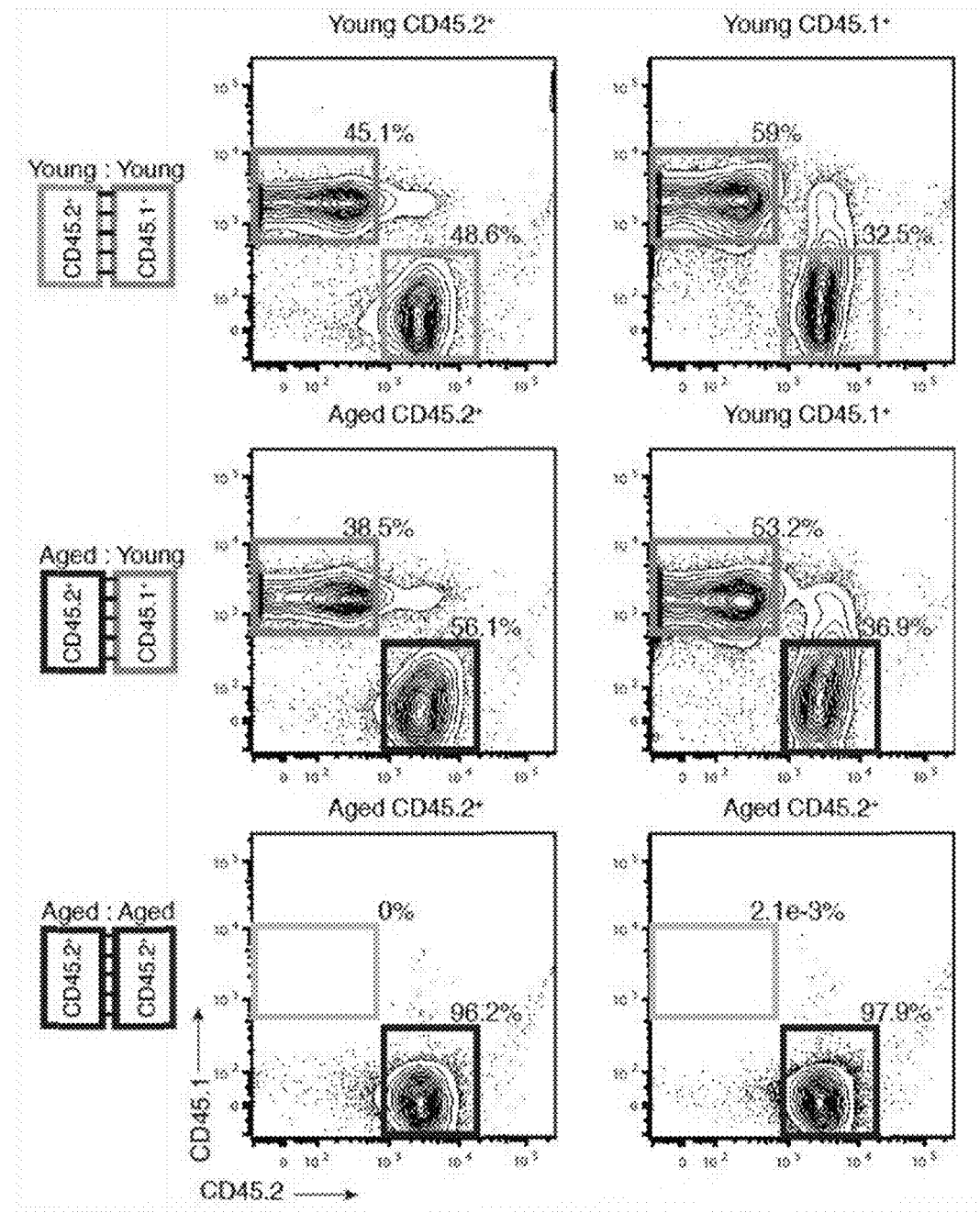
FIG. 10 illustrates parabiotic animals that were joined for 4-5 weeks, and cross circulation was confirmed in a subset of animals by analysis of congenic leukocyte surface antigens. Representative plots are shown indicating cross-engraftment of partner-derived cells in isochronic and heterochronic parabionts, in which one young partner was marked by expression of CD45.1 (blue) and the other partner by expression of CD45.2 (light brown). CD45 is a pan-leukocyte marker that allows discrimination of the origin of circulating white blood cells in the chimeric circulation. The percentage of CD45.1 versus CD45.2 congenic blood markers in splenocytes of young (blue or light brown) or aged (dark brown) partners from young-isochronic, young-heterochronic and agedisochronic or aged-heterochronic parabiotic pairs is indicated for each gate. The present investigators were unable to assess chimerism in aged-isochronic pairs due to the unavailability of 22 mo. old CD45.1 mice; however, our extensive experience with this model, including prior studies using GFP-marked mice have demonstrated previously that cross-circulation is effectively established in these fully isogenic pairs. Heterochronic pairs were always compared to age-matched isochronic pairs (young-young or aged-aged) to exclude any impact of the parabiosis surgery itself.

As mentioned earlier, age-associated impairment in muscle regeneration was reversed by exposure of aged muscles to a youthful systemic environment via heterochronic parabiois (Conboy et al. *Nature* 2005; 433, 760), which exposes aged tissues to a youthful systemic environment and restores injury-induced satellite cell activation by up-regulation of Notch signaling. To test the hypothesis that declining number, activity and genomic integrity of aged satellite cells can be restored after systemic exposure to youthful environment, we generated heterochronic parabionts (FIG. 10), in which, 2-month old C57BL/6 males were surgically joined with 22-month aged partners to develop a common blood circulation and compared with isochronic (young-young or aged-aged) parabiotic controls. After maintaining the parabionts for 4-5 weeks, we observed that the frequency of satellite cells in aged partners of the aged-young heterochronic pairs increased significantly as compared to the aged partners of aged-aged isochronic animals (FIG. 2A). Moreover, double sorted satellite cells isolated from aged partners of aged-young heterochronic pairs exhibited significant recovery in myogenic colony formation efficiency as compared to those from aged partners of aged-aged isochronic pairs (FIG. 2B). Parallel to this recovery of myogenic function, the DNA integrity of the satellite cells isolated from aged partners of the aged-young heterochronic pairs re-acquired the "youthful" intactness of the young cells isolated from the young-young isochronic pairs (FIG. 2C), as assessed by Comet assay. Likewise, 3-fold fewer aged satellite cells isolated from the aged partners of the aged-young heterochronic pairs contained more than 2 phosphorylated H2AX foci than observed cells isolated from aged partners of aged-aged isochronic pairs (FIG. 2D). These findings suggest that age-related decline in muscle stem cell function, which in turn is correlated with compromised genomic integrity of these cells, is reversible and controlled at least in part by systemic factors.

Figure 11:
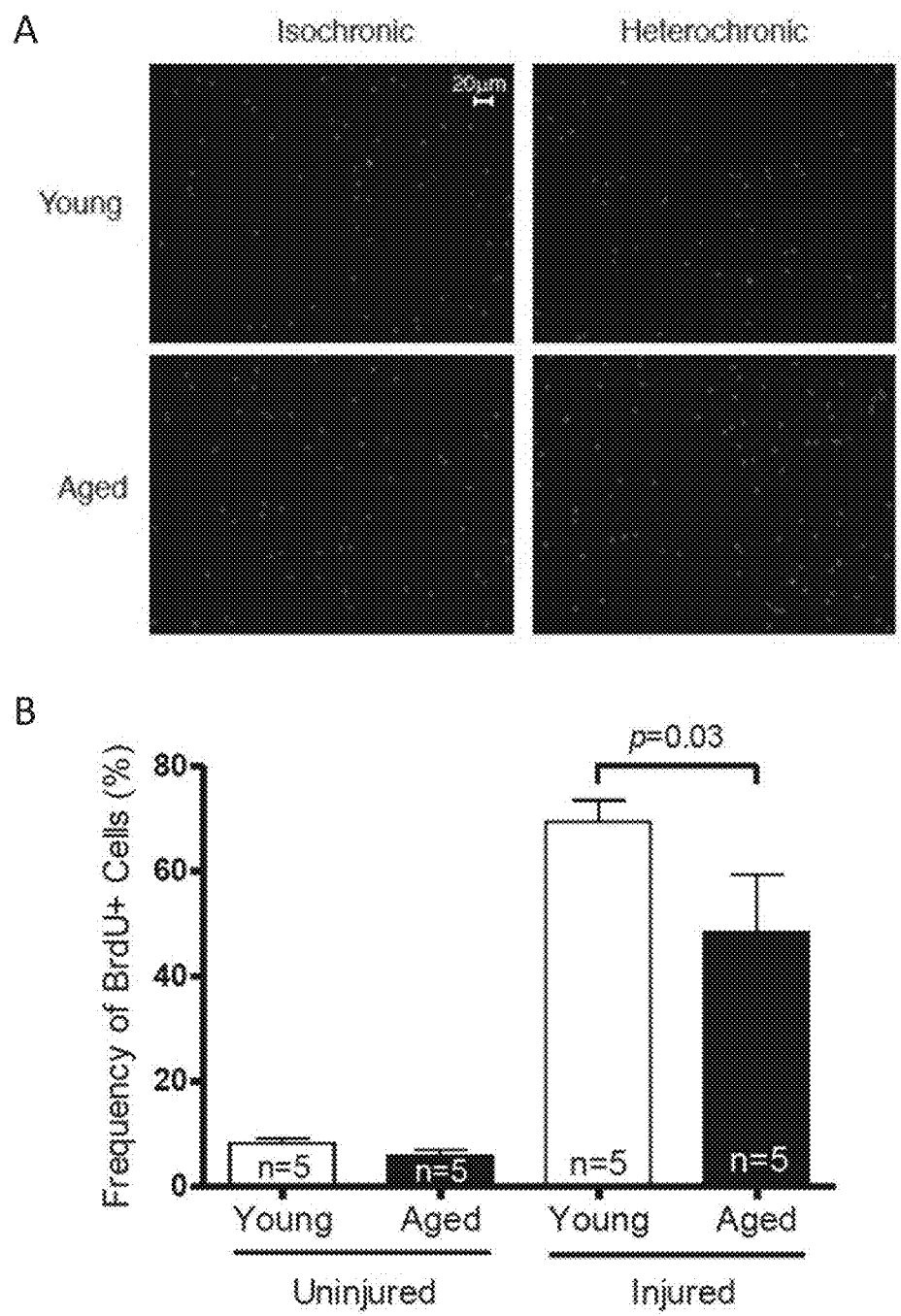
FIG. 11 shows that BrdU incorporation in young or aged satellite cells. Studies using histone-labeled mice indicate that an increased fraction of satellite cells in resting muscle enter cell cycle in aged, as compared to young, mice and raise the possibility that accumulation of DNA damage in aged satellite cells may result from an increased number of stalled or collapsed replication forks in the more proliferative aged satellite cell pool. To test whether repair of DNA damage in aged satellite cells exposed to a young circulation might occur due to a return of these cells to their usual quiescent state after exposure to young systemic signals, we labeled all cycling cells in isochronic or heterochronic parabionts by feeding animals BrdU for the duration of their parabiotic joining (4 weeks). (A) Representative immunofluorescent images of BrdU staining in satellite cell nuclei harvested from young or aged partners of heterochronically joined mice and young or aged partners of isochronically joined mice. In all cases, the frequency of BrdU+ nuclei is extremely low, and no differences could be detected among the 4 groups of mice. (B) Frequency of BrdU+ satellite cells analyzed by flow cytometry for cells harvested from uninjured or cardiotoxin-injured hind limb muscles of 5 aged and 5 young mice (not joined in parabiosis). Data are presented as mean±SD, with p-value calculated by Mann-Whitney test and indicated only for significant differences. BrdU incorporation was not different in uninjured muscle, and was reduced in satellite cells harvested from aged muscle, as compared to young, after injury. These data indicate that changes in satellite cell proliferative history are unlikely to explain the alterations in genome integrity or satellite cell function we observed after heterochronic parabiosis, and support the notion that aged satellite cells show impaired activation in response to regenerative cues.

To determine if increased DNA damage in aged satellite cells is a result of stalled or collapsed replication forks in the more proliferative aged satellite cell pool (Chakkalakal et al. Nature 2012; 490, 355), which may return to their usual quiescent stage after being exposed to young systemic milieu, we labeled all cycling cells by feeding the parabiotic pairs BrdU for the duration of the time that the pairs were attached. Interestingly, restoration of genomic integrity was not accompanied by detectable changes in satellite cell proliferation or proliferative history, as assessed by BrdU incorporation (FIG. 11). Contrary to the recent finding (Chakkalakal et al. 2012), the satellite cell pool as isolated by the marker combination of Sca1−, CD45−, Mac1−, β1-integrin+ and CXCR4+ from animals was not proliferative in either young or aged mice, until they were activated by muscle injury induced by cardiotoxin injection (FIG. 11). As expected, we also did not observe any cycling satellite cells in either young or aged partners of any parabiotic pairs ruling out any alterations of the quiescent nature of the satellite cell pool as a result of parabiotic surgeries.

Taken together, these data demonstrate that exposure to a young circulation is sufficient to reverse age-induced functional alterations and restore genomic integrity in muscle regenerative satellite cells. To begin to uncover the systemic signals that rejuvenate muscle stem cell function in aged mice exposed to a youthful circulation, we searched for age-variant blood-borne factors in young and aged mice. Previous studies of mouse skeletal muscle have implicated circulating cytokines, including transforming growth factor-β1 (TGF-β1), myostatin, and Wnt-like molecules as potent negative regulators of muscle growth and repair with age (Conboy et al., Nature 433:760, 2005; Brack et al., Science 317:807, 2007); however, blood-borne potentiators of skeletal muscle repair have not been described.

Figure 3:
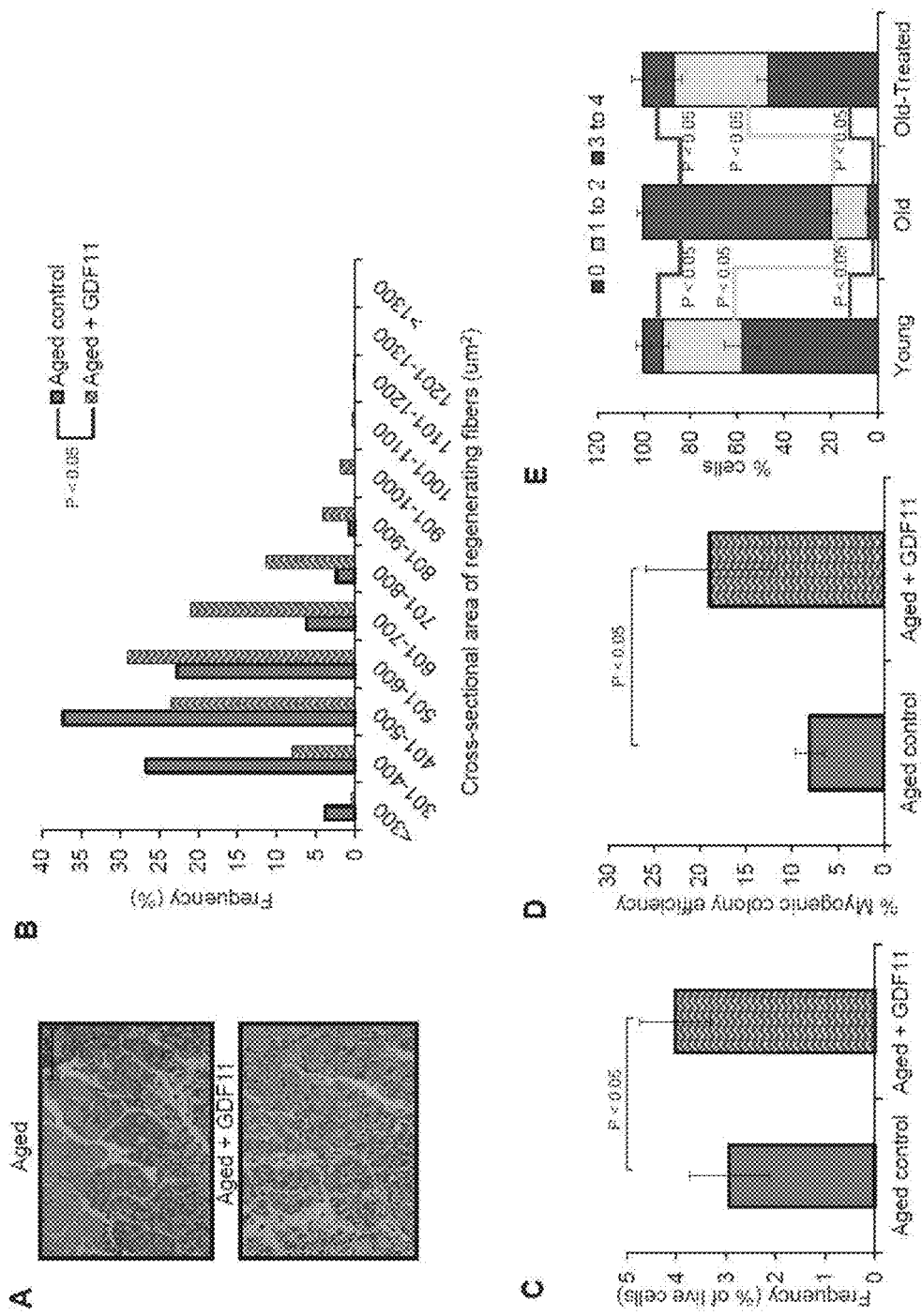
FIG. 3 shows rejuvenation of old muscle and function of muscle stem cells by in vivo treatment of rGDF11. (A) Representative H&E stains of regenerating tibialis anterior muscle on day 7 after cryoinjury for vehicle- (top panel) or GDF11-treated (bottom panel) aged mice. (B) Frequency distribution of myofiber size in regenerating muscle on day 7 after cryoinjury in vehicle- or GDF11-treated aged mice. Stepdown Bonferroni method was used for statistical analysis. (C) Frequency of satellite cells (% of live cells) analyzed by flow cytometry for vehicle- (n=7) or GDF11- (n=8) treated aged males. (D) Myogenic colony-forming efficiency of satellite cells isolated from vehicle or GDF11-treated aged mice. (E) Quantification of DNA damage in freshly isolated satellite cells from young mice or from vehicle- or GDF11-treated aged mice, detected by alkaline comet assays. Different colors represent different scores of comets as indicated. Graphs in C and D represent mean+/−standard deviations from 6-7 independent experiments. Statistical significance was determined by t-test.
Figure 12:
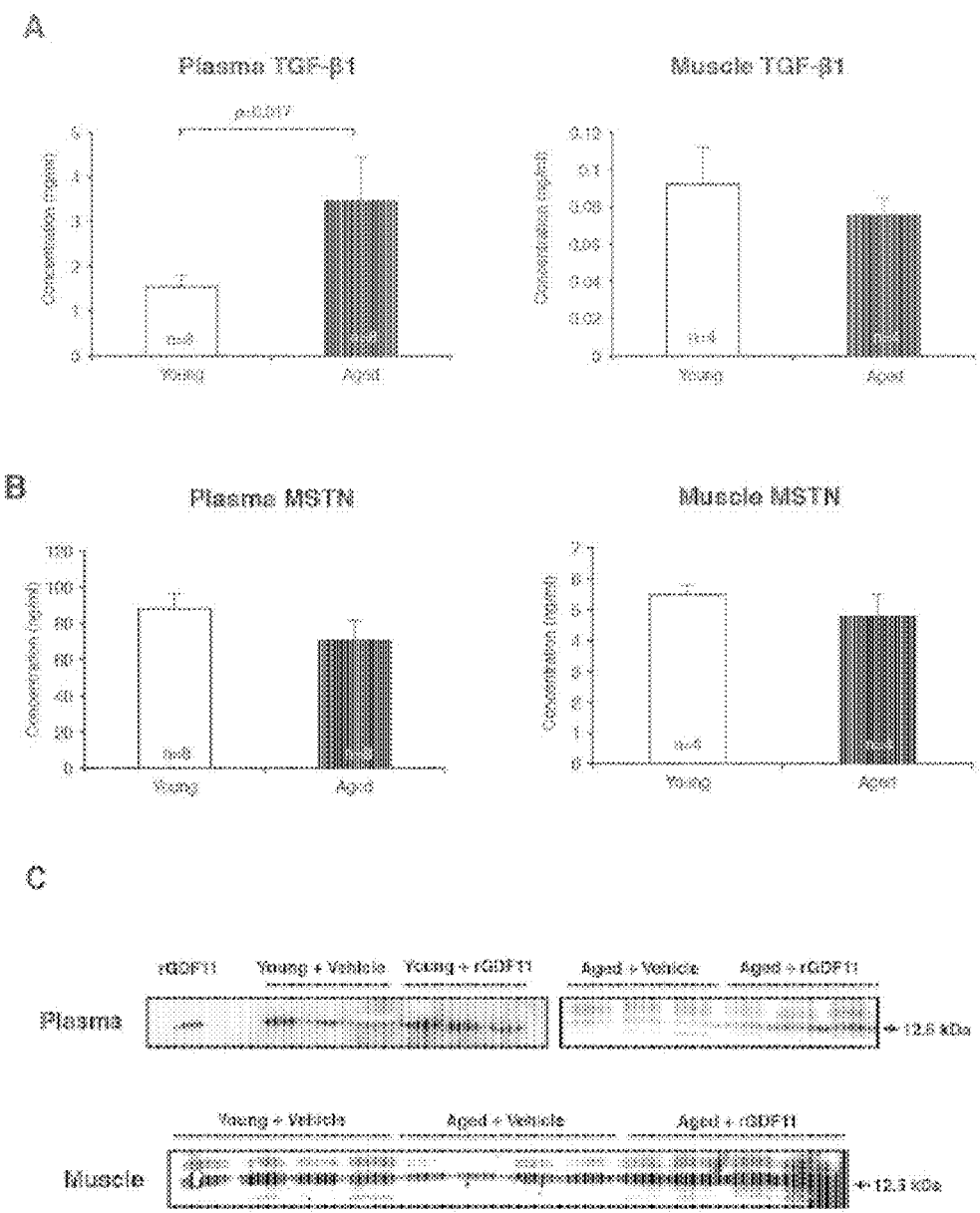
FIG. 12 depicts age-dependent alterations in local and systemic levels of TGF-ß1, myostatin and GDF11. To begin to uncover the systemic signals that restore muscle stem cell function in aged mice exposed to a youthful circulation, we searched for age variant blood-borne factors in young and aged mice, focusing particularly on TGF-β family members. (A) Levels of TGF-β1 in plasma (left panel, dilution 1:40) or crushed muscle extract (right panel, dilution 1:10) as assayed by ELISA in young and aged male mice. (B) Levels of myostatin (MSTN) in plasma (left panel, dilution 1:40) or crushed muscle extract (right panel, 1:3) as assayed by ELISA in young and aged male mice. All graphs represent mean±SEM and p-values, indicating only statistically significant differences, were calculated using t-test. (C) Western analysis of GDF11 levels in plasma and muscles of vehicle- or rGDF11-treated mice after 28 days of daily injections. Equal amounts (100 μg) of plasma proteins were loaded in each lane, with recombinant GDF11 (rGDF11) loaded at left as a control. Data is shown for 3 (top) or 4 (bottom) individual animals in each experimental category. These data demonstrate that endogenous levels of GDF11 are reduced with age in the skeletal muscle, as they are in plasma, and that rGDF11 injection for 28 days is sufficient to increase the levels of mature GDF11 (12.5 kDa) in the plasma of young and old animals (top), and in the muscle of aged mice (bottom). Plasma levels of GDF11 in aged mice administered rGDF11 at 0.1 mg/kg daily generally remained lower than those in young (2 month old) mice, thus suggesting that complete replenishment of GDF11 to youthful levels may not be essential for some of its rejuvenating effects.
Figure 13:
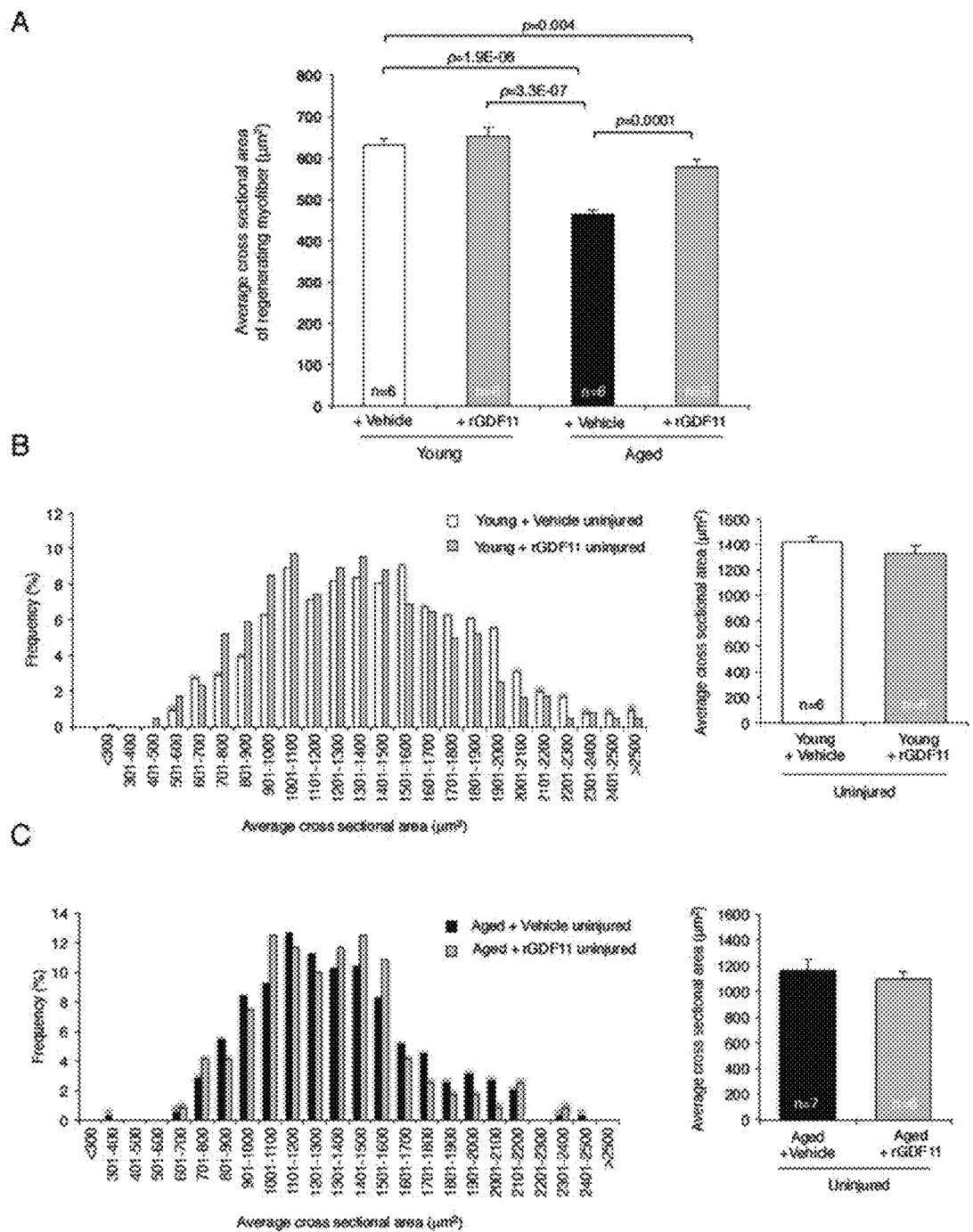
FIG. 13 illustrates that rGDF11 increases the cross sectional area of regenerating fibers in aged muscle, but does not affect the size of myofibers in uninjured muscle in young or aged mice. (A) Bar graph representing average cross-sectional area in μm$^2$ of all regenerating fibers analyzed for FIG. 3B. Number of animals used for analysis is shown within each bar. (B) Frequency distribution (left) of muscle fibers and the average cross-sectional area in μm$^2$ (right) of young contralateral control tibialis anterior (TA) muscle, which was not injured. (C) Frequency distribution (left) of muscle fibers and the average cross-sectional area in μm$^2$ (right) of aged contralateral control TA, which was not injured. Average cross-sectional area data represents mean±SEM and p-values as shown were calculated using Students t-test. Frequency distribution was analyzed by Wilcoxon exact test, and showed no statistically significant differences for young+vehicle vs. young+rGDF11 or for aged+vehicle versus aged+rGDF11, for uninjured muscles. Thus, rGDF11 stimulates accelerated recovery of myofiber size in regenerating muscle after injury, but at the doses studied here, has no impact on myofiber size or muscle mass in uninjured tissue.
Figure 14:
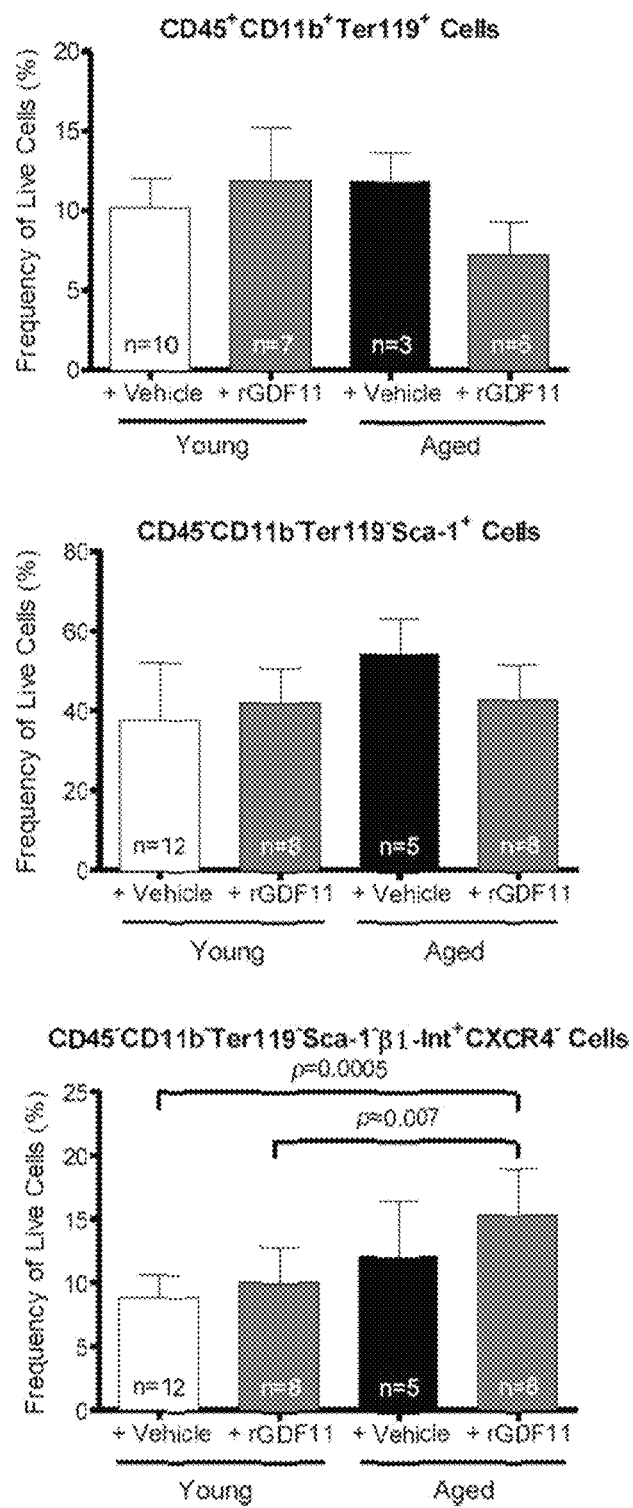
FIG. 14 shows the frequency of niche components after GDF11 treatment. Flow cytometric analysis of frequency of hematopoietic (CD45+CD11b+Ter119+), fibrogenic-adipogenic and endothelial (CD45−CD11b−Ter119−Sca-1+) or differentiated myoblast and fibroblast (CD45−CD11b−Ter119−Sca-1−ß1-Integrin+CXCR4−) cells from the skeletal muscle of young and aged mice treated with vehicle or rGDF11. Data represents mean±SD, with p-value calculated by Student's t-test and indicated only for significant differences. Treatment with rGDF11 did not induce significant changes in the frequencies of these muscle niche components in either young or aged mice.
Figure 15:
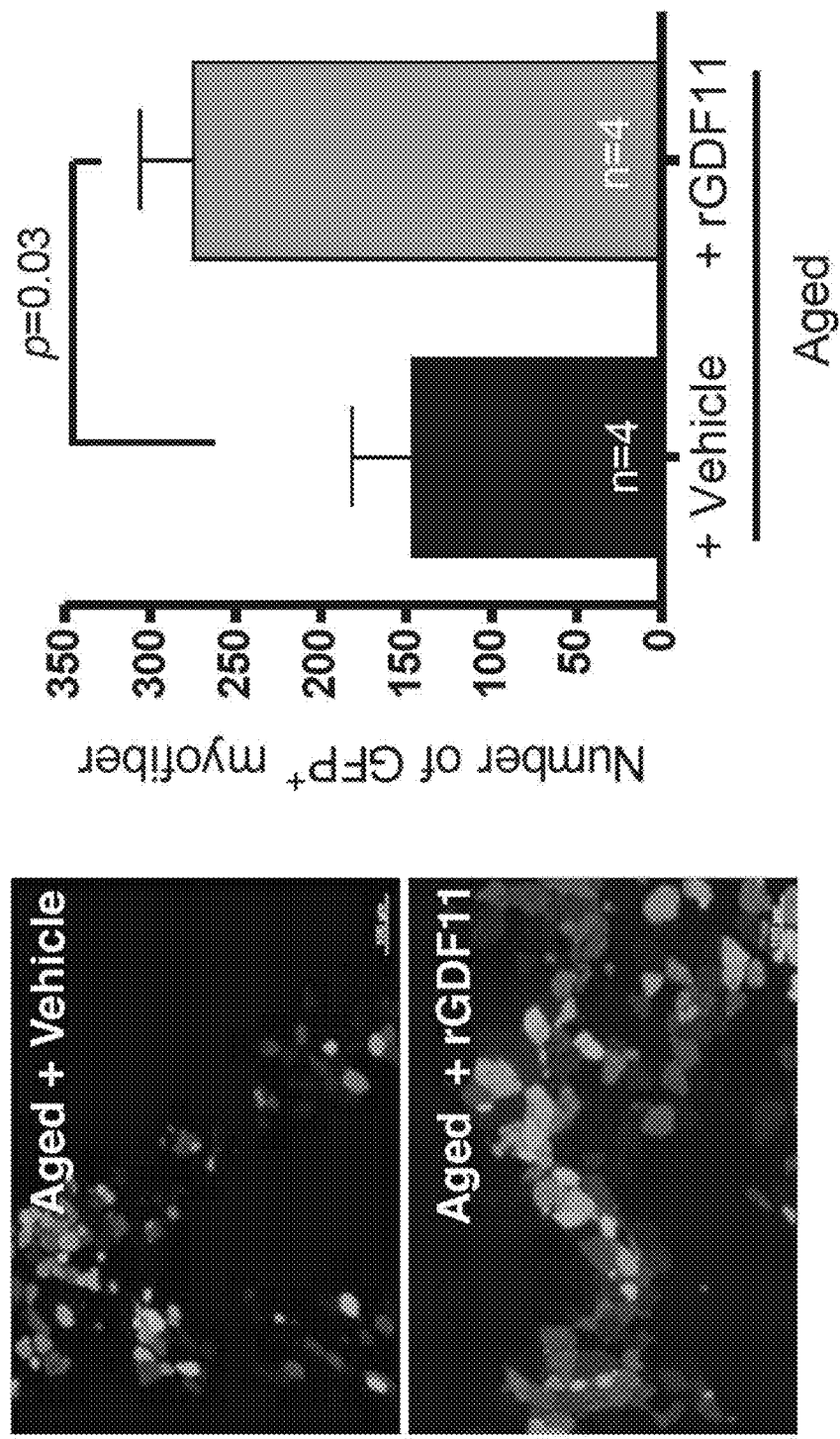
FIG. 15 shows the rejuvenation of muscle stem cells by rGDF11 supplementation. (A) Representative images of transverse cryosections of tibialis anterior (TA) muscles 2 weeks after transplantation. (B) Quantification of transplant data as maximal number of GFP+ myofibers found in each engrafted muscle. Graph represents mean±SD and p-values were calculated by Student's t-test. "n=" indicates number of mice used for each analysis.

In a recent study of aging cardiac muscle, we reported a significant decline in systemic levels of Growth Differentiation Factor 11 (GDF11), a member of the TGF-β superfamily with high homology to myostatin (MSTN), in aged mice (Loffredo et al., Cell 153:828, 2013). In contrast to GDF11, myostatin levels are unchanged and TGF-β1 increased in the plasma of aged mice (FIG. 12A and FIG. 12B, left panels). GDF11 levels decline in the muscle of aged mice as well (FIG. 12C), whereas TGF-β1 and myostatin levels are unaltered (FIG. 12A and FIG. 12B, right panels). We further showed that restoration of youthful levels of systemic GDF11 could reverse cardiac hypertrophy of aging (Loffredo et al., Cell 153:828, 2013). To determine whether supplementation of GDF11 from the young partner in heterochronic parabionts might underlie the ability of this intervention to rejuvenate aged skeletal muscle, we next performed a randomized, vehicle-controlled study in which we treated aged mice with daily intraperitoneal injection of recombinant GDF11 (rGDF11, 0.1 mg/kg mouse body weight), a dosing regimen that restores GDF11 levels in aged mice to youthful levels. After 4 weeks, a cohort of treated and control mice were challenged by cryoinjury to the tibialis anterior (TA) muscle to evaluate possible effects on muscle regeneration. Treatment with rGDF11 was continued for 7 days after injury, at which time the injured TA muscles were harvested and analyzed to determine the number and size of regenerating fibers. Remarkably, supplementation of rGDF11 in aged mice was sufficient to restore youthful profiles of myofiber caliber in regenerating muscle (FIG. 3A and FIG. 3B, p<0.05 by Stepdown Bonferroni method), indicating that systemic provision of this factor alone could recapitulate the rejuvenating effects of heterochronic parabiosis on muscle regeneration. Supplementation of rGDF11 in aged mice was also sufficient to increase the mean size of regenerating myofibers in these animals to 92% of the size of regenerating fibers in young control mice (FIG. 13A); however, rGDF11 supplementation did not alter the myofiber caliber of uninjured young or aged muscles (FIG. 13B and FIG. 13C). Consistent with the improved regenerative function of rGDF11-treated mice, satellite cell frequency (FIG. 3C) and function (FIG. 3D) increased significantly in aged muscles supplemented with systemic rGDF11 (p<0.05 by Student's t test), while other myofiber-associated mononuclear cell populations were unaffected (FIG. 14). In addition, satellite cells isolated from aged mice treated with rGDF11 showed significantly increased numbers of cells with intact nuclei (green bars, FIG. 3E, p<0.05 by Student's t test), as compared to cells harvested from aged mice receiving vehicle only for the same length of time. Moreover, the percent of freshly isolated satellite cells with severely damaged DNA (red bars, FIG. 3E) was reduced 4-fold upon treatment with rGDF11 (p<0.05 by Student's t test). In contrast to the results observed in aged mice, young mice treated with an identical regiment of rGDF11 injections showed no changes in satellite cell frequency, myogenic colony formation or DNA damage. These improvements in DNA integrity of aged satellite cells upon systemic delivery of rGDF11 produced a profile comparable to that of satellite cells isolated from untreated young mice (FIG. 3E). Thus, GDF11, which is reduced in the circulation of aged mice and restored following heterochronic parabiosis (Loffredo et al, Cell 153:828, 2013), is sufficient to restore the myogenic function and genomic integrity of aged muscle stem cells, thereby promoting regeneration of aged muscle after injury.

rGDF11 supplementation in aged mice also enhanced the regenerative capacity of satellite cells in a transplantation model, in which equal numbers of GFP-marked satellite cells were injected into the injured muscles of aged animals treated with rGDF11 or vehicle alone for 4 weeks prior and 2 weeks following transplantation. Recipients treated with rGDF11 showed almost twice as many engrafted (GFP+) fibers as vehicle-treated recipients (FIG. 15). Newly regenerated fibers in rGDF11-treated recipients were also larger in caliber (FIG. 16), consistent with the effects of rGDF11 on endogenous repair of muscle injury in aged mice (FIGS. 3A and 3B).

Figure 18:
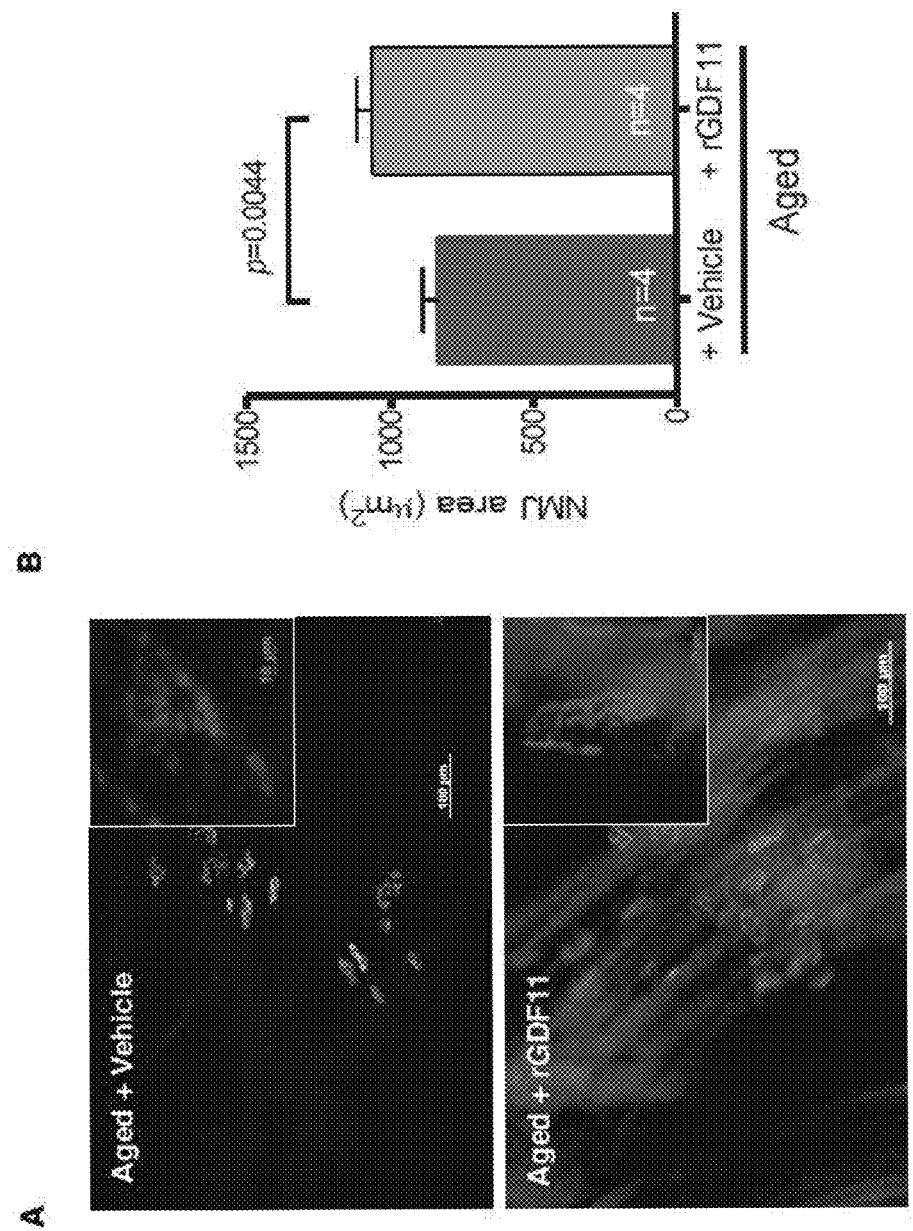
FIG. 18 shows that rGDF11 increases the size of NMJs in aged muscle. (A) Representative immunofluorescence images of neuromuscular junctions (NMJ) on tibialis anterior (TA) muscles of vehicle- or rGDF11-treated aged mice. Higher magnification (40× objective lens) of one NMJ is shown in the top right insets. Postsynaptic acetylcholine receptors are labeled with AlexaFluor 555-conjugated α-Bungarotoxin (red) and myonuclei are stained with DAPI (blue). (B) Quantification of surface area of postsynaptic acetylcholine receptors. Total number of animals used for analysis is shown within each bar as "n=". Data are presented as mean±SEM and p-values were calculated by Student's t-test.
Figure 19:
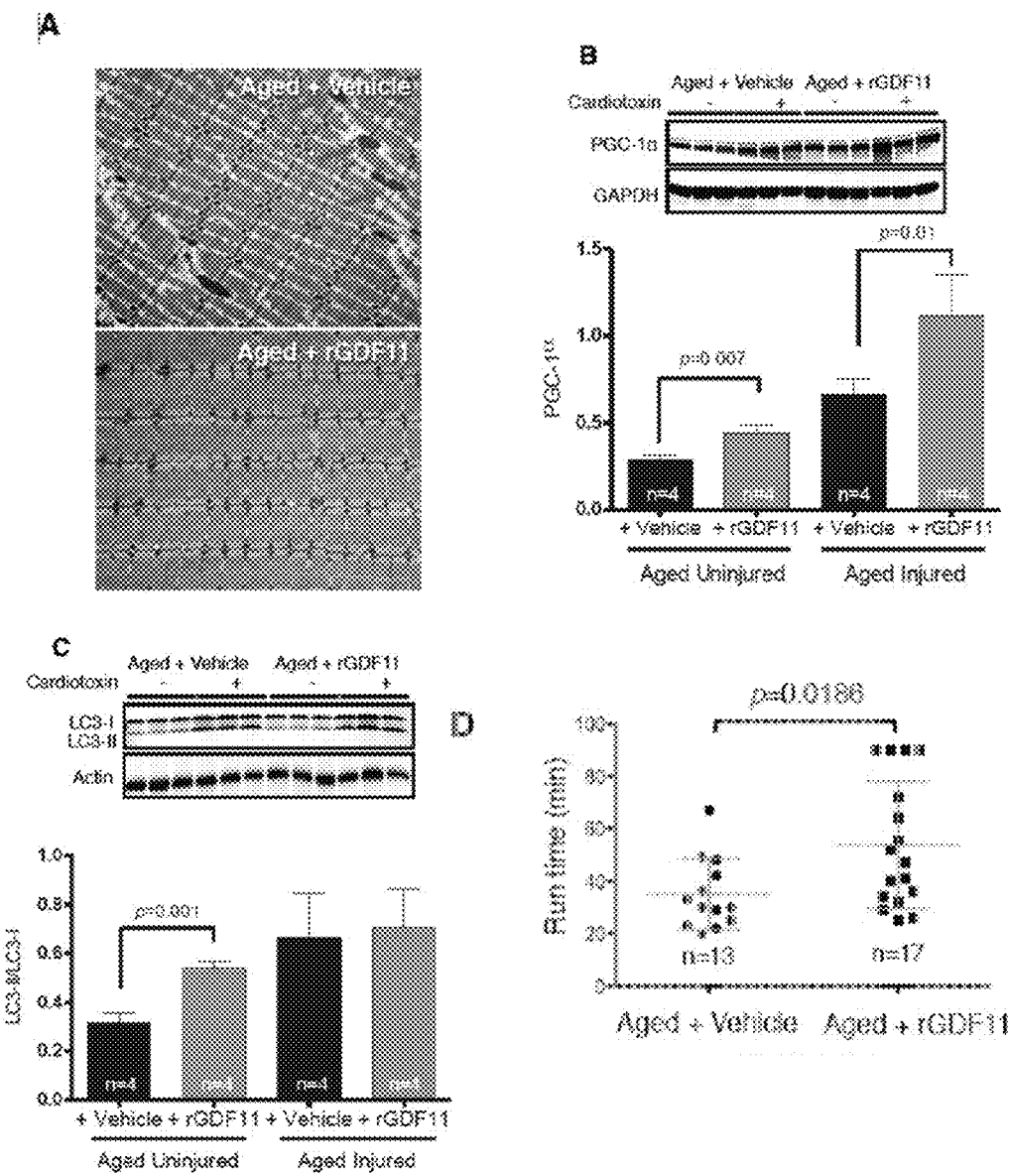
FIG. 19 illustrates improved muscle physiology and physical function after rGDF11 supplementation. (A) Electron micrographs of transverse sections of tibialis anterior (TA) muscle from vehicle or rGDF11-treated aged mice (representative of n=4 per group). Arrows indicate swollen mitochondria. (B, C) Western blot of PGC-la (B) and LC3 forms I and II (C) in TA muscle extracts from cardiotoxin-injured or uninjured vehicle- or rGDF11-treated aged mice. Three animals are shown for each experimental group. Densitometric quantification of Western data are provided below each blot, normalized to GAPDH (B) or Actin (C). (D) Scatter plots of exercise endurance, maximum treadmill runtime in a 90 minute window of vehicle- or rGDF11-treated aged mice. Data are presented for individual mice (black symbols) overlaid with mean±SD (orange lines) and p-values were calculated by Mann-Whitney analysis. "n=" indicates number of mice used for each analysis.

The present investigators next interrogated the mechanistic basis for rGDF11's effects on aged muscle. Although no alterations in gross anatomy were observed on body weight, fat mass, or muscle mass (FIG. 17), immunofluorescence analysis demonstrated increases in the size of neuromuscular junctions (NMJ) following rGDF11 treatment (FIG. 18). In addition, electron microscopy of uninjured muscle revealed striking improvements of myofibrillar and mitochondrial morphology in aged mice treated with rGDF11 (FIG. 19A). Treated muscles showed reduction of atypical and swollen mitochondria, reduced accumulation of vacuoles, and restoration of regular sarcomeric and interfibrillar mitochondrial patterning (FIG. 19A). Consistent with these ultrastructural improvements, levels of Peroxisome proliferator-activated receptor gamma co-activator 1α (PGC-1α), a master regulator of mitochondrial biogenesis, were increased in the muscle of aged rGDF11-treated mice (FIG. 19B), suggesting that GDF11 may affect mitochondrial dynamics of fission and fusion to generate new mitochondria. Consistent with this notion, in vitro treatment of differentiating cultures of aged satellite cells with rGDF11 yielded increased numbers of multi-nucleated myotubes exhibiting greater mitochondrial content and enhanced mitochondrial function (FIG. 20). Finally, we observed increased basal levels of autophagosome (macroautophagy) markers (assessed as the ratio of autophagic intermediates LC3-II over LC3-I), in the uninjured skeletal muscle of rGDF11-treated aged animals (FIG. 19C). Collectively, these data suggest enhanced autophagy/mitophagy and mitochondrial biogenesis as likely explanations for the cellular remodeling of muscle fibers in rGDF11-treated aged mice.

Figure 21:
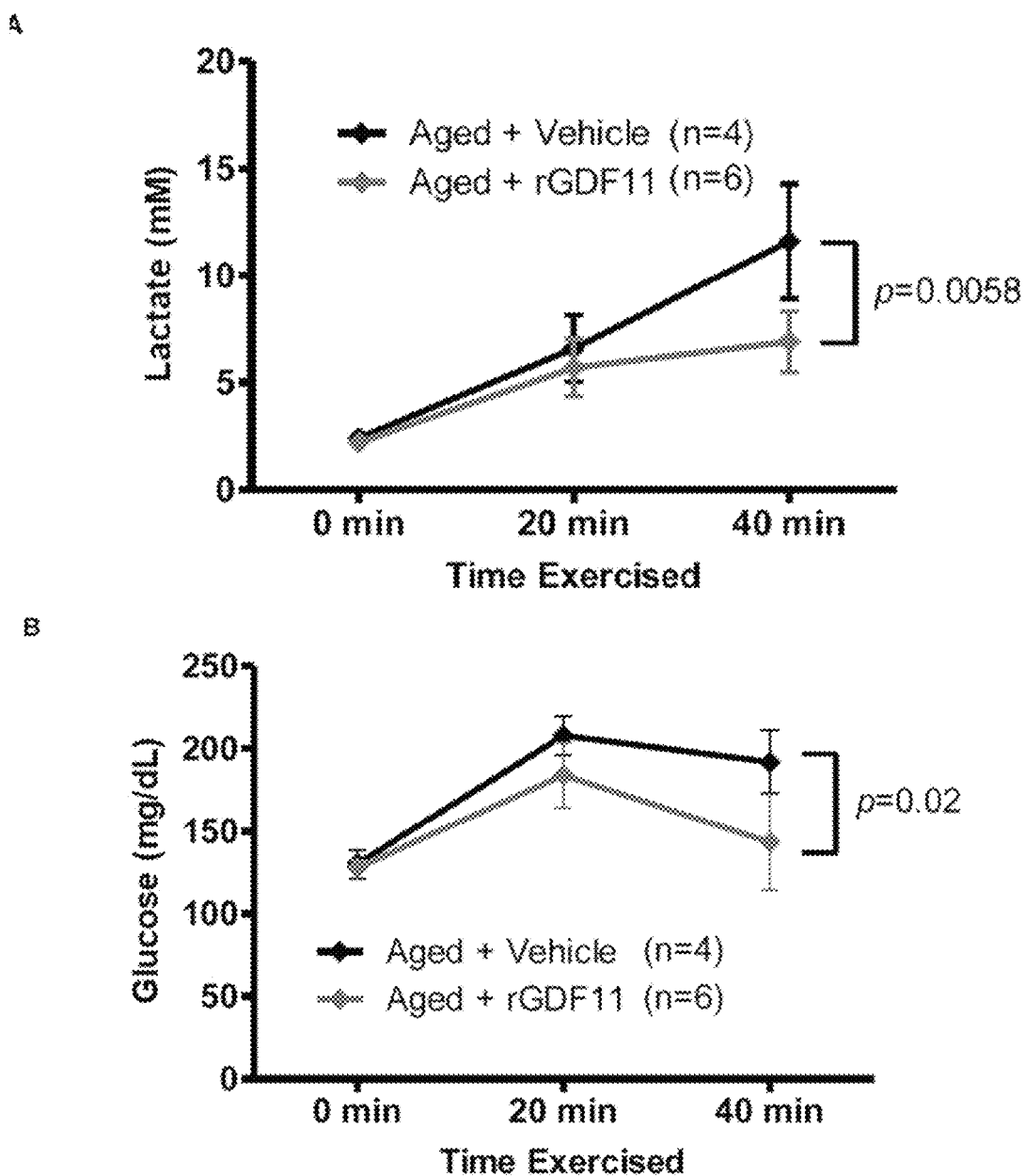
FIG. 21 illustrates increased lactate clearance and decreased glucose levels during exercise in aged mice treated with rGDF11. (A, B) Quantification of blood lactate (A) or glucose (B) levels of vehicle- (black line) or rGDF11- (grey line) treated aged mice, sampled at the indicated times during treadmill exercise, as in FIG. 19D. Data are presented as mean±SD. Total number of animals used for analysis is shown within parenthesis as "n=" and p-values were calculated by Student's t-test.
Figure 22:
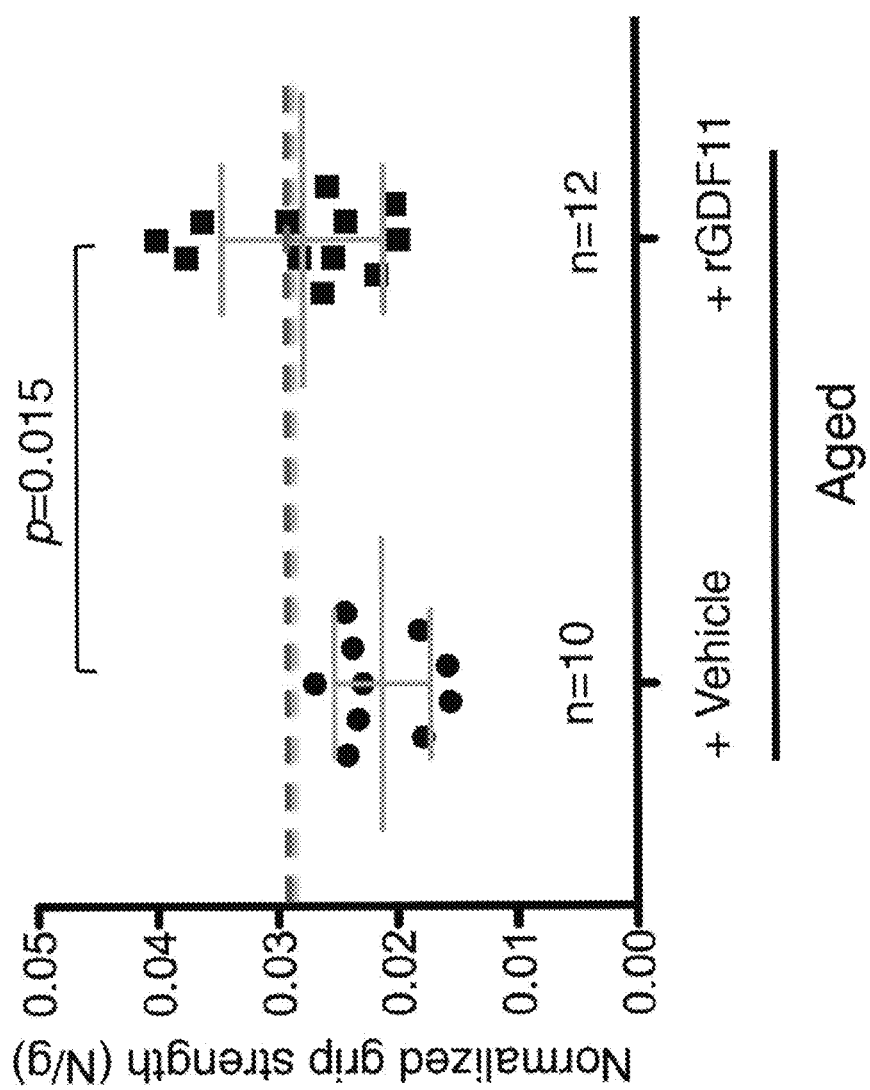
FIG. 22 illustrates the improved grip strength of aged mice upon rGDF11 supplementation. Scatter plot of forelimb grip-strength of vehicle- or rGDF11-treated aged mice plotted as maximum force normalized to body weight (Newton/gram (N/g)) exerted in triplicate trials. Red line represents the normalized maximum grip-strength of 33-39 week-old young male mice. Data are presented for individual mice (black symbols) overlaid with mean±SD (orange lines) and p-value calculated by Mann-Whitney analysis, and "n=" indicates number of mice used for this analysis. Aged mice treated with rGDF11 show increased normalized grip strength.

The present investigators next questioned whether improvements in muscle ultrastructure and mitochondrial turnover in rGDF11-treated aged mice might translate into improved physical function in exercise endurance and grip strength analyses. Aged mice treated with rGDF11 showed increased average exercise endurance (35 min. vs. 57 min.), despite variation in the responses of individual animals (FIG. 19D). rGDF11-treated animals also exhibited improved clearance of systemic lactate (FIG. 21A) and lower levels of glucose (FIG. 21B) after 40 minutes of strenuous running, providing additional evidence indirectly supporting improved mitochondrial function in aged rGDF11-treated animals. Finally, in accord with rGDF11-stimulated remodeling of myofiber ultrastructure, rGDF11-treated animals exhibited increased average grip strength (FIG. 22) in a standardized testing platform (Hakim, et al., *Methods Mol Biol* 709: 75, 2011).

The studies reported here establish GDF11 as a novel hormonal regulator of youthfulness and regenerative potential and demonstrate that restoration of aged satellite cell function by this factor is coincident with reversal of accumulated DNA damage. Restoring this factor to youthful levels in the blood, either through heterochronic parabiosis or direct injection in vivo, reverses age-dependent dysfunction of satellite cells and restores robust muscle repair in aged mice. Remarkably, restoration of function of aged satellite cells is accompanied by reversal of accumulated DNA damage, suggesting that genome toxicity may constrain stem cell function in aged skeletal muscle.

Figure 23:
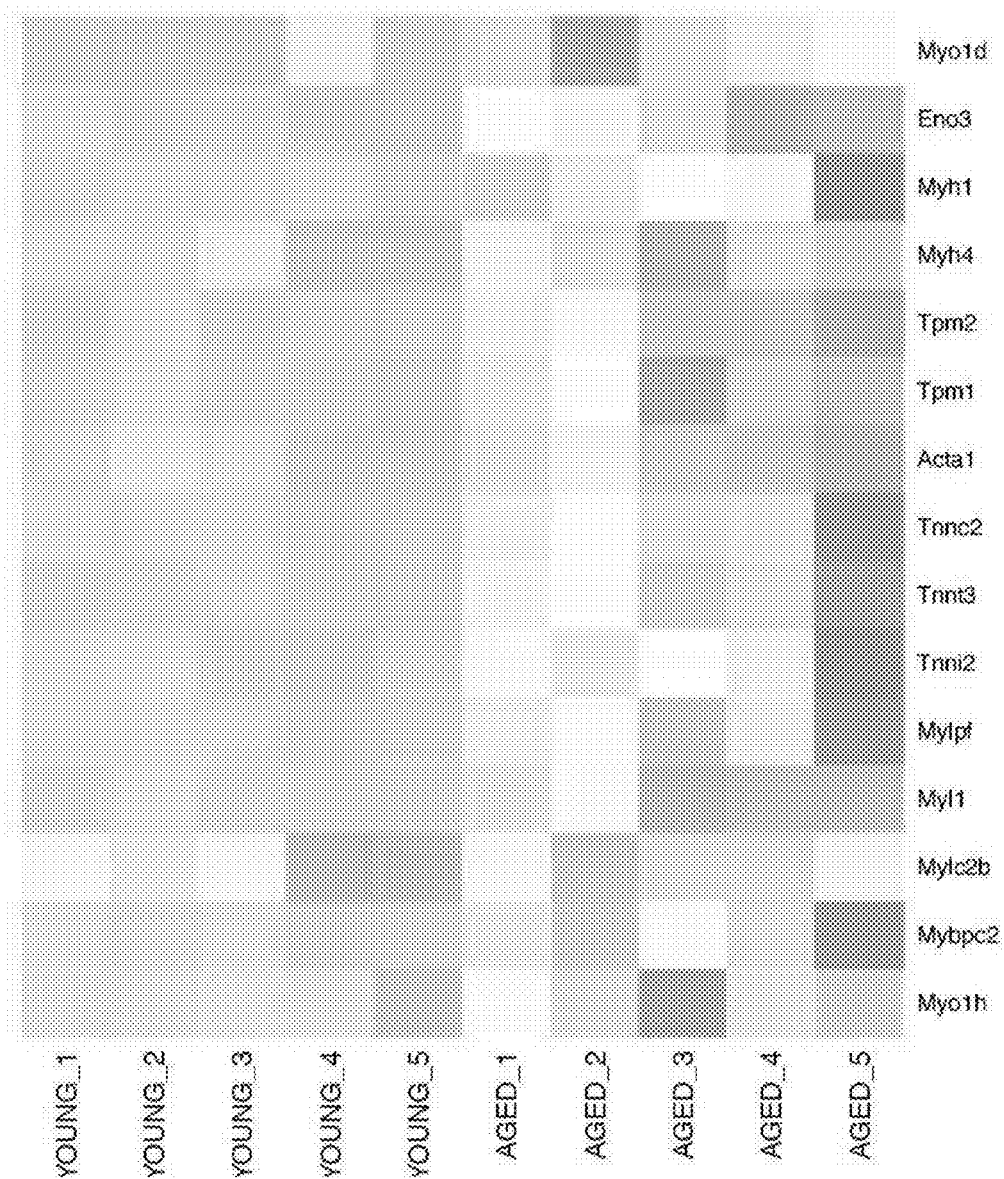
FIG. 23 is a heat map representation of differentially expressed myogenic genes in freshly isolated aged satellite cells. Data are represented in a gradient of blue to pink (blue indicating low and pink indicating high level of expression), for FACS-isolated young (2 mo. of age, left columns) or aged (22-24 mo. of age, right columns) satellite cells (n=5 independent samples per group). Individual gene symbols are indicated on the right in young and aged satellite cells. Aged satellite cells generally show an increase in myogenic gene expression.
Figure 24:
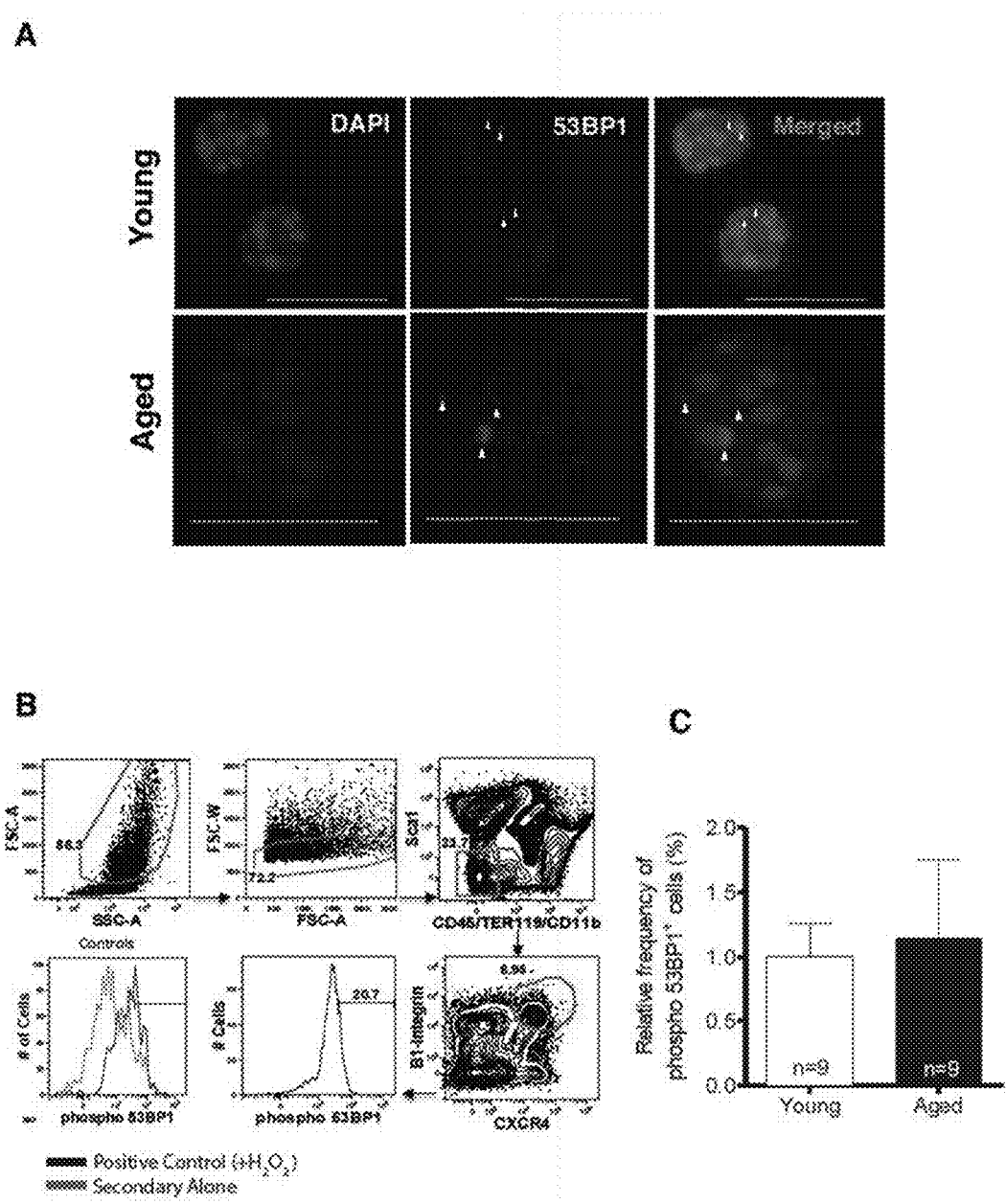
FIG. 24 illustrates similar detection of 53BP1 and phosphorylated-53BP1 in young and aged satellite cells. (A) Representative confocal immunofluorescence images (sums of z-stacks) of 53BP1 foci (marked with white arrowheads) of young and aged satellite cells as indicated. Scale bar=10 μm. (B) Representative flow plots from analysis of a young mouse illustrating gating strategy for flow cytometric analysis of phospho-53BP1 in CD45−Sca-1−CD11b−Ter119−CXCR4+β1-Integrin+ satellite cells. (C) Quantification of flow cytometric analysis presented as frequency of phosphorylated-53BP1+ satellite cells among total satellite cells from young or aged animals (n=9 animals per group). Data were normalized to the average frequency of phosphorylated-53BP1+ satellite cells for young mice and are presented as relative mean±SD. Differences were not statistically significant, calculated using Mann-Whitney analysis.
Figure 25:
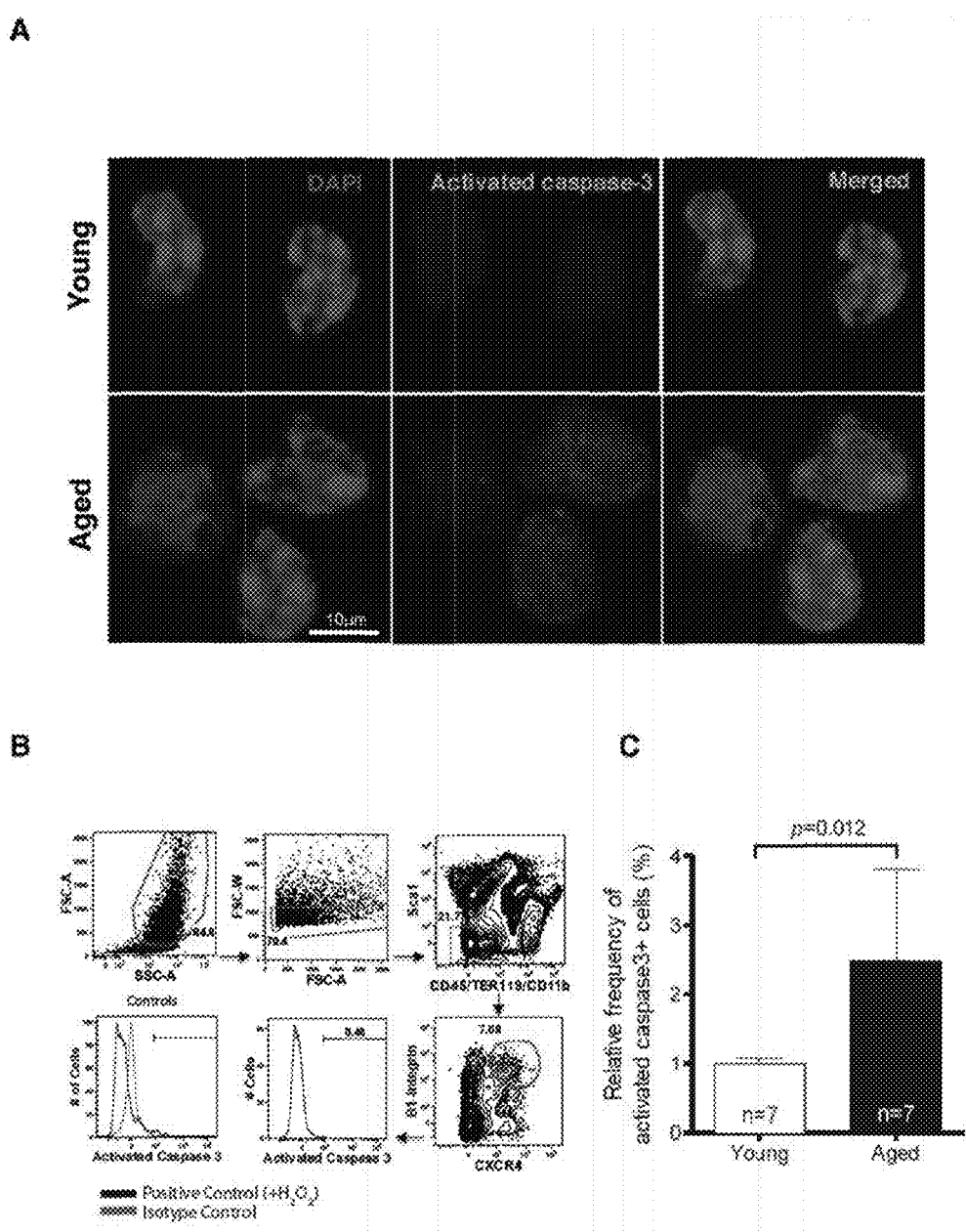
FIG. 25 illustrates increased immunoreactivity to activated caspase-3 in aged satellite cell nuclei. (A) Representative confocal (sums of z-stacks) immuno-fluorescent images of activated caspase-3 staining in satellite cells harvested from young or aged mice. Scale bar=10 µm. (B) Representative flow plots from a young mouse illustrating gating strategy for flow cytometric analysis of activated caspase-3 in CD45−Sca-1−CD11b−Ter119−CXCR4+β1-Integrin+ satellite cells. (C) Quantification of flow cytometric analysis presented as frequency of activated caspase3+ satellite cells among total satellite cells from young or aged animals (n=7 animals per group). Data were normalized to the average frequency of activated caspase3+ satellite cells for young mice and are presented as relative mean±SD and p-value was calculated using Mann-Whitney analysis.
Figure 26:
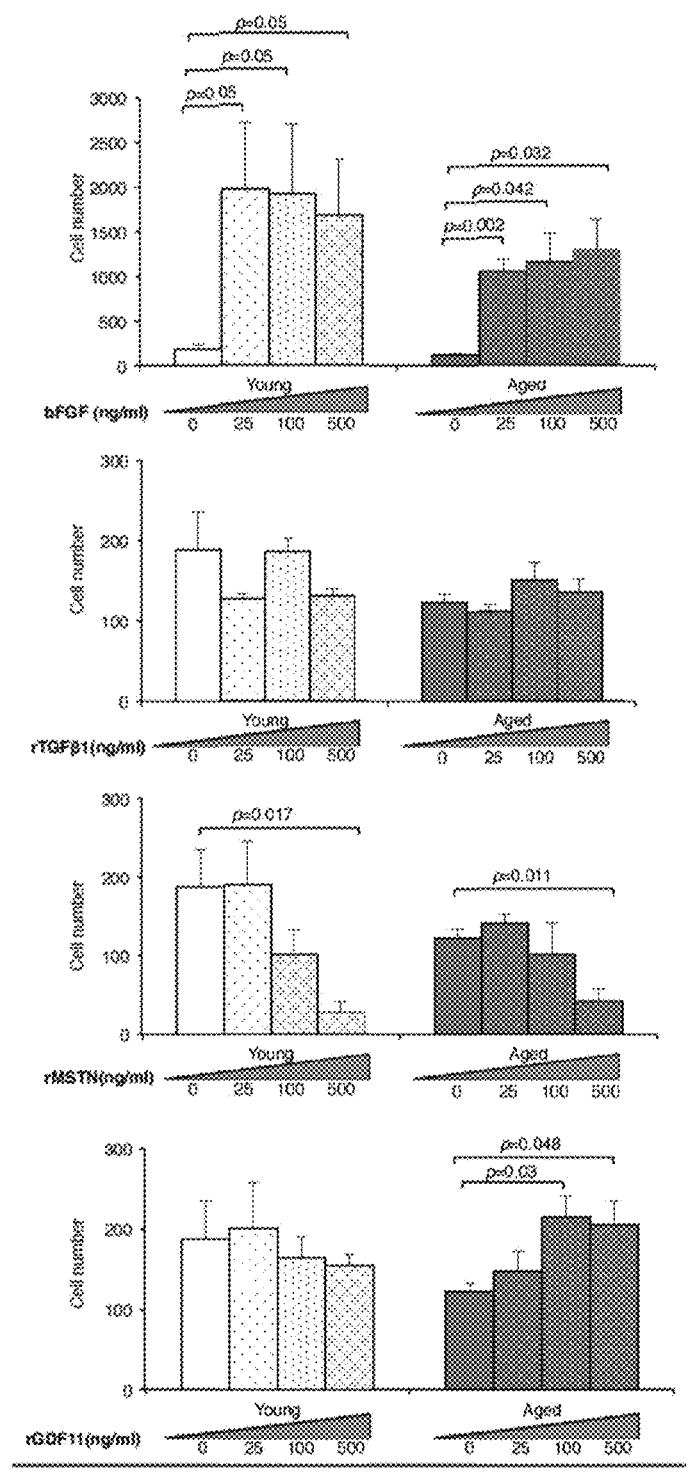
FIG. 26 shows the effects of bFGF, rTGF-β1, rMSTN and rGDF11 on satellite cell proliferation in vitro. Quantification of cell number after in vitro culture of satellite cells for 5 days in presence of indicated concentrations of bFGF, or recombinant TGF-β1, recombinant MSTN, or rGDF11 (as indicated). 200 double sorted satellite cells per well (>98% purity) from young (8-12 weeks) or aged (24 mo.) mice were seeded initially and cultured in growth medium containing 20% knock-out serum replacement lacking members of the TGF-β superfamily of growth factors. Data presented as mean±SD and p-values calculated by Student's t-test, are shown only for statistically significant differences.

Interestingly, recent studies also indicate that directed genome-wide DNA strand breaks are a conserved and necessary event for cell differentiation associated genome reprogramming (Larsen et al. *Proc Natl Acad Sci USA* 2010; 107, 4230). Transcriptome profiling of young and aged muscle stem cells indicates that some muscle differentiation genes are up-regulated in aged satellite cells (FIG. 23), despite the fact that aged cells show compromised regenerative capacity. In addition, the present investigators failed to detect age-related alterations in expression of DNA damage recognition and repair enzymes by immunofluorescence analysis (FIG. 24). These data raise the intriguing possibility that aged satellite cells display an apparent increase in DNA damage because they are arrested at an early stage of myogenesis, in which differentiation-associated DNA strand breaks have been induced but not resolved. Extending this logic, systemic "rejuvenation" by parabiosis or rGDF11 treatment may release these cells from this age-induced differentiation block. This notion is consistent with our data demonstrating (i) increased detection of DNA damage and an increase in activated cleaved-Caspase3 in aged satellite cells (FIG. 25), (ii) the resolution of these changes upon restoration of myogenic activity in "rejuvenated" muscle, and (iii) the ability of in vitro treatment with rGDF11 to increase myogenic cell number and promote myotube formation in cultures of aged satellite cells (FIG. 26). Given that rGDF11-stimulated rejuvenation of aged satellite cells coincides with remodeling of the aged satellite cell niche, the present investigators speculate that increasing GDF11 levels in aged mice may act both directly and indirectly to restore satellite cell regenerative function, stimulating intrinsic changes in satellite cell differentiation capacity and producing a more pro-myogenic niche that extrinsically supports endogenous regeneration and transplant-associated myogenic engraftment.

As noted earlier, the aged muscles and muscle-resident stem cells in 24-month aged animals are not also senescent (FIG. 6) in our hands. Thus, it is possible that the old muscle stem cells are arrested in an early stage of myogenesis, at which differentiation-associated DNA strand breaks have already been induced, resulting in the increased comet structures upon single cell gel electrophoresis. Due to age-related deficiencies in signaling, we postulate that these cells are unable to proceed to complete differentiation, and therefore are lacking in their regeneration capacity. Based on these observations, we speculate that systemic GDF11, which declines with age, may be required for proper myogenic progression of activated satellite cells.

GDF11 belongs to a conserved family of growth factors that regulate diverse cellular processes. Genetic deficiency of GDF11 in mice causes profound developmental abnormalities, including agenesis of the kidneys, and perinatal lethality. The mature form of GDF11 shares approximately 90% sequence identity with myostatin (MSTN), known for its potent negative influence on skeletal muscle mass, and binds the same receptors (ACVR1B/ALK4, ACVR1A/ALK5 and ACVR1C/ALK7). A prior study reported relatively low levels of ALK4/5 expression by postnatal (P12) satellite cells and failed to detect a difference in proliferation of these cells upon exposure to MSTN (Kim, et al., *Science*, 308:1927, 2005). The present investigators have found that in vitro exposure of aged satellite cells to rGDF11, but not recombinant MSTN or TGF-β1, produced dose responsive increases in cell proliferation (FIG. 26) and differentiation (FIG. 20A), suggesting that GDF11, in contrast to MSTN, can act directly on satellite cells to alter their function. Interestingly, growth promotion may be the primordial role of MSTN/GDF11, as invertebrates possess only a single ortholog of the MSTN/GDF11 family, and down-regulation of this gene results in retarded growth (De Santis, et al., *J Exp Biol* 214: 2671, 2011). In any event, the unique combination of rGDF11's pro-myogenic effects in skeletal muscle, anti-hypertrophic effects in the heart (Loffredo, et al., Cell 153: 828, 2013), and beneficial effects on neurogenesis and neuronal function in aged mice, should encourage further investigation of its therapeutic potential for a variety of age-related diseases and suggests that GDF11 should be regarded as a new molecular regulator of mammalian aging with potentially broad-reaching applications.

In summary, considering the therapeutic aspect of the studies reported here, the ability of age-regulated circulating factor GDF11 to reversibly modulate stem cell activity and stem cell mediated regeneration takes us a step forward towards developing new strategies to maintain youthful stem cell function and tissue homeostasis.

REFERENCES

1. L. Liu, T. A. Rando, Manifestations and mechanisms of stem cell aging. *The Journal of cell biology* 193, 257 (Apr. 18, 2011).
2. A. J. Wagers, I. M. Conboy, Cellular and molecular signatures of muscle regeneration: current concepts and controversies in adult myogenesis. *Cell* 122, 659 (Sep. 9, 2005).

3. J. M. Ruckh et al., Rejuvenation of regeneration in the aging central nervous system. *Cell Stem Cell* 10, 96 (Jan. 6, 2012).
4. Y. C. Jang, M. Sinha, M. Cerletti, C. Dall'Osso, A. J. Wagers, Skeletal muscle stem cells: effects of aging and metabolism on muscle regenerative function. *Cold Spring Harb Symp Quant Biol* 76, 101 (2011).
5. R. I. Sherwood et al., Isolation of adult mouse myogenic progenitors: functional heterogeneity of cells within and engrafting skeletal muscle. *Cell* 119, 543 (Nov. 12, 2004).
6. M. Cerletti, Y. C. Jang, L. W. Finley, M. C. Haigis, A. J. Wagers, Short-term calorie restriction enhances skeletal muscle stem cell function. *Cell Stem Cell* 10, 515 (May 4, 2012).
7. I. M. Conboy et al., Rejuvenation of aged progenitor cells by exposure to a young systemic environment. *Nature* 433, 760 (Feb. 17, 2005).
8. J. V. Chakkalakal, K. M. Jones, M. A. Basson, A. S. Brack, The aged niche disrupts muscle stem cell quiescence. *Nature* 490, 355 (Oct. 18, 2012).
9. A. C. McPherron, Metabolic Functions of Myostatin and Gdf11. *Immunol Endocr Metab Agents Med Chem* 10, 217 (December, 2010).
10. B. D. Larsen et al., Caspase 3/caspase-activated DNase promote cell differentiation by inducing DNA strand breaks. *Proc Natl Acad Sci USA* 107, 4230 (Mar. 2, 2010).
11. A. C. McPherron, T. V. Huynh, S. J. Lee, Redundancy of myostatin and growth/differentiation factor 11 function. *BMC Dev Biol* 9, 24 (2009).

What is claimed is:

1. A method of rejuvenating skeletal muscle stem cells in a subject in need thereof, comprising administering to the subject a composition which increases the level or activity of GDF11 polypeptide in the subject, wherein the composition comprises a GDF11 polypeptide or a functional fragment or functional variant thereof, wherein the functional fragment comprises at least the 12.5 kDa C-terminus of GDF11, and wherein the functional variant has at least 90% sequence identity to full length human mature GDF11, and wherein the composition causes the subject's skeletal muscle stem cells to increase in frequency or number, increase the sizes of regenerating myofibers, increase the efficiency of myogenic colony formation, increase the percentage of intact nuclei, and decrease the percentage of severely damaged deoxyribonucleic acid (DNA), thereby rejuvenating the skeletal muscle stem cells in the subject.

2. The method of claim 1, wherein the level or activity of GDF11 polypeptide is increased in the skeletal muscle tissue of the subject.

3. The method of claim 1, wherein the composition comprises a GDF11 polypeptide comprising the amino acid sequence of human mature GDF11.

4. The method of claim 1, wherein the composition comprises a GDF11 polypeptide comprising the amino acid sequence of human GDF11 pro-peptide.

5. The method of claim 1, wherein the composition comprises a GDF11 polypeptide comprising the amino acid sequence of human GDF11 precursor polypeptide.

6. The method of claim 1, wherein the subject has been diagnosed with a skeletal muscle condition due to aging.

7. A method of increasing strength or exercise endurance capacity in a subject in need thereof, comprising administering to the subject a composition which increases the level or activity of GDF11 polypeptide in the subject, thereby increasing the strength or exercise endurance capacity, wherein the composition comprises a GDF11 polypeptide or a functional fragment or functional variant thereof, wherein the functional fragment comprises at least the 12.5 kDa C-terminus of GDF11, wherein the functional variant has at least 90% sequence identity to full length human mature GDF11, and wherein the composition causes the subject's skeletal muscle stem cells to increase in frequency or number, increase the sizes of regenerating myofibers, increase the efficiency of myogenic colony formation, increase the percentage of intact nuclei, and decrease the percentage of severely damaged deoxyribonucleic acid (DNA), thereby rejuvenating the skeletal muscle stem cells in the subject.

8. The method of claim 7, wherein the composition comprises a GDF11 polypeptide comprising the amino acid sequence of human mature GDF11.

9. The method of claim 7, wherein the composition comprises a GDF11 polypeptide comprising the amino acid sequence of human GDF11 pro-peptide.

10. The method of claim 7, wherein the composition comprises a GDF11 polypeptide comprising the amino acid sequence of human GDF11 precursor polypeptide.

11. A method of treating or preventing a skeletal muscle condition in a subject in need thereof, comprising administering to the subject an effective amount of a composition which increases the level or activity of GDF11 polypeptide in the subject, wherein the composition causes the subject's skeletal muscle stem cells to increase in frequency or number, increase the sizes of regenerating myofibers, increase the efficiency of myogenic colony formation, increase the percentage of intact nuclei, and decrease the percentage of severely damaged DNA, thereby treating or preventing the skeletal muscle condition in the subject, wherein the composition comprises a GDF11 polypeptide or a functional fragment or functional variant thereof, wherein the functional fragment comprises at least the 12.5 kDa C-terminus of GDF11, and wherein the functional variant has at least 90% sequence identity to full length human mature GDF11.

12. The method of claim 11, wherein the skeletal muscle condition is selected from the group consisting of atrophy, bony fractures associated with muscle wasting or weakness, cachexia, denervation, diabetes, dystrophy, exercise-induced skeletal muscle fatigue, fatigue, frailty, inflammatory myositis, metabolic syndrome, neuromuscular disease, obesity, post-surgical muscle weakness, post-traumatic muscle weakness, sarcopenia, toxin exposure, wasting, and weakness.

13. The method of claim 11, wherein the compositions comprises a GDF11 polypeptide selected from the group consisting of a human GDF11 precursor polypeptide, a human GDF11 pro-peptide, and a human mature GDF11 and a human GDF11 N-terminal polypeptide.

14. The method of claim 11, wherein the composition comprises homodimers of GDF11 polypeptides, and wherein the GDF11 polypeptides are selected from the group consisting of a human GDF11 precursor polypeptide, a human GDF11 pro-peptide, and a human mature GDF11 and a human GDF11 N-terminal polypeptide.

* * * * *

SEQUENCE LISTING

```
<160> NUMBER OF SEQ ID NOS: 3

<210> SEQ ID NO 1
<211> LENGTH: 407
<212> TYPE: PRT
<213> ORGANISM: Homo sapiens

<400> SEQUENCE: 1

Met Val Leu Ala Ala Pro Leu Leu Leu Gly Phe Leu Leu Leu Ala Leu
1               5                   10                  15

Glu Leu Arg Pro Arg Gly Glu Ala Ala Glu Gly Pro Ala Ala Ala Ala
            20                  25                  30

Ala Ala Ala Ala Ala Ala Ala Ala Gly Val Gly Gly Glu Arg Ser
        35                  40                  45

Ser Arg Pro Ala Pro Ser Val Ala Pro Glu Pro Asp Gly Cys Pro Val
    50                  55                  60

Cys Val Trp Arg Gln His Ser Arg Glu Leu Arg Leu Glu Ser Ile Lys
65                  70                  75                  80

Ser Gln Ile Leu Ser Lys Leu Arg Leu Lys Glu Ala Pro Asn Ile Ser
                85                  90                  95

Arg Glu Val Val Lys Gln Leu Leu Pro Lys Ala Pro Pro Leu Gln Gln
            100                 105                 110

Ile Leu Asp Leu His Asp Phe Gln Gly Asp Ala Leu Gln Pro Glu Asp
        115                 120                 125

Phe Leu Glu Glu Asp Glu Tyr His Ala Thr Thr Glu Thr Val Ile Ser
    130                 135                 140

Met Ala Gln Glu Thr Asp Pro Ala Val Gln Thr Asp Gly Ser Pro Leu
145                 150                 155                 160

Cys Cys His Phe His Phe Ser Pro Lys Val Met Phe Thr Lys Val Leu
                165                 170                 175

Lys Ala Gln Leu Trp Val Tyr Leu Arg Pro Val Pro Arg Pro Ala Thr
            180                 185                 190

Val Tyr Leu Gln Ile Leu Arg Leu Lys Pro Leu Thr Gly Glu Gly Thr
        195                 200                 205

Ala Gly Gly Gly Gly Gly Arg Arg His Ile Arg Ile Arg Ser Leu
    210                 215                 220

Lys Ile Glu Leu His Ser Arg Ser Gly His Trp Gln Ser Ile Asp Phe
225                 230                 235                 240

Lys Gln Val Leu His Ser Trp Phe Arg Gln Pro Gln Ser Asn Trp Gly
```

```
            245                 250                 255
Ile Glu Ile Asn Ala Phe Asp Pro Ser Gly Thr Asp Leu Ala Val Thr
            260                 265                 270

Ser Leu Gly Pro Gly Ala Glu Gly Leu His Pro Phe Met Glu Leu Arg
            275                 280                 285

Val Leu Glu Asn Thr Lys Arg Ser Arg Arg Asn Leu Gly Leu Asp Cys
            290                 295                 300

Asp Glu His Ser Ser Glu Ser Arg Cys Cys Arg Tyr Pro Leu Thr Val
305                 310                 315                 320

Asp Phe Glu Ala Phe Gly Trp Asp Trp Ile Ile Ala Pro Lys Arg Tyr
                    325                 330                 335

Lys Ala Asn Tyr Cys Ser Gly Gln Cys Glu Tyr Met Phe Met Gln Lys
                    340                 345                 350

Tyr Pro His Thr His Leu Val Gln Gln Ala Asn Pro Arg Gly Ser Ala
                    355                 360                 365

Gly Pro Cys Cys Thr Pro Thr Lys Met Ser Pro Ile Asn Met Leu Tyr
                    370                 375                 380

Phe Asn Asp Lys Gln Gln Ile Ile Tyr Gly Lys Ile Pro Gly Met Val
385                 390                 395                 400

Val Asp Arg Cys Gly Cys Ser
                    405

<210> SEQ ID NO 2
<211> LENGTH: 375
<212> TYPE: PRT
<213> ORGANISM: Homo sapiens

<400> SEQUENCE: 2

Met Gln Lys Leu Gln Leu Cys Val Tyr Ile Tyr Leu Phe Met Leu Ile
1               5                   10                  15

Val Ala Gly Pro Val Asp Leu Asn Glu Asn Ser Glu Gln Lys Glu Asn
            20                  25                  30

Val Glu Lys Glu Gly Leu Cys Asn Ala Cys Thr Trp Arg Gln Asn Thr
        35                  40                  45

Lys Ser Ser Arg Ile Glu Ala Ile Lys Ile Gln Ile Leu Ser Lys Leu
    50                  55                  60

Arg Leu Glu Thr Ala Pro Asn Ile Ser Lys Asp Val Ile Arg Gln Leu
65                  70                  75                  80

Leu Pro Lys Ala Pro Pro Leu Arg Glu Leu Ile Asp Gln Tyr Asp Val
                85                  90                  95

Gln Arg Asp Asp Ser Ser Asp Gly Ser Leu Glu Asp Asp Tyr His
            100                 105                 110

Ala Thr Thr Glu Thr Ile Ile Thr Met Pro Thr Glu Ser Asp Phe Leu
        115                 120                 125

Met Gln Val Asp Gly Lys Pro Lys Cys Cys Phe Phe Lys Phe Ser Ser
    130                 135                 140

Lys Ile Gln Tyr Asn Lys Val Val Lys Ala Gln Leu Trp Ile Tyr Leu
145                 150                 155                 160

Arg Pro Val Glu Thr Pro Thr Thr Val Phe Val Gln Ile Leu Arg Leu
                165                 170                 175

Ile Lys Pro Met Lys Asp Gly Thr Arg Tyr Thr Gly Ile Arg Ser Leu
            180                 185                 190

Lys Leu Asp Met Asn Pro Gly Thr Gly Ile Trp Gln Ser Ile Asp Val
        195                 200                 205
```

```
Lys Thr Val Leu Gln Asn Trp Leu Lys Gln Pro Glu Ser Asn Leu Gly
    210                 215                 220

Ile Glu Ile Lys Ala Leu Asp Glu Asn Gly His Asp Leu Ala Val Thr
225                 230                 235                 240

Phe Pro Gly Pro Gly Glu Asp Gly Leu Asn Pro Phe Leu Glu Val Lys
                245                 250                 255

Val Thr Asp Thr Pro Lys Arg Ser Arg Arg Asp Phe Gly Leu Asp Cys
            260                 265                 270

Asp Glu His Ser Thr Glu Ser Arg Cys Cys Arg Tyr Pro Leu Thr Val
                275                 280                 285

Asp Phe Glu Ala Phe Gly Trp Asp Trp Ile Ile Ala Pro Lys Arg Tyr
290                 295                 300

Lys Ala Asn Tyr Cys Ser Gly Glu Cys Glu Phe Val Phe Leu Gln Lys
305                 310                 315                 320

Tyr Pro His Thr His Leu Val His Gln Ala Asn Pro Arg Gly Ser Ala
                325                 330                 335

Gly Pro Cys Cys Thr Pro Thr Lys Met Ser Pro Ile Asn Met Leu Tyr
                340                 345                 350

Phe Asn Gly Lys Glu Gln Ile Ile Tyr Gly Lys Ile Pro Ala Met Val
                355                 360                 365

Val Asp Arg Cys Gly Cys Ser
370                 375

<210> SEQ ID NO 3
<211> LENGTH: 405
<212> TYPE: PRT
<213> ORGANISM: Mus musculus

<400> SEQUENCE: 3

Met Val Leu Ala Ala Pro Leu Leu Leu Gly Phe Leu Leu Leu Ala Leu
1               5                   10                  15

Glu Leu Arg Pro Arg Gly Glu Ala Ala Glu Gly Pro Ala Ala Ala Ala
                20                  25                  30

Ala Ala Ala Ala Ala Ala Gly Val Gly Gly Glu Arg Ser Ser Arg
            35                  40                  45

Pro Ala Pro Ser Ala Pro Glu Pro Asp Gly Cys Pro Val Cys Val
50                  55                  60

Trp Arg Gln His Ser Arg Glu Leu Arg Leu Glu Ser Ile Lys Ser Gln
65                  70                  75                  80

Ile Leu Ser Lys Leu Arg Leu Lys Glu Ala Pro Asn Ile Ser Arg Glu
                85                  90                  95

Val Val Lys Gln Leu Leu Pro Lys Ala Pro Pro Leu Gln Gln Ile Leu
            100                 105                 110

Asp Leu His Asp Phe Gln Gly Asp Ala Leu Gln Pro Glu Asp Phe Leu
            115                 120                 125

Glu Glu Asp Glu Tyr His Ala Thr Thr Glu Thr Val Ile Ser Met Ala
130                 135                 140

Gln Glu Thr Asp Pro Ala Val Gln Thr Asp Gly Ser Pro Leu Cys Cys
145                 150                 155                 160

His Phe His Phe Ser Pro Lys Val Met Phe Thr Lys Val Leu Lys Ala
                165                 170                 175

Gln Leu Trp Val Tyr Leu Arg Pro Val Pro Arg Pro Ala Thr Val Tyr
            180                 185                 190

Leu Gln Ile Leu Arg Leu Lys Pro Leu Thr Gly Glu Gly Thr Ala Gly
            195                 200                 205
```

```
Gly Gly Gly Gly Gly Arg Arg His Ile Arg Ile Arg Ser Leu Lys Ile
            210                 215                 220

Glu Leu His Ser Arg Ser Gly His Trp Gln Ser Ile Asp Phe Lys Gln
225                 230                 235                 240

Val Leu His Ser Trp Phe Arg Gln Pro Gln Ser Asn Trp Gly Ile Glu
                245                 250                 255

Ile Asn Ala Phe Asp Pro Ser Gly Thr Asp Leu Ala Val Thr Ser Leu
                260                 265                 270

Gly Pro Gly Ala Glu Gly Leu His Pro Phe Met Glu Leu Arg Val Leu
            275                 280                 285

Glu Asn Thr Lys Arg Ser Arg Arg Asn Leu Gly Leu Asp Cys Asp Glu
            290                 295                 300

His Ser Ser Glu Ser Arg Cys Cys Arg Tyr Pro Leu Thr Val Asp Phe
305                 310                 315                 320

Glu Ala Phe Gly Trp Asp Trp Ile Ile Ala Pro Lys Arg Tyr Lys Ala
                325                 330                 335

Asn Tyr Cys Ser Gly Gln Cys Glu Tyr Met Phe Met Gln Lys Tyr Pro
                340                 345                 350

His Thr His Leu Val Gln Gln Ala Asn Pro Arg Gly Ser Ala Gly Pro
            355                 360                 365

Cys Cys Thr Pro Thr Lys Met Ser Pro Ile Asn Met Leu Tyr Phe Asn
            370                 375                 380

Asp Lys Gln Gln Ile Ile Tyr Gly Lys Ile Pro Gly Met Val Val Asp
385                 390                 395                 400

Arg Cys Gly Cys Ser
                405
```